(12) United States Patent
Johnson et al.

(10) Patent No.: US 12,150,880 B2
(45) Date of Patent: *Nov. 26, 2024

(54) JOINT BRACE WITH DISTRACTING HINGE

(71) Applicant: Icarus Medical, LLC, Charlottesville, VA (US)

(72) Inventors: David T. Johnson, Charlottesville, VA (US); Philip Miller, Charlottesville, VA (US); Ben Scire, Hopkinton, MA (US); George Miroulis, Virginia, VA (US); Evan Eckersley, Charlottesville, VA (US); Collin Farill, Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/235,319

(22) Filed: Aug. 17, 2023

(65) Prior Publication Data
US 2024/0024145 A1    Jan. 25, 2024

Related U.S. Application Data

(60) Continuation-in-part of application No. 18/075,203, filed on Dec. 5, 2022, now Pat. No. 11,806,264, which is a continuation-in-part of application No. 17/902,683, filed on Sep. 2, 2022, now Pat. No. 11,612,506, application No. 18/235,319 is a
(Continued)

(51) Int. Cl.
*A61F 5/01* (2006.01)

(52) U.S. Cl.
CPC .... *A61F 5/0125* (2013.01); *A61F 2005/0139* (2013.01); *A61F 2005/0165* (2013.01)

(58) Field of Classification Search
CPC ............ A61F 5/0125; A61F 2005/0139; A61F 2005/0165; A61F 13/048; A61F 13/107; A61F 2013/49096; A61F 5/01; A61F 5/026; A61F 5/028; A61F 2/30; A61F 2002/30624
See application file for complete search history.

(56) References Cited

U.S. PATENT DOCUMENTS 5,038,763 A   8/1991  Wiggins
5,213,094 A   5/1993  Bonutti
(Continued)

FOREIGN PATENT DOCUMENTS

ES   2269373 T3 *  4/2007  ........... A61F 5/0125
WO   WO-2007107150 A1 *  9/2007  ............... A61F 2/64

OTHER PUBLICATIONS

ODRA product information, https://odra.ca/en/.
(Continued)

*Primary Examiner* — Tarla R Patel

(57) ABSTRACT

An assembly for a body joint orthotic that generates a distraction force to the joint that can be synchronized with the flexion of said joint. The hinge may be polycentric or unicentric. For a polycentric hinge, the distraction can be generated by varying the distance between the axes of rotation of the two pivot points. For a unicentric hinge, the distraction can be generated by increasing the length of at least one of the arms that connects the strapping element which holds the orthotic to the limb or body part to the hinge. The synchronization of the amount of distraction to the angle of flexion may be achieved by purely mechanical mechanisms or involving a motor.

30 Claims, 62 Drawing Sheets

Related U.S. Application Data continuation-in-part of application No. 17/211,635, filed on Mar. 24, 2021, now Pat. No. 11,819,436, which is a continuation of application No. 17/074,542, filed on Oct. 19, 2020, now Pat. No. 11,564,824, and a continuation of application No. 17/074,571, filed on Oct. 19, 2020, which is a continuation-in-part of application No. 15/585,968, filed on May 3, 2017, now Pat. No. 10,806,619, said application No. 17/074,542 is a division of application No. 15/585,968, filed on May 3, 2017, now Pat. No. 10,806,619.

(60) Provisional application No. 63/463,845, filed on May 3, 2023, provisional application No. 62/331,315, filed on May 3, 2016.

(56) References Cited

U.S. PATENT DOCUMENTS

| | | | |
|---|---|---|---|
| 6,953,442 | B2 | 10/2005 | Motokubo et al. |
| 7,198,610 | B2 | 4/2007 | Hf |
| 8,679,042 | B2 | 3/2014 | Kausek |
| 10,765,548 | B2 | 9/2020 | Luo |
| 11,819,436 | B2* | 11/2023 | Johnson ............... A61F 5/0125 |
| 2011/0184325 | A1 | 7/2011 | Behzadian et al. |
| 2015/0007422 | A1* | 1/2015 | Cavanagh ............ A43C 11/165 |
| | | | 29/434 |
| 2020/0346888 | A1* | 11/2020 | Kruse ............... A43B 23/0205 |
| 2020/0375778 | A1 | 12/2020 | DiAngelo et al. |

OTHER PUBLICATIONS

Ornetti, P. et al., Clinical effectiveness and safety of a distraction-rotation knee brace for medial knee osteoarthritis, Annals of Physical and Rehabilitation Medicine 58 (2015) 126-131.

Natenstedt, J., Joint Unloading ankle brace to aid cartilage regeneration, Semantic Scholar, Sep. 21, 2015, https://www.semanticscholar.org/paper/Joint-unloading-ankle-brace-to-aid-cartilage-Natenstedt/b23d7e3aa3973415bae24481f4d21912e2a8a8d1.

Spinal Decompression Scoliosis Brace Combo by Meditrac-Vertetrac + D.B.S. (Dynamic Brace System) product information, https://www.rehabmart.com/product/spinal-decompression-scoliosis-brace-combo-meditrac-52717.html?gad_source=1&gclid=Cj0KCQiAj_CrBhD-ARIsAliMxT_t-eoFXbU2Vwc42PnMRz905x08g6uJnH4KGcojOROkakgAK_YN9VYaAIFKEALw_wcB.

DDS product information, https://ddsmed.com/products/dds-oa-pro/.

Imboden, Madeleine Alora-Ivy, Design and Evaluation of an Offloading Orthosis for Medial Knee Osteoarthritis, Thesis submitted to the University of Ottawa, 2021.

BREG product information, https://www.breg.com/products/knee-bracing/functional-oa/thruster-rlf/.

Bertomeu, J. M. B. et al., Development of a hinge compatible with the kinematics of the knee joint, Prosthetics and Orthotics International, Dec. 2007, 31(4): 371-383.

Sombeek, J., A review on joint distraction including non-invasive alternatives for knee joint distraction, Bachelor research study, 2013, https://protect-us.mimecast.com/s/RTruCwpEYmt0JKyAsVxMzb? domain=fse.studenttheses.ub.rug.nl.

* cited by examiner

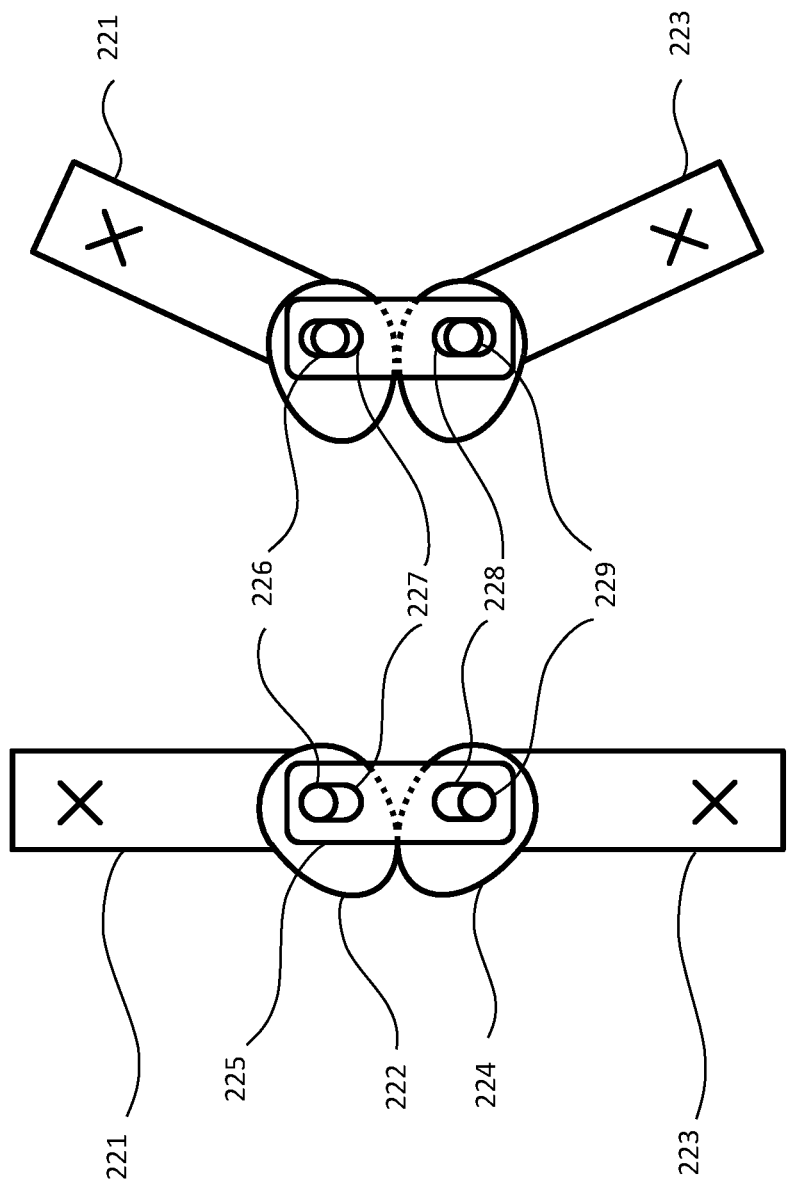

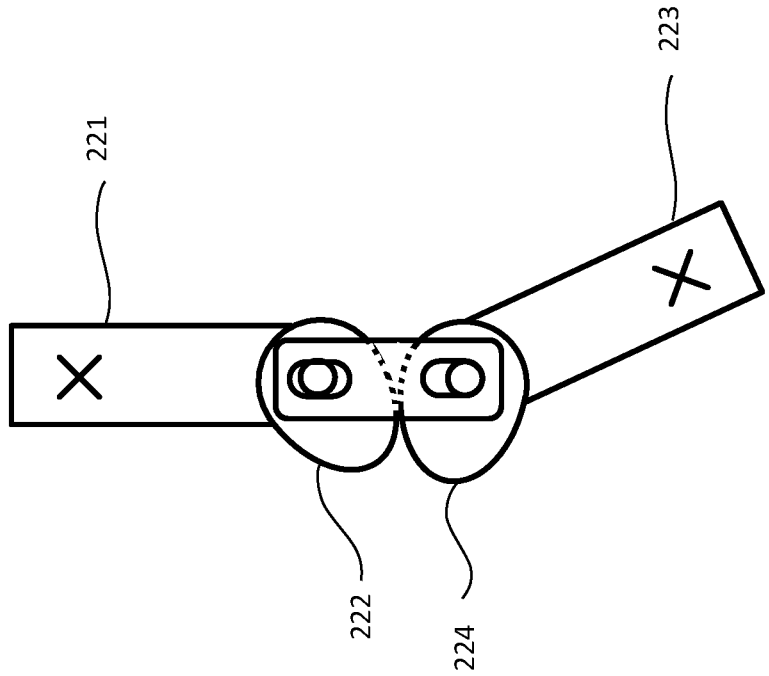
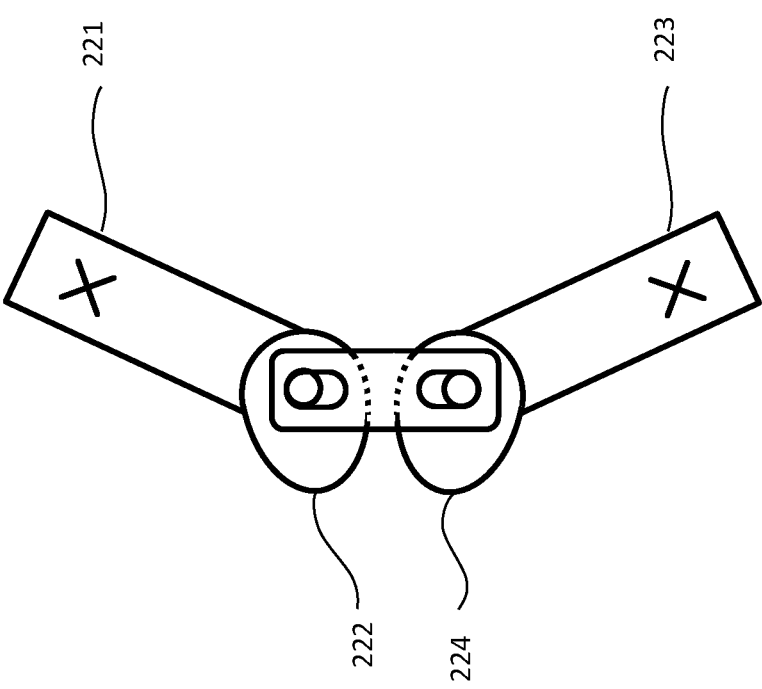

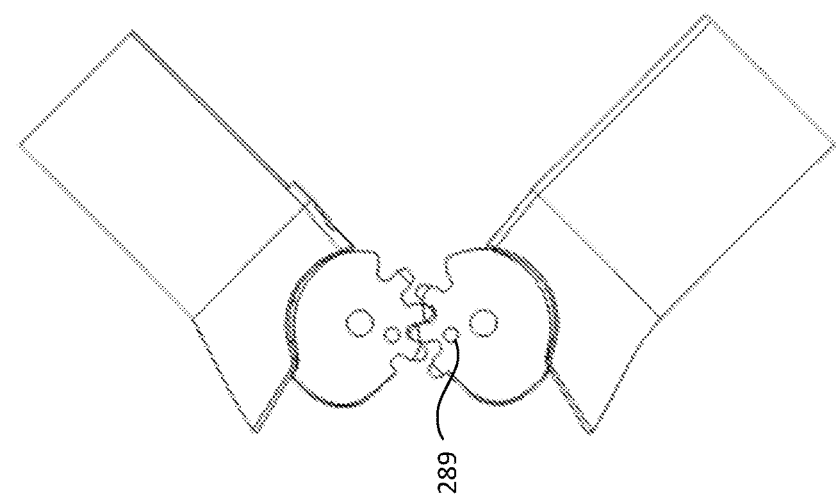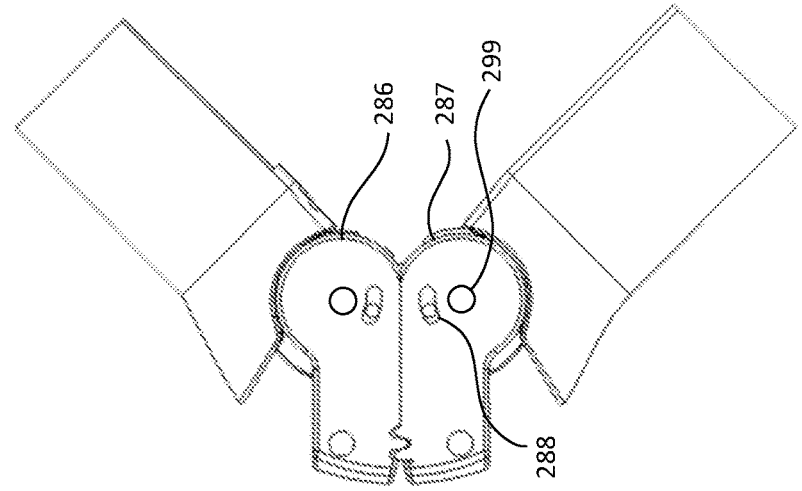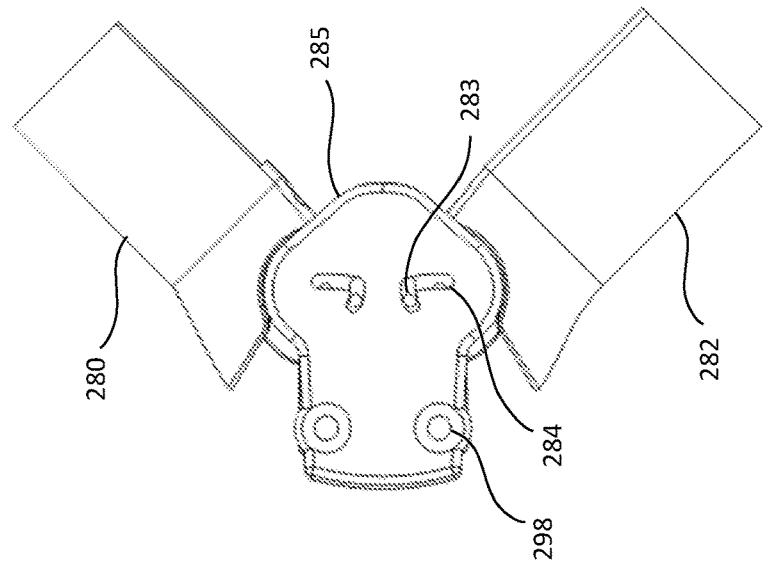

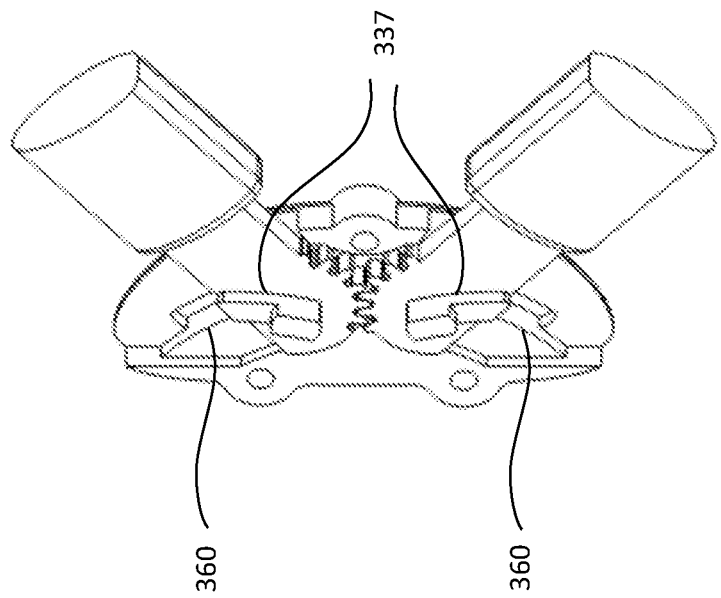
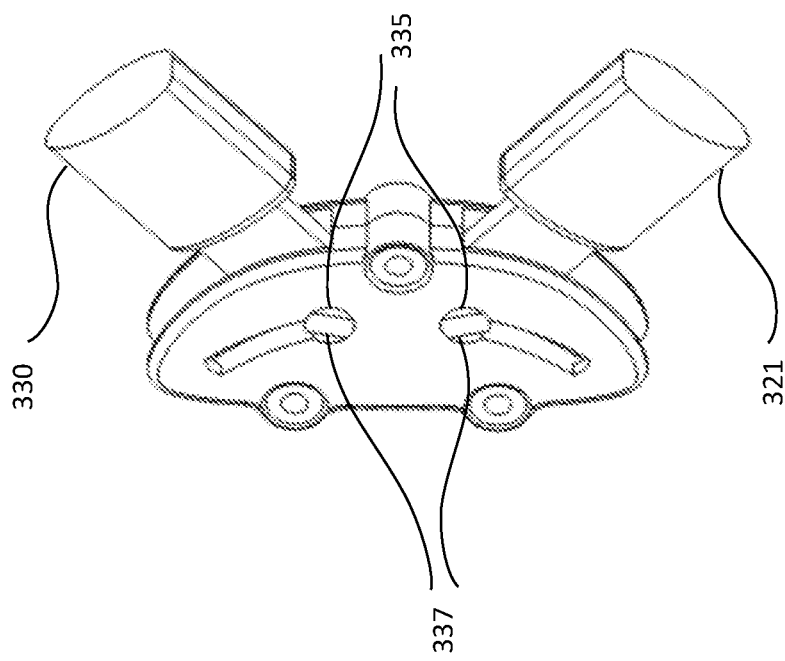

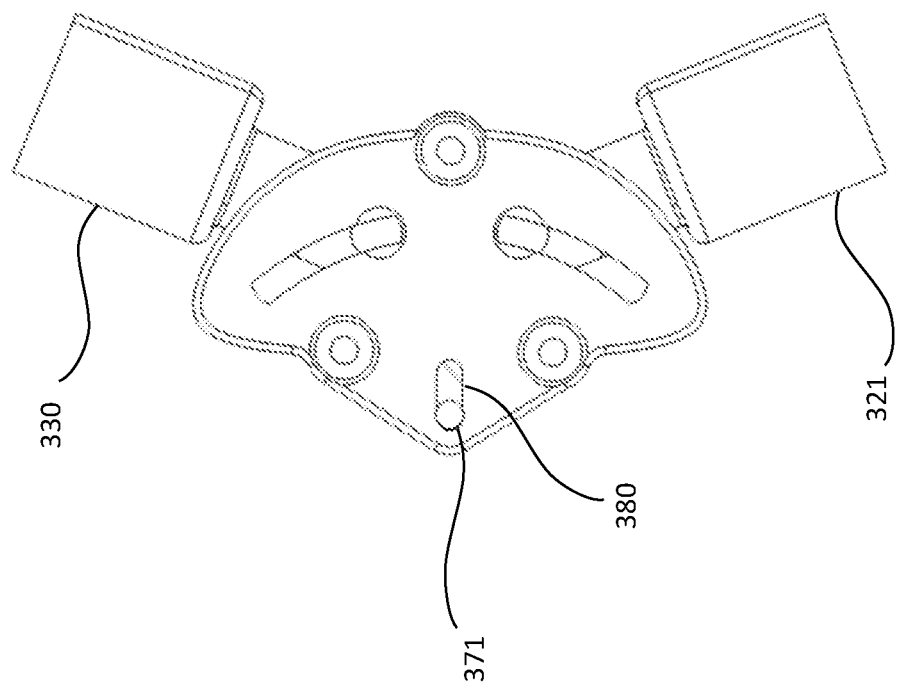
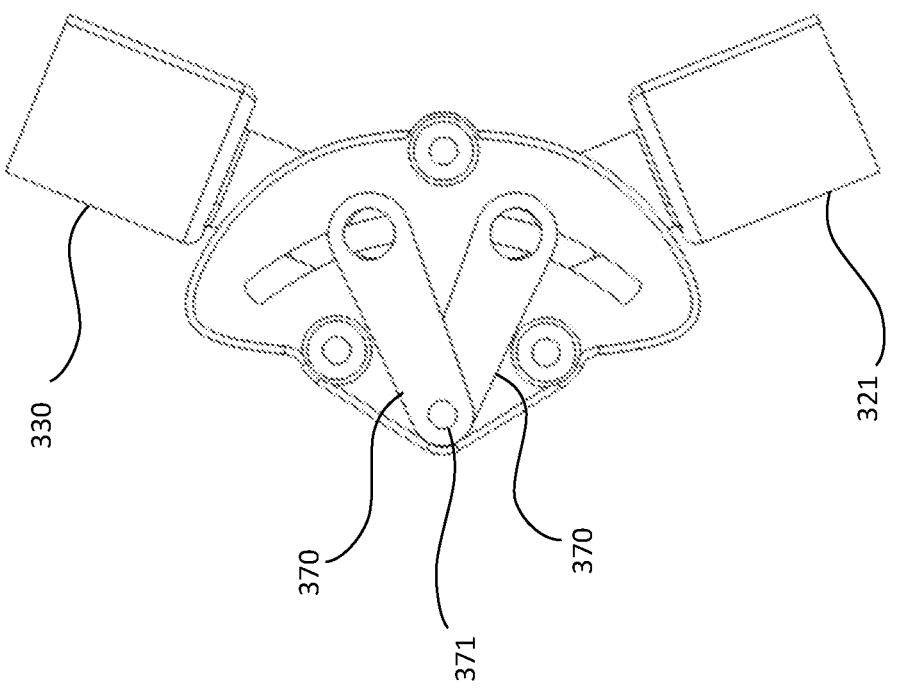

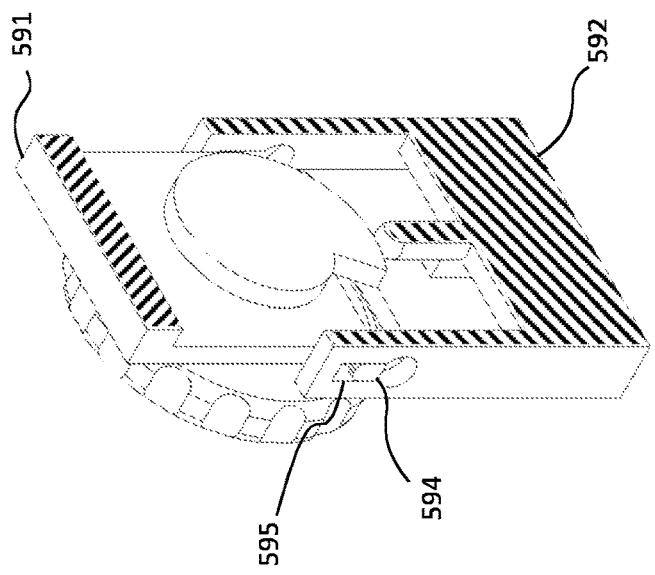
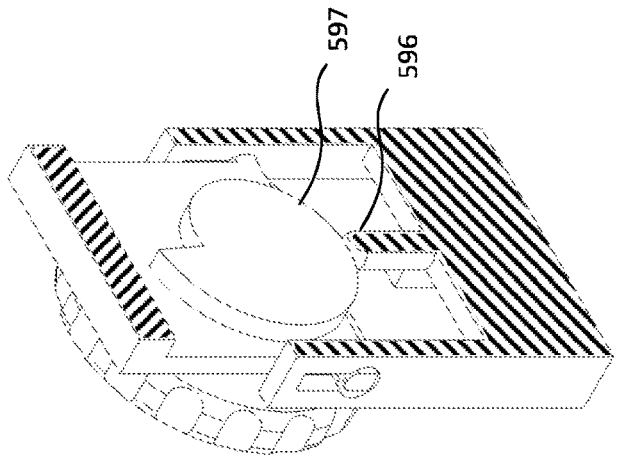
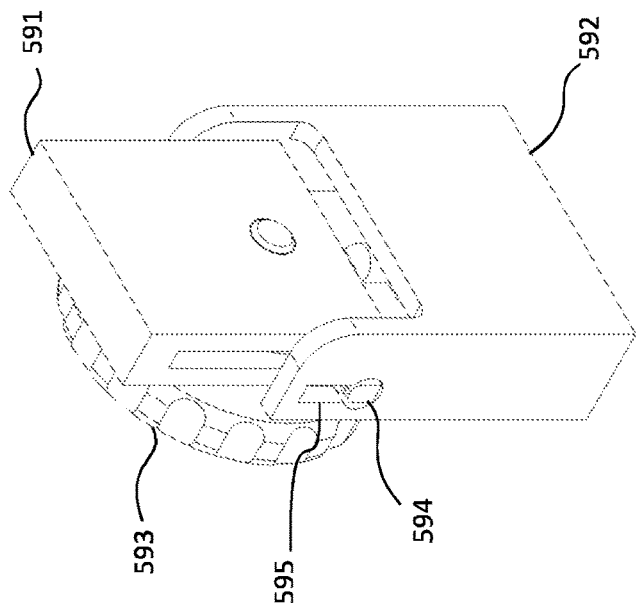

JOINT BRACE WITH DISTRACTING HINGE

CROSS-REFERENCE TO RELATED APPLICATIONS

The present application is a continuation-in-part of and relies on the disclosures of and claims priority to and the benefit of the filing dates of U.S. patent application Ser. No. 17/211,635, filed Mar. 24, 2021. The present application relies on the disclosures of and claims priority to and the benefit of the filing date of U.S. Patent Application No. 63/463,845, filed May 3, 2023. The present application is a continuation-in-part of and relies on the disclosures of and claims priority to and the benefit of the filing dates of U.S. patent application Ser. Nos. 17/074,571 and 17/074,542, filed Oct. 19, 2020, which rely on the disclosures of and claim priority to and the benefit of the filing date of U.S. patent application Ser. No. 15/585,968, filed May 3, 2017, which claims priority to and benefit from U.S. Provisional Patent Application No. 62/331,315 filed on May 3, 2016. The disclosures of those applications are hereby incorporated by reference herein in their entirety.

The present application is a continuation-in-part of and relies on the disclosures of and claims priority to and the benefit of the filing dates of U.S. patent application Ser. No. 18/075,203, filed Dec. 5, 2022, which is a continuation-in-part of and relies on the disclosures of and claims priority to and the benefit of the filing dates of U.S. patent application Ser. No. 17/902,683, filed Sep. 2, 2022.

FIELD OF THE INVENTION

The present invention disclosed herein relates generally to orthotic joint braces to relieve pain and discomfort by unloading and/or distracting the joint by redistributing the weight on the joint to other parts of the body and/or providing assistance in extension of the joint, as well as pulling apart or pushing apart the joint.

BACKGROUND OF THE INVENTION

Osteoarthritis (OA) is a degenerative joint disease characterized by chronic inflammation, breakdown, and eventual loss of the joint cartilage, causing deterioration of the underlying bone. The patellofemoral compartment, in particular, is one of the most frequent points of knee pain experienced by those with OA. While unloading braces have been used as inexpensive therapeutic solutions for knee OA, they have been overwhelmingly ineffective in preventing and reducing joint pain.

Arthritis is currently the most common cause of disability among adults in the United States. More than one hundred different rheumatic conditions fall under arthritis, the most common of which is osteoarthritis (OA), a degenerative joint disease marked by a chronic deterioration of joint cartilage and the underlying bone. OA is one of the most common joint disorders in the United States, and the number of those afflicted is only projected to increase in the midst of an aging population and increasing levels of obesity. Twenty-seven million adults in the U.S. alone are affected by the disease. As the most typical type of arthritis, the disorder has commonly affected the knee, and the patellofemoral (PF) compartment within the knee joint in particular has been one of the most frequent points of knee pain in the outpatient setting. The PF compartment performs a key role in daily movement and activity, enabling mobility over a large range of motion through flexion, extension, and rotation of its associated components. One of the most non-invasive and widely accepted methods for prevention of further deterioration of the articular cartilage within the knee joint is by using a knee brace. The joint itself, including its underlying cartilage, can only support a certain amount of force before the cartilage begins to wear away, and unloading knee braces decrease the amount of force on the joint.

According to the American Academy of Orthopedic Surgeons and the U.S. Center for Disease Control and Prevention, nearly half of Americans develop symptoms due to knee OA by the age of 85, and the incidence rate for PF pain syndrome has been reported to be approximately 22 adults for every 1000 adults per year. In addition, up to 10 percent of the U.S. population suffers from pain and loss of function from patella arthritis and cartilage wear. The high prevalence of these injuries suggests that the condition affects a significantly large portion of the adult population and will have a growing impact on healthcare systems in the future. On average, total knee arthroplasty, or knee replacement surgery, costs between $10,000 and $30,000, and over 600,000 surgeries are performed each year. Other surgical procedures such as articular cartilage restoration, osteotomy, and unicompartmental knee replacement, as well as corticosteroid and hyaluronic acid injections to reduce inflammation and absorb shock, respectively, are also very expensive. Thus, preventative treatments that reduce the amount of stress, pressure, and invasive procedures on the knee are necessary for improving the quality of life for patients and for reducing potential medical costs.

In addition, robust braces enable those with severe joint injuries to remain active when joint replacement is not appropriate. It is estimated that 27 million adults in the U.S. are suffering from osteoarthritis, and 454,652 patients with severe joint injuries and arthritis received knee replacement surgeries in 2004. Currently, nonpharmacological approaches, such as physical therapy, and pharmacological methods are primarily used to treat knee OA. When these are proven to be ineffective, the treatment method culminates to surgery, and drawbacks involve internal joint bleeding, bone healing failure, nerve or tissue damage, and infection. Thus, the development of a knee brace that significantly unloads force on afflicted joints, prevents pain and disability, and does not require many other treatments in conjunction is necessary to address the challenges associated with establishing a purely non-pharmacological, orthotic approach to treating knee OA.

Other conditions such as knee flexion contracture (KFC), quadriceps weakness, and neurological conditions that impact proper muscle and joint function, are also lacking in treatment options. A brace that can transfer forces away from the knee joint and quadriceps has promise to uniquely benefit patients who may suffer from these conditions. Transferring forces away from the joint may also allow the patient to delay or prevent surgical procedures such as a joint replacement.

Cartilage is a non-vascular lubricous material that allows bone to slide over bone and absorbs shocks in human and animal joints. When cartilage is damaged through injury, over-use, or age-related phenomenon joint motion can become hindered and painful. OA is the most common form of arthritis and is responsible for the breakdown of joint cartilage.

DESCRIPTION OF RELATED ART

Osteoarthritic knee braces primarily comprise a rigid, or semi-rigid, frame with an upper frame member called an "upper cuff" situated across the anterior thigh, and a "lower cuff" across the anterior or posterior tibia; and, straps are on the opposing side of the cuffs to secure the frame onto the user's leg. The upper and lower cuffs are connected by a rotary hinge assembly that pivots through a user's normal range of motion, or less depending on the injury.

In OA, the disease process includes degradative enzymes that erode the articular cartilage, leading to bone-on-bone contact, which is the primary source of the user's knee pain. OA knee braces classified as "unloading" braces pull the femur and tibia apart so that there is not bone-on-bone contact when the user is load bearing, such as walking, standing, exercising, etc. This is accomplished by the brace lifting the femur, and/or pulling down the tibia, or otherwise keeping the femur and tibia condyles from making direct contact through the actions of the upper and lower cuffs locking the femur and tibia in positions relative to the other.

Unloading knee braces may also comprise hinge assemblies that exert a force in the medial to lateral direction to push the knee joint inward, thus separating the femur and tibia condyles. For example, there may be one hinge assembly in the brace, such as for a brace to treat OA in the left medial compartment with a hinge assembly on the medial side of the knee joint; or hinge assemblies on both sides. The hinge assembly may comprise a component (e.g., an inflatable pad) that pushes the knee joint laterally, e.g., inward and/or apart, to unload forces on the medial side of the knee, and thus reduce the user's pain.

The hinges in unloading knee braces may also comprise components similar to a built-in braking system where the user experiences an increase in tension as the knee is bent to prevent the user's knee from collapsing while bending. The hinge assembly and cuffs engage in a majority of the work that the leg muscles would otherwise do to stabilize the knee joint through its entire range of motion.

More recently, a number of OA knee braces have been marketed to consumers who wish to maintain an active life-style in spite of their medical condition. OA knee braces are now available that comprise hinge assemblies with the ability to exert forces to assist the user in movement, otherwise known as "swing assistance" or "knee extension assistance". The hinge's exerted restoring forces can be counter to the user's original direction of movement, such as propelling the user's knee from a flexed to an extended position after the user has bent down. The hinge assemblies primarily comprise springs and/or elastic members (tensioning elements) that store potential energy when the user is bending their leg, such as crouching down, during which the elastic members are stretched, or the springs members are compressed or stretched. The restoring force generated from the compression or stretching is used to assist the user when they move to extend their leg.

What is needed within the OA knee brace industry, though, is a knee brace that effectively both unloads the user's weight off the knee joint while dampening downward forces and generating restorative resistance forces that provide stability and support to weakened muscles. It would also be beneficial if the knee brace provides knee extension assistance to the active user. There is also a need for an improved mechanism of unloading that does not require pushing the knee inward, but instead relies upon a well-fitting rigid or semi-rigid frame and straps, and/or hinge assemblies that are of an adjustable tension that can be activated by the user as needed, and of significantly higher tension levels than the prior art's to engage in the mechanical work that is normally done by the muscles of the knee while pulling the femoral and tibia condyles apart.

FIG. 21A shows a schematic of a human right leg (210). The femur and tibia are shown and the medial side (toward the center of the body) and the lateral side (away from the center of the body) are labeled. Knee braces to unload the medial or lateral compartments of the knee are known in the art such as the Unloader One manufactured by Össur. These knee braces use a three point bending system that applies forces above and below the knee. FIG. 21B shows a schematic of three point bending brace (212) applied to the lateral side of the leg. Typically, the braces have an adjustment that introduces an angle at the hinge point (214) between the upper and lower frame elements. Strapping the angled brace to a straight leg produces forces shown by the block arrows in FIG. 21B. Those forces generate a moment of rotation across the knee thereby "unloading" the medial side as shown by the gap (216).

While this way of unloading has been shown to be effective in some cases, studies have been conducted that show that only ~10%-15% of the physiologically needed unloading force ($F_u$) can be applied lest the pain associated with using orthosis interfere with its successful adoption. In addition, unloading a joint by applying a three point bending system can only be used on one side of the joint at a time. By necessity, the moment of rotation induced by a three point bending system causes increased pressure on the side of the joint opposite of the unloading. Thus, a three point bending system will only work for medial unloading or lateral unloading, but not both at the same time. For patients sensitive to any additional loading on their joint, or with multi-compartment unloading needs, or with a need for a $F_u$ of large magnitude, a three point bending system is less than optimal.

There are several other ways to treat or manage joint cartilage damage, too. These include treatment of symptoms such as icing and pain medications, managing joint movement such as bracing, or joint replacement or augmentation via surgery. Recently, surgical joint distraction has been used more frequently to promote the regrowth and repair of joint cartilage. Surgical joint distraction has been shown to be effective for knee and ankle joints.

Knee Joint Distraction (KJD) is a surgical procedure wherein pins are inserted into the patient's tibia and the femur. Rods connect the pins and by adjusting the length of the rods, the upper and lower surface of the knee can be separated. The amount of separation may be increased gradually over a period of days to the desired target.

The knee is fixed in a fully extended position and left for a period of time from 6 weeks to more than 8 weeks. Most therapies leave the knee fully extended during this time. Some alternative therapies disconnect the rods during this time and manually flex the afflicted leg to stimulate the knee and promote the movement of fluid.

During the initial procedure when the pins are inserted, the joint may be treated to stimulate cartilage regrowth. Such treatments may include the initiation of surgical 'damage' (e.g., small cuts or holes), the introduction of healthy cartilage, or the injections of stem cells. In addition, medication may be prescribed during the distraction period to simulate cartilage regrowth.

The conclusion of a summary of nine studies of KJD procedures by Goh, et al. reported in the literature stated, "There were significant improvements in WOMAC index, VAS pain score and joint space width following KID, which persisted up to 9 years. KID also demonstrated comparable clinical outcomes with high tibial osteotomy and total knee arthroplasty." (The role of joint distraction in the treatment of knee osteoarthritis: a systematic review and quantitative analysis; Orthop Res Rev. 2019; 11: 79-92).

Complications of surgical KJD can include pin-tract infections at the sites of the bone pins. KJD surgery is conducted under anesthesia and the typical risks apply. In addition, the afflicted leg is locked in full extension for the duration of the distraction period. The sites and angles of the tibia and femur pins are selected to be compliant with the potential need for future total knee replacement surgery.

KJD surgery is believed to be successful because load is taken off the damaged cartilage allowing it to regrow and repair. By physically separating the joint face, more fluid is able to circulate which also promotes healing.

It would be highly desirable to obtain the benefits of KJD surgery without the risks, discomfort, and expense associated with surgical procedures. A study run in 2013 by Khademi-Kalantarii, et al. and published in the Journal of Bodywork and Movement Therapies (Volume 18, Issue 4, October 2014) titled the Effects of Non-Surgical Joint Distraction In the Treatment of Severe Knee Osteoarthris concludes that non-surgical distraction of the knee joint "can result in further improvement in pain relief, increased functional ability and better quality of life in patients". However, the method of distraction used to achieve this outcome was by hanging a weight from the ankle of the affected leg while lying supine. The distraction sessions were only 20 minutes long. This method described is inconvenient and difficult to reproduce remotely at home for some patients. What is needed is an easy to use, portable device to provide non-surgical joint distraction.

SUMMARY OF THE INVENTION

Various embodiments of the present disclosure comprise a novel type of unloading knee brace that has been designed to reduce the amount of pain that patients experience as a result of PFP or knee joint OA. The knee braces and hinge assemblies disclosed herein work by using one or a combination of the following mechanisms:
  a. generating a force or forces opposing the bending or contracting/flexion of the knee joint,
  b. applying a force or forces to the sides of the leg that result in unloading one or more compartments of the knee,
  c. hinges that distract forces from one or both sides of the knee in the tibiofemoral compartments, and/or
  d. hinges that are curved that conform to the shape of the user's knee.

The braces described herein are suitable for a knee joint, an elbow joint, an ankle joint, a shoulder joint, a hip joint, or a wrist joint; while application of this technology for the knee joint will be presented here in detail, one of ordinary skill in the art could readily apply this disclosure and teachings herein to an elbow, hip, shoulder, ankle or a wrist brace. The brace effectively unloads a significant amount of force within the knee by using a low- to high-tension resistance mechanism described herein, and by distributing the force to other areas of the body. This results in reduced contact pressure in areas of the knee afflicted with OA, and therefore less pain. Other braces are described that have different mechanisms of unloading or distracting pressure in joints as well.

The invention disclosed herein is an article and method to achieve joint distraction without the need for surgical intervention. In aspects, the invention can be even more effective when used in conjunction with medications, stem cell injections, cartilage plugs or grafts that will stimulate the growth and repair of the patient's cartilage.

Some embodiments described herein allow the user to: quickly (e.g., in aspect from about 1-5 seconds, for example) engage and disengage tension in each joint mechanism as needed, including in aspects while the brace is being worn; adjust the amount of tension, including while the brace is being worn and without the need for a medical professional's assistance; allow for tension to increase with increasing degrees of flexion; and limit the range of extension and flexion in the joint. The device is particularly suitable for people afflicted with patellofemoral osteoarthritis (OA), cartilage damage, meniscus damage, knee stability issues, and other types of knee conditions for which pain intensifies during the bending or contracting of the knee, and for patients who lack the strength (e.g., quadriceps weakness) to extend their knees either during exercise or simple life functions, such as standing from a seated position. The various embodiments of the brace and hinge assemblies disclosed herein provide enhanced support for stabilizing the knee joint, and they can enhance the user's physical performance by providing extension assistance. Another version of the brace may have the tensioning elements oriented such that the brace resists extension and assists with flexion. The tensioning mechanism may be used with or without the device. This type of device can treat knee flexion contracture, which may be used to help patients recovering from joint replacement surgery improve range of motion.

The various embodiments of the brace and hinge assemblies disclosed herein may also be applied to other orthotics designed to treat other human joint, such as elbows, shoulders, ankles, wrists, and hips, wherein a support in one part of the joint is operatively connected to another part of the joint via a variety of the tensioning mechanisms described below that may alter the amount of force between parts of the joint. For example, a shoulder brace may apply a posteriorly directed force through the shoulder to unload the anterior direction, or other direction(s), to alleviate pain. In this example, part of the shoulder brace will attach to the injured part of the body and will anchor to another part of the body, such as the shoulder opposite to the injured shoulder. Rigid and semi-rigid parts may be used in conjunction with the tensioning mechanism to create the desired force environment for the joint.

Unloading Brace Vertical Support

The various embodiments of the present disclosure comprise a knee brace that effectively unloads the user's weight off the knee joint via a rigid or semi-rigid vertical support that, in aspects, partially or completely connects to the user's femur and tibia, and with a pivoting hinge assembly connecting an upper and lower portion of the vertical support. In some embodiments, the posterior side of the vertical support comprises one to three straps on the upper and on the lower portion, or other mechanisms to connect the device to the knee, or elbow, or ankle, by way of example, which may be oriented in a variety of ways relative to the vertical support.

It is noted that the vertical support of the present disclosure may also be used with a wide variety of types of hinge assemblies previously known in the art for use by knee patients in order to effectively unload weight from the knee joint. One such assembly may be the combination of rigid and semi-rigid materials that enable the brace to be connected to or contained within an elastic sleeve or support that partially or fully encompasses the joint.

The various embodiments of the knee brace comprise a vertical support with an upper frame and a lower frame that are connected via a hinge assembly on one side (for a medial or lateral brace), or via two hinge assemblies (for a full brace). Furthermore, in embodiments, the vertical support comprises an arcuate, curved, semi-circular rigid or semi-rigid unit situated above and below the knee, and connected via a geared or ungeared, pivoting hinge assembly, in examples. The upper and lower frames may further comprise at least one strap or other connection mechanism to secure the brace to the user's leg; and the upper portion may have straps and/or a material for supporting the back of the thigh to effectively distribute force away from the knee. The upper and lower portions may also be secured with a hook and loop type material, or a clip-type fastener or similar method.

The brace can be one-sided or bilateral (as in a right and left, or medial and lateral support), the determination of which is based on whether the knee is injured medially or laterally, or in the femoral compartment, which is approximately central. The tensioned brace hinge assembly should be proximal to the injured part of the knee. A user benefiting from a high-tension brace would ideally use a brace with both lateral and medial side supports to generate torque on both sides.

The amount of torque can be modified by the strength and number of elastic materials, and the amount of torque may vary on each side to address the user's specific OA condition. The brace frames disclosed herein are capable of targeting damage to the patellofemoral compartment; but other types of knee injuries and medical conditions may benefit from only a side support vertical member and/or one hinge assembly.

The brace can also accommodate a patient who experiences more symptoms of OA in one compartment of the knee than the others, by applying a force on the opposing side of the unicompartmental OA present in the patient's knee. This can be achieved by a variety of methods known to the art; for example, the condylar pad on one side of the joint may be stiffer or thicker than the condylar pad on the other side of the joint. The use of shims that can be connected to the side plate or hinge capsule and adjusted based on the degree of varus/valgus present in the user's knee may also apply.

Another application of the brace may involve using the same tensioning mechanisms taught herein to assist flexion instead of opposing flexion. This could be accomplished by changing the location of the tensioning element such that it is located on the posterior side of the hinge assembly and encourages flexion of the joint by maintaining tension in the tensioning element. This application of the device would be useful for those recovering from an injury or undergoing physical therapy, as an indication of knee health after recovery is the range of motion (flexion) the knee can achieve as swelling decreases in the joint.

The brace can be partially or fully automatically designed by software that generates a design based on a 3D scan consisting of cloud point data, accompanied by information on the user such as the severity of their injury, information on the misalignment based on radiographic measurements, measurements extrapolated from 3D scans, and other user biometric data such as height, weight, and age, or any combination of this information. The model developed can also use this information to develop implantable devices within the joint to improve joint function. These may also be used to serve as a substrate for cartilage growth on the implant or to shape how cartilage grows in the joint in a desired way. The implant may also be placed to assist cartilage growth in another area that is near or related to the implant. Artificial intelligence or machine learning can be used with or without finite element analysis to determine the shape of an effective or assistive implant, and AI, machine learning, and FEA, or combinations thereof may consider all of the input data above to improve overall body mechanics. This approach may be applied to more than just the knee, but also the ankle and hip, and how these joints relate to each other to improve body function. This can also be applied to the shoulder, elbow, wrist, back, and neck joints, or combinations thereof.

Brace Materials: In embodiments, the vertical support is made from rigid and/or semi-rigid plastic, metal, other lightweight materials, such as carbon fiber or another suitable material that are mostly inelastic yet flexible, and thus distribute weight-load knee forces. 3D printing with common thermoplastics are ideal materials for fabricating the brace described herein.

Because the knee braces are subjected to high tension or high torque from the hinge assembly, tight, form-fitting contact with the body is preferred. The brace may further comprise light padding lining the upper and lower portions, and/or the straps or other connection mechanisms. In aspects, the fit and material composition are designed to provide a coefficient of friction between the brace and a user's leg so as to increase adhesion to the user's leg, and thus facilitate the transfer of weight-load forces off the knee joint, while remaining comfortable to wear. The upper and lower portions and/or straps or other connection mechanisms can be contained or built within an elastic sleeve to reduce the friction coefficient at the body/brace interface. The fabrication method combined with using strong and lightweight materials will facilitate this design feature. Furthermore, the brace can be made from common materials, such as braided tensioning elements, where applicable, and may therefore be less expensive and more accessible to users that may not normally be able to afford a performance brace. 3D-printed versions of the brace frame may have padding that is 3D printed continuously or separately attached. 3D printed padding comprises a compressible matrix that conforms to the body and provides cushion.

In aspects, the brace frame, or vertical support, comprises: an upper rigid, or semi-rigid, frame, sized to fit a user's femur adjacent to and above a user's knee joint, and a lower rigid, or semi-rigid, frame, sized to fit a user's tibia adjacent to and below the user's knee joint.

Size: The knee brace can be custom made for the user based on one or more of: size, weight, level of physical activity of the user; weight and flexibility of the brace; etc. Or it can be sold over-the-counter based on size (for example, small, medium or large), and/or by level of tension (low/medium/high). Or, the brace may be custom made to fit a particular user using digital imaging. In a preferred embodiment, the brace is form-fitting to the knee joint, lower femur, and top tibia, in order to redistribute the load off of the knee joint, when the device is being used to unload forces. The brace may conform to digital images or a three-dimensional scan and this fitting process may be automated or partially automated. Software can orient the leg in the proper direction and scale the leg and brace properly.

Hinge Assemblies

In embodiments, the present invention comprises at least one tensioning element (e.g., a tensioning element, an elastic band, or a spring) of low, moderate, or high tension, two intermeshed, teethed gears rotating in unison as the user flexes and extends the knee joint, and a method of controlling the degree of extension and flexion the joint can achieve while the user is wearing the brace. Other embodiments do not require teethed gears but instead are toothless with curved adjacent parts that glide on each other and are made from a low-friction material, in aspects.

Hinge assemblies can be used with the unloading brace vertical support disclosed herein; and/or with other knee braces or joint braces known in the art.

In the hinge assemblies disclosed herein, the amount of tension for unloading can be adjusted by, for example: adding more tensioning elements of the same or of different levels of tension; adding more tensioning elements of the same or of different levels of diameter; and/or by substituting tensioning elements with different elastic properties (e.g., stiffer bands or springs to create more tension; and/or by moving a hinge component to fix one end and/or the center of a tensioning element to prevent it from further extension, thus increasing the tension in the element (e.g., see embodiments 2-4 of the hinge assembly, infra)). The hinge assembly may include smoothed sections to prevent damage to the tensioning element(s), and to allow for drawing-stretching-extending the tensioning element over the hinge, whether or not the tensioning element(s) come into contact with the rotating gears.

When more than one tensioning element is used, the tensioning elements may be located, in certain aspects, adjacent longitudinally in the anterior side of the hinge assembly, and/or the posterior side, such as in parallel, or one atop the other, such as in series. Another design feature, in aspects, is that a plurality of tensioning elements improve safety of the brace by providing a backup support in the unlikely event that a band breaks or detaches.

If a tensioning element is to be used, in embodiments, hinges with bands as large as ¾ inch and as little as ⅛ inch in diameter are envisioned, and larger and smaller bands could be used in the same brace.

Tensioning elements having different levels of tension comprise materials, in examples, such as: real rubber, braided synthetic rubber cords, exotic elastic or other elastic materials. Braided bands offer protection to the elastic material, and other bands can use thin protective sheaths or a wet or dry lubricant to allow for smooth drawing over the hinge, in aspects. Bands that are 3D-printed with many individual elastic strands oriented in the direction of tension will make a preferred tensioning element.

An additional hinge assembly may be envisioned that is comparative to the gliding and rolling of the knee joint. This version may involve a slot that allows for the gliding and rolling motion of the knee wherein the slot is a pin in the upper and or lower frame. A tensioning element may be anchored between the upper and lower frames to slow or to impede the forward movement of the knee joint, in a way that best matches the natural movement of the knee. As used herein, a slot may be disposed all the way through a component or partially disposed through a component.

In embodiments, hinge mechanisms described herein can be applied to other devices, and are not limited to an orthosis (e.g., brace). They can also be adapted to function inside the body and attached directly or approximately on a joint. The hinge and other aspects of the current invention can be implantable (e.g., surgically implanted). For example, in embodiments, the device described herein and in the claims can be surgically implanted wherein the first member is attached to, by way of example, a first bone, and the second member is attached to, by way of example, a second bone. The function of the implantable device acts directly upon the body joint.

The distracting devices and systems described herein can also produce compression, in embodiments. For example, to protect or unload a medial cruciate ligament tear, hinges described herein can be used to compress the medial compartment through a range of motion, such as a range of motion of a brace. Devices described herein can, in aspects, also produce a distracting force on the lateral side, thereby producing medial compression. These teachings can be applied to other ligaments or tendons in the knee, or in the ankle, toes, hip, back, neck, elbow, wrist, or other joints in the body.

In embodiments, a distracting or compression force is applied on only one side of a body joint. In other embodiments, the distracting or compression force is applied on two or more sides of a body joint.

Single-Upright Mechanism:

Extension-Flexion Stops: In addition to a controllable tensioning mechanism as described in embodiments 1-5, for example, extension-flexion stops may be used to prevent users from hyperextending or hyperflexing joints that may already be prone to injury, as well as simply limiting the degree of flexion or extension. In disclosed hinge assemblies herein, the brace hinge may comprise various methods of controlling the degree of extension and flexion of the joint. In one inventive embodiment, a slot that is radially oriented to the pivoting point of the hinge can be cut out of the hinge or created during fabrication of the joint. In other words, the hinge may comprise a slot, for example a slot that is radially-oriented to the pivoting point of the hinge. The degree of flexion and extension that the angle between the two frames of the brace can achieve during an articulated joint movement can be controlled by placing premade inserts at chosen locations in the radially oriented slot. The premade inserts can be fabricated with the material strength and shape to withstand articulated and intense joint movements without fracturing, bending, or slipping out of the slot. Either the side plates or hinge capsules will help secure the inserts into the hinge, without restricting smooth motion of the hinges/intermeshed teethed gears. This slot and inserts at various points in the brace allow for user customization of degree of flexion and extension allowed by the device at the hinge point.

Another variation of the extension-flexion stops is through a fabricating process, wherein inserts that may be placed in between the anterior and/or posterior of the upper and lower frame hinges can be used to control the degrees of flexion and extension in the joint at, for example, the hinge point. For example, the insert may be placed on the anterior side of the frame hinge between the gears in order to limit the degree of extension of the joint; alternatively, the inserts may be placed on the posterior side of the hinge to limit the degree of flexion of the joint.

The geometry of the teethed gears and hinge(s) may also be altered upon fabrication of the hinge grouping in order to limit the degrees of extension and flexion the joint can perform during use of the brace or a limit on the degrees of flexion and extension allowed by a hinge point on the device. For example, the geometry of one gear can be designed such that it does not fit within the opposing intermeshing gear at a certain degree of flexion or extension. The teethed gears/hinge preferably comprise a durable material that can resist the tendency for movement during extension or flexion of the joint.

Tubes: In another embodiment, the hinge assemblies comprise a tube or tubes through the geared components in the brace, and/or the brace frame, and comprise a tube or tubes within the support structure. The tubes may be integrated partially or completely within the frame, or may be external to the frame. The tube(s) in the brace components may be balanced to offer sufficient strength while minimizing the bulk and weight of the component. Materials can be chosen to allow for smaller or larger sized brace components. The tubes may be located anywhere within the frame of the brace and may orient the bands in a plurality of ways depending on a user's need, treatment, preference, comfort, injury, performance requirement, etc.

Tensioning elements can be located at different positions within the brace-above and/or below the hinge, and the hinge can draw lace or wire over the hinge causing the tensioning elements to elongate. The tension in the system would be modulated in a similar way, and the tension adjustment mechanism can be placed at various locations on the brace.

Another feature includes using tensioning elements that have a distinct ending point that limits the degree of flexion based on the length of the tensioning element and the length of the component, by limiting the amount of band drawn over a section of the hinge that acts as a cam, which generates a mechanical advantage as it draws the tensioning element(s) apart from its anchored ends. For example, in embodiment one, the bands are fixed at both ends; in embodiment two and four, infra, for example, the band(s) are fixed at the distal end only and tension is adjustable at the proximal end; and in embodiment three, infra, the band(s) are fixed at both ends, but are adjustable for tension. The shape of the cam can be modified to increase or decrease the elongation of on the tensioning element and therefore affect the torque generated.

The tension, or counter-force, in the hinge assembly may be adjusted by increasing the number of tensioning elements to increase the tension, and/or by using tensioning elements of more stiffness for a higher tension. In an embodiment, the knee brace is manufactured for a specific tension (low, medium, and high). In another embodiment (e.g., the second through fifth hinge embodiment, infra), the tension is adjustable by deactivating a hinge mechanism to allow the tensioning element(s) to stretch, or by activating the mechanism to block the tensioning element from stretching on one or both ends, thus increasing the tension in the band(s).

In another embodiment, comprising multiple bands, the elements can be mixed or combined with different strengths and sizes based on the user's preferences or needs, and the different elements can be engaged at different degrees of flexion. For example, one band could be engaged from 5-20 degrees of flexion, by way of example only, at which point another band would engage to increase the resistance.

The bands can be secured through a number of methods, including the use of clamps or pins or anchors through the tensioning element or through which the tensioning element may be engaged, and hole(s) in the brace may comprise components to prevent the band ends from slipping out of hole(s) while the brace is under tension. Other band geometries can be used, such as circular bands that hook into the top and bottom components of the brace.

The distal and proximal hinge are preferentially fabricated as a continuous material with the vertical supports, or alternatively are secured to the brace frame by bolts, rivets, pins, screws or another similar attachment mechanism. A brace support may be of plastic or carbon fiber and could be shaped to include the tensioning element supports and the gearing mechanism. An unloading brace can be made through any a combination of 3D printing, injection molding, water-jetting, casting, extruding, pultruding, or other similar ways. This brace can use multiple injection-molded components that connect together and house tubes, tensioning elements, and/or wires on, or partially or completely within, the components. These components may be connected to metal frame parts that generally shape around the leg or other limb. This version of the brace may be an alternate version of the 3D-printed version as a lower-cost or higher-volume production alternative.

The hinge components on the lateral and/or medial side of the knee can be spaced snugly to keep a narrow profile. If multiple elastic materials are drawn across the hinge, they can be oriented vertically or horizontally to the desired dimensions and/or tension of the brace. The components can be symmetric or shaped to contour the leg.

The hinge that connects the top and bottom components of the brace can, in aspects, be a U-shaped joint or another component that will offer lateral stability to the brace. These can be threaded or designed in a way to minimize the size and profile, such as using E-clips (circlips) or pressing the components in place.

Additional Applications

The hinge and tensioning assemblies described herein may be applied to other human joints, including but not limited to the ankle, shoulder, hip, elbow, and wrist joints. These embodiments of the present invention may include a support of one part of the joint being operatively connected to a support of another part of the same joint. This connection may comprise a tensioning element, which may or may not be adjustable, so that the brace may apply force in a direction favorable for rehabilitation or support of a joint.

For example, in an embodiment, an ankle brace may comprise an ankle cuff and a lower portion that connects to a region or regions of the foot. The ankle cuff may be connected to the lower portion of the ankle brace by one or more materials and/or adjustable tensioning elements that will apply force to desirable locations of the ankle and foot in order to provide the ankle with more support.

In another embodiment, the brace may comprise a portion that can be secured on one end to the hip of a user and to the leg of the user of the other end. By connecting these two ends of the brace with a tensioning element, the ball and socket joint of the hip may be adjusted to better align the femur and pelvis in a way that is physically preferable for the patient.

Any additional embodiments of this brace, as they are applied to other joints, may employ a variety of optionally adjustable tensioning elements, such as combinations of tensioning elements in series or parallel, and the strength of the tensioning elements may be adjusted depending on the type of joint and treatment needed per user. These additional embodiments may also employ the adjustable tensioning mechanisms, infra, in order to allow for dynamic use of the brace.

Tension Adjustment and Engage/Disengage Features

Another feature of the brace design taught herein is that in embodiments two through five, infra, the user can either fully or partially disengage the tension mechanism. The tension engagement-disengagement feature allows the user to increase the tension in the hinge assembly to provide more stability and off-loading of their weight from their knee, such as when climbing stairs, and then to turn off the mechanism or decrease tension when it is no longer needed, such as at the top of the stairs, so that the user can more easily walk or jog with a fuller range of motion. The current invention allows for this adjustment in real-time or near-real-time and while the user is wearing the brace.

Non-Limiting Embodiment 1—Fixed Tension

Hinge Assembly 1: In a first embodiment, the pivoting hinge assembly comprises two opposing, facing subunits, with a proximal (top) and distal (bottom) short end, and an anterior (front) and posterior (rear) side. Each subunit houses one gear that intermeshes with an opposing gear during articulated joint movement, e.g. a proximal and distal gear; at least one tensioning element extending between the subunits on the anterior side of the gears and fixedly connected on the band's ends to the posterior side of the subunits; and a connector on the medial and lateral side pinning the subunits together while allowing the gears to rotate. Tension may vary in the hinge depending on the strength of the tensioning element provided in the hinge assembly; this may be decided at the time of fabrication of the brace. Alternatively, the hinge may freely pivot without teethed gears.

Hinge Assembly—Non-Limiting Embodiment 2—Adjustable Tension—via Handle and Slider Hinge Assembly 2: Various embodiments of the present disclosure further comprise a second embodiment of a hinge assembly for use in a brace as disclosed herein, or other knee brace for treating a medical condition that requires unloading of a joint. The hinge assembly of embodiment 2 is similar to embodiment 1, but with the addition of a handle or knob attached to a mechanism that enables the user to adjust the tension on one end of the tensioning element(s) in real-time or near-real-time and in aspects while the user is wearing the brace by pulling the handle or knob one direction, thereby increasing tension, and then decreasing or releasing tension by moving in another direction.

In one embodiment, the tensioning element(s) proximal end is attached to a slide member that moves vertically (e.g., proximally-distally or distally-proximally) to, in aspects, pull the band taut to increase its tension. For example, when a user moves a handle or other mechanism that is located on the outside portion of the hinge, above the knee (or in aspects below or beside the knee), it moves backward-posteriorly. This handle movement forces a connecting slide member to move up-proximally, thus stretching the proximal end of the tensioning element(s). Thus, in an embodiment, the user can increase the stability and/or stiffness and/or tension of the brace/hinge/tensioning element by moving the hinge handle backwards, then moving it forward-anteriorly to release or decrease the tension and make the brace more flexible, which may comprise a fuller range of motion. In other aspects, the handle may slide front to back, back to front, or diagonally. In aspects, the user can increase stability and/or stiffness and/or tension of the brace/hinge/tensioning element by moving the hinge handle forwards, upwards, downwards, sideways, or diagonally, and then releasing or decreasing tension by moving the handle in an opposite or different direction.

Hinge Assembly—Non-Limiting Embodiment 3—Adjustable Tension via Ratchet-Pawl

Hinge Assembly 3: In another embodiment, each subunit houses one gear that intermeshes with an opposing gear during articulated joint movement, e.g. a proximal and distal gear; and at least one tensioning element extending between the subunits on a side of the gears (or over or under the gears) and fixedly connected on the tensioning element's ends to the posterior side of the subunits. In aspects, a core bracket member completely or partially covers the tensioning element between the subunits' open space to protect the element(s), and to pin the gears together while continuing to allow them to move relative to one another.

This embodiment may further comprise a rotatable or linear ratchet-pawl member on the upper and/or lower frame of the brace to vary tension in the band or bands. The user can rotate the knob or slide a lever to different positions to pull the tensioning element(s) tighter while reducing their effective length; this may be accomplished by winding a part of the tensioning element, for example a wire, around a coil as the member is rotated. For example, rotating the ratchet-pawl members clockwise increases the tension in the hinge assembly, making it less flexible, off-loading more of the user's weight from the knee joint, and providing more stability. The user can then release the ratchet-pawl members by pulling up or pushing down on a knob or a deactivation lever that is co-located with the member (or turning the knob in an opposite or different direction or rotation); and/or, in turn, the user would then be able to rotate the knob in a second, opposite direction to relieve tension in the tensioning element stretched between the gears.

Hinge Assembly—Non-Limiting Embodiment 4—Adjustable Tension—Spooled Wire

Hinge Assembly 4: The various embodiments of the present disclosure may further comprise another embodiment of a hinge assembly for use in a knee brace as disclosed herein, or other brace for treating a medical condition that requires unloading of the joint. The embodiment comprises one or more strands of tensioning elements with the elements' respective ends fixed in the distal subunit. The element(s) endpoint on the proximal end is pulled on by a wire that encircles it.

In this embodiment, a rotatable knob is connected to a spool of wire, for example, that pulls on the proximal end of the tensioning element as the user rotates the knob (if the knob is on the proximal portion; if knob is on the distal portion, the distal end is pulled). In aspects, the knob is rotatable to fixed positions so that the user is able to adjust the tension in the tensioning element to a desired level, and release the tension by rotating the knob in a different or opposite direction. In aspects, more turns or longer turns on the knob will result in higher tension in the tensioning element, and more off-loading of forces on the user's knee joint.

Hinge Assembly—Non-Limiting Embodiment 5—Wire-linked Bands with Adjustable Tension Hinge Assembly 5: The various embodiments of the present disclosure further comprise another embodiment of a hinge assembly for use in a knee brace as disclosed herein, or other brace for treating a medical condition that requires unloading of a joint. This embodiment comprises one or more tensioning elements housed completely or partially within the frame of the brace in both the proximal and distal frame portions. The one or more tensioning elements are further connected to each other by a wire that stretches over the gear assembly, and one or both bands are connected to an adjustable tensioning mechanisms using another wire(s).

In this embodiment, equal tension should be applied to the one or more bands in the hinge assembly, and tension is generated within the frame of the brace to generate resistance to flexion. The adjustable tension mechanisms of embodiments, 2, 3, and 4, for example, as explained supra, are connected to at least one of the bands either directly or indirectly.

Method of Use—Non-Limiting Embodiments 1-5

In various embodiments of the present disclosure, the amount of weight unloading (or resistance or tension generated in the brace) can readily be tailored to a user based on their size, weight, injury, therapeutic needs, and/or desired athletic performance. Braces as described herein are capable of being lightweight, robust, of a narrow side profile, and well-fitting to users. Unlike braces in the prior art, those disclosed herein can be narrow and lightweight so as to be worn under clothing, which is usually not possible for athletic performance braces. For these reasons, the brace can be ideal for a range of injury types and severity, as well as a way to enhance athletic performance.

The various embodiments of the knee brace of the present disclosure can be used, by way of non-limiting examples: prophylactically to prevent injury; to reduce joint pain (e.g., during normal activities, physical exercise, or athletic competition); to rehabilitate existing injuries; post-operatively (high tension braces to immobilize the joint to a comfortable level); as extension assist devices for medical conditions such as osteoarthritis, with some stability support for proper knee alignment through the range of motion; to enhance athletic performance (e.g., by applying force as a knee joint extends to, for example, add explosiveness as an athlete jumps or starts running); and/or to prolong the life of a natural knee afflicted with osteoarthritis or other knee injury, or to prolong the life of a prosthetic joint, possibly in order to delay, prevent, or avoid knee surgery.

Likewise, the knee brace and/or hinge assemblies disclosed herein are able to: reduce the weight, forces, and/or pressure on a knee joint when a user is load bearing on their legs, such as standing. And/or, the knee brace and hinge assemblies are able to provide knee extension assistance when walking, bending, moving from sitting to standing, exercising, etc.; therefore, the user has to exert less physical effort to move their knee between flexion and extension.

In an embodiment, the method of use for reducing load bearing on the knee joint comprises the steps of: attaching a knee brace of, for example, one of the embodiments listed above to a user's knee, comprising laying the inside surface of the brace vertical support comprising the upper and lower portions against a user's leg; and closing the brace straps or other way of connecting the brace to the user, such as multiple straps around the user's femur and multiple straps around the user's tibia; and, load bearing on the user's knee joint, wherein the load and/or pressure on the knee joint is reduced to the extent that the user experiences a reduction in pain or an improvement in movement as compared to load bearing without the knee brace.

A method of use further or alternatively comprises extension assistance, comprising the steps of the following when the user flexes a knee joint: stretching and generating a counter or restoring force at the hinge tensioning element to propel the hinge back from a bent, flexed position to a straight, extended position; wherein the brace reduces the amount of force required to be exerted by the user's leg and knee and associated muscles to return the brace hinge (and knee joint) to an extended position from a bent position; and wherein the load and/or pressure on the user's knee joint is reduced to the extent that the user experiences a reduction in pain or improved movement as compared to flexing and extending the user's knee without a knee brace.

In yet another embodiment, a method of use comprises: having a user activate a hinge mechanism to pull one end (or both ends) of the tensioning element(s) more taut to increase tension and stability in the hinge assembly and knee brace, and then to deactivate the mechanism when it is no longer needed (or decrease tension). Various embodiments of the hinge mechanism comprise: a handle or engaging piece attached to a sliding lever, wherein moving the handle backwards (or forwards, upwards, downwards, or diagonally) causes the sliding lever to move in manner to pull one end (or both ends) of the tensioning element(s) taut (e.g., see second embodiment, supra); a rotatable or linear ratchet-pawl mechanism on one or both ends of the hinge (or above or below or beside the hinge) that a user can move clockwise or counterclockwise (or up or down) to impinge the tensioning element(s) and increase tension therein, then release (see, e.g., third embodiment); and a rotatable knob connected to an internally housed spool of, in aspects, rigid line or wire that is attached to a folded tensioning element, wherein turning the knob pulls on the tensioning element to increase the band's tension, and rotating the knob in the opposite direction releases or decreases the tension (see, e.g., fourth embodiment).

Methods of Generating Tension

Tension may be generated in a hinge by drawing a tensioning element, which may be an elastic, semi-rigid, or rigid component or components, across a hinge or lever arm that results in the elongation of the tensioning element. The tension generated as a function of degrees of flexion or per degree of flexion may vary throughout the range of flexion to generate different force profiles and resulting device performance. This may be achieved by variation in hinge geometry such as including a cam on the hinge or the pathway of the band or tensioning element, or gears of different radii. The geometries of cams or gears of variable radii may be tailored to achieve a desirable unloading profile depending on the user's needs. For example, a cam or gear may have an exaggerated bulge as opposed to a flat shape, which will generate an increasing amount of tension per degree of flexion as the user proceeds through a range of motion because the tensioning element or wire connected to the tensioning element will travel further over the cam. The force profile may be, by way of example only, linear, logarithmic, or exponential. Cams or gears of different geometries may be built into the brace or rapidly engaged, disengaged, or interchanged using levers or switches to achieve different force profiles and performance as needed.

Overall tension or the adjustment of the force unloaded per degree of flexion could be changed by limiting the movement of elastic material or anchoring at various fractions of the length, therefore limiting the region of elongation. The radius of the gear, thickness of the band, length of the band, multiple of bands, and other attributes of the brace can be adapted to the user's knees.

Bands or tensioning elements may comprise smaller individual bands or bundles that may be activated in parallel to achieve varying degrees of tension and unloading.

The activation of one or more tensioning elements may or may not be accomplished electronically via piezoelectric sensors or other electronic signals activated manually or automatically.

This system of generating tension can be applied to other joints of the body that may or may not include geared or ungeared hinges. For example, flexion and extension in the wrist may be assisted in a similar manner by connecting an upper and lower component above and below the wrist joint that are operatively connected using a tensioning element that may or may not be adjusted with a rotational dial such as a BOA or other mechanism.

Tension may be applied across various mechanical joints within the device, such as ball-and-socket, condyloid, gliding, and saddle joints. It may be applied in one or multiple axes, and can be engaged or disengaged as a whole, or in one axis depending on user need. The joints alone or in combination with the tensioning mechanism may limit or allow movement in one or multiple axes to reproduce, augment or limit the natural movement of the anatomical joint to which the device is applied.

Generating Tension Across a Single Upright Hinge

A single upright knee brace may include a tensioning system. A single upright knee brace may provide valgus or varus unloading support by utilizing material flexibility, rigidity, and strength characteristics to apply forces in the desired location(s). For example, a brace designed to treat varus to relieve medial compartment osteoarthritis may apply a lateral force in the center of the brace. The curvature of the frame away from the leg will apply a medial force above and below the user's knee, resulting in a corrective or distractive force that will reduce pressure in the medial compartment. Alternatively, a valgus brace may pull the joint laterally to unload the medial compartment while applying a lateral force above and below the joint. These forces may occur in conjunction with a force that pushes or pulls the joint apart, allowing for less contact pressure between joint components, such as the femur and tibia in the tibiofemoral joint.

The amount of force and support may be based on user inputs such as self-reported pain levels and measured or estimated inputs such as Q-angle and radiographic information.

In embodiments, the single upright brace frame is designed to translate force optimally without the bulk and weight of a double upright brace. For example, in aspects, the proximal and distal posterior support is required and an anterior support is required above and below the knee. In aspects, the brace can be worn on the medial or lateral side of the leg. In aspects, the brace can treat varus or valgus from either the inside or outside of the leg. For the unloading variant, the tensioning element may be drawn over the hinge and tensioned using one or more elastic bands and a tension-locking mechanism such as a BOA dial or other tension-adjusting mechanism that may be placed on the upper or lower portion of the frame. The brace may be contoured around the leg and patella to prevent or minimize rotation around the leg and migration down the leg. An alternative version of this brace has a fixed tensioning element. A strapping system may be incorporated into the brace frame that provides or supports the varus or valgus correction, prevents rotation around the leg, prevents migration down the leg, and eliminates undesired torques that the joint may be subjected to.

A variant of the knee brace may use the same brace and tensioning system to generate tension or resistance in the opposite direction, as in it resists extension. The device may be used to assist users by increasing range of motion.

Bolt Action or Lever Mechanism as an Adjustable Tensioning System

An alternative method of tensioning a band or multiple bands is with a system of one or more levers. A lever or levers may be pulled in one direction to increase tension and hooked onto a latch to maintain tension. The lever may be unlatched by pulling in one direction and moved by pulling in the other direction. The lever may be located on the upper or lower member of the knee brace and may be on one or both sides of the knee brace. The lever is operatively connected to the tensioning element. The lever may involve lace or wire to connect to one or more tensioning elements and one or more pulleys may be involved.

Cam Mechanism as an Adjustable Tensioning System

The tension in the brace may also be adapted to individual users by adding a cam-like feature wherein the tensioning element is drawn over a part causing the band or lace or wire to travel a greater distance as a result of the cam than without it. The result of the implementation of this mechanism may be an increased amount of tension per degree of flexion and may be tailored to individual users. The cam system may be adjusted on inputs from radiographic information and assessed need for correction and support. The cam modifications may be fully or partially automated and incorporated into the design process of the brace, or modified after the brace has been fabricated. The cams themselves may be adjustable and are interchangeable, in aspects.

Internalized Band as an Adjustable Tensioning System

An alternative system involves a mechanism where tensioning elements are integrated within the brace frame rather than drawn over the hinge. These bands may occur as one or more and may be found in either or both the upper and lower members. The brace frame may involve a tensioning system that controls the amount of torque around the hinge.

Method of Joint Distraction to Generate Space in Between the Joint

In a knee brace as described herein, distraction can be accomplished between the tibia and femur in a number of ways. In aspects, one way is in a geared or ungeared hinge, the radius of the gear can vary with degrees of flexion. One example is as the degree of flexion increases, the distance between joint centers may also increase, thereby providing a separation force across the joint. A user may be assessed to determine the optimal variation in the gear radii. In embodiments, for a double upright knee brace, the gear radius on one side of the brace can differ from the gear radius on the other side. This method of joint distraction is also applicable for a single upright knee brace. This mechanism may or may not include a slot design that allows for limited direction of travel based on gear radius. The slot controls the direction of the distraction. A center cap encases the hinge and contains slots to support the hinge mechanism. These slots can be oriented in an optimal manner for the user's needs and may be linear or curvilinear/nonlinear.

The distraction hinge may or may not be associated with a tensioning system. When the brace does not include a tensioning system, tension may be applied to the center pin through the hinge to maintain close gear contact. A mechanism of restricting motion of the center pin through the slot such as a leaf spring or a clip or clips may or may not be implemented.

The vertical member may be elongated to increase distraction. In embodiments, this can be accomplished in a number of ways such as providing a telescoping vertical member where the distal end of a member and the proximal end of a member are increased or decreased in distance based on the user's needs. Another method according to the present invention is the use of a spiral rotating knob that can push the distal and proximal members apart. The result is an increased distance between the connection points of the upper portion and lower portion of the knee brace to the user's leg. This can also be accomplished electronically by a motor tensioning the system, or with a gear or gears and rack, driven by a knob that may be ratcheting. The telescoping mechanisms can be located on the upper or lower or both portions of the knee brace. The system may rely on one or more pulleys.

Pivoting External Loops as a Mechanism to Secure Straps or Semi-Rigid Supports

A pivoting external loop or pivoting D-ring is included wherein the D-ring component includes a slot for passage or connection to a strap or support which may be comprised of Velcro or another material. The pivoting member involves a partially approximately round component that allows for the position of the strap relative to the frame to pivot. The pivoting member either straps into or is embodied within the brace frame. The component may or may not be 3D printed and may or may not be printed within the existing structure. Alternatively, the D-ring may be continuously adhered directly to the brace frame and may be cast, injection molded, or 3D printed. The range of motion or positioning of individual D-rings can be customized or altered based on the user's needs or the position on the brace frame.

Method of Detailed Characterization of Knee for Brace Design

A user's knees may be characterized by qualitative assessment through various activities such as squatting or knee extension. Input to the brace design may be extracted from radiographs, x-rays, MRIs, 3D scans, or data collected from sensors. Additional inputs may include patient-reported pain score, Q-angle, measurement of adipose tissue, and radiographic information. Radiographic information may or may not be used to estimate the firm and soft tissue in the user's knees. Aspects of this process may be automated.

The radius of the gear, thickness of the tensioning element(s), length of the tensioning element(s), multiple of tensioning element(s), number of tensioning element(s), and other attributes of the brace can be adapted to the user's knees. The process of assessing the patient as a method of creating inputs for the desired brace design can be partially or fully automated. For example, the Q angle may be estimated by a knee scan or x-ray, and a patient may report a certain level of pain in one compartment of the knee, such as the medial tibiofemoral compartment. The design of the brace may be automated to modify the amount of force applied to the opposing joint compartment (lateral) and other points on the leg to alleviate pressure in the injured joint compartment. The device may engage or disengage and alter tension in response to EMG or other biometric data related to the user's movement and support or limit movement in a desired manner.

From inputs such as biometric or radiographic data, the nature of the user's injury can be characterized and elements such as Q-angle correction, amount of unloading force based on degree of flexion, torque profile for medial and lateral sides, and tension levels for medial and lateral sides may be determined. The nature of the injury for the knee's envelope of motion may be understood. This may be modeled based on a scan based on the range of motion of the joint.

Adjusting Joint Geometry/Gait Via Tensioning

The user's injury will be analyzed with data including but not limited to MRI scans, x-rays, qualitative information such as self-reported pain and region of joint, and biometric data such as BMI and Q-angle. The patient may be recorded and gait modeled as well. This information can be used through manual or automated processes to restore and improve joint geometry to reduce pain or enhance performance. The brace may automatically or partially automatically adjust to the user's needs.

Joint rotation and/or joint alignment may be influenced by varying tension across the hinge. Tension may be applied to one or both sides of the brace. If tension is applied on both sides of the brace, the tension may be equal or dissimilar to generate the desired torque profile for each side. The torque profile is designed based on the needs of the user's joint to restore or improve joint alignment and function. The size and geometry of the brace frame may be modified to flex the appropriate amount. Material choice such as plastic, metal, carbon fiber, or a combination thereof may be used to achieve the desired flexibility to support the goal of improving joint function. The amount of flexibility of the brace frame will be tailored to the needs of the user for fit and to assist with generating an unloading force. For example, a brace with a bowed frame with the center of the bow placed at the center of the side of the knee condyle will generate an unloading force in the compartment opposite of the side where the bow is contacting the knee joint.

The user's gait may be influenced to a healthier gait by generating an appropriate amount of tension. The information described in the previous section and sections herein can improve gait, alter walking pattern to reduce pain, increase stability, and reduce long-term wear on the joint.

Method of Securing Wire or Lace to Tensioning Element

The tensioning element within a brace may be either 3D printed based on an elastic polymer or elastic material such as rubber, or may be cast or injection molded from a similar material. The wire or lace or cable may be secured to the tensioning element by looping through a series of holes and knotting or tying off the lace or wire. Alternatively, the lace or wire may be knotted or placed within a hardened material such as an epoxy that is then integrated or bonded or attached to the elastic material. The region where the wire or lace attaches to the tensioning element may use a metal component that may be crimped or compressed to secure the wire or lace within the tensioning element or elements. A part to increase surface area may be tethered or attached to the wire or lace and inserted within the tensioning element to prevent the band or wire or lace from detaching. The system may be secured further by coating with a glue or hardening compound such as an epoxy to minimize the risk of detachment. The opposite end of the tensioning element may be anchored in position due to a change in geometry that would prevent the tensioning element from moving or dislocating. Alternatively, this part may be pinned, glued, pinched, or screwed in place to prevent dislocation.

Method of Securing Knee Orthosis to Ankle Orthosis

The braces described herein may involve connection to an ankle foot orthosis wherein the tensioning system for the knee brace may additionally be connected to the ankle orthosis. Alternatively, the position support or tension in the ankle orthosis may be controlled by a separate tensioning system on the knee portion of the orthosis or ankle portion of the orthosis. The knee orthosis may be operatively connected to the ankle orthosis by a plastic, metal, carbon fiber, or other structural material. The geometry of the orthosis may be based on a 3D scan from the patient's leg and/or foot. Corrections to the gait and points of support and pressure may also be based on information from the 3D scan. In aspects, for unloading Knee Ankle Foot Orthoses (KAFOs), the amount of loading assistance will be pre-set in the brace according to the size and strength of the tensioning elements based on the user's needs. When tensioning elements and a tension locking mechanism are used, the tensioning elements may be drawn over the hinge or hinges, or attached to a wire or wires that are drawn over or through the hinge. The devices may interface mechanically or structurally to generate dynamic and synergistic forces throughout the lower limb through a range of motion or gait. For example, the tensioning elements of the knee brace and ankle orthosis may be mechanically integrated so that as the knee reaches about 60° of extension, the ankle orthosis support provides dorsiflexion support. Additionally, the tensioning elements may communicate remotely via Bluetooth, WiFi, or other signaling means to work synergistically to support or direct gait.

Method of Making

The various embodiments of the present disclosure may use traditional manufacturing processes for knee braces, and/or 3D printing to produce prototypes or final versions of the components (such as the gears and/or subunits of the hinge assembly) to then be injection molded, extruded, pultruded, or may be entirely 3D modeled and/or printed, from parts to the entire brace. In an embodiment, the brace is sized to fit the user and can be form fitted to the user.

Unique fabrication methods and materials make this form fitting brace possible. For example, two-dimensional or three-dimensional pictures, videos, or scans can be used to generate a model or a final product (or parts) that contours or fits the user's leg or other joint, and the properties of the material, in aspects, will have an amount of flexibility in the lateral direction, for example, and less flexibility in the direction of extension or extension depending on the purpose of the brace.

The fabrication technique of the braces herein allows the braces to include unexpected advantages not included in the prior art, including manufacturing and performance advantages. Therefore, an improved fitting brace that is higher functioning, safer, more effective, and more comfortable is possible by the invention taught herein. The fabrication methods and materials can also assist in keeping production costs lower than the prior art.

In addition to injection molding and 3D printing the frame of the brace, the brace may also be constructed entirely of a material that allows for it to be thermal molded around a specific patient's leg post-fabrication, or similarly, sections of the brace may be made of a material that can be thermal molded to produce a specific force on a patient's leg at a given location, for example providing varus/valgus support. Additionally, it may be desirable for the padding on the brace, whether it is 3D printed as an extension of the frame of the brace or separately adhered using another method, to be thermal moldable to a patient's leg. The benefit of this would be that the padding could possibly be switched out or modified (if it is not continuous with the brace) as the patient desires, without the need for refabrication of the brace. Pultrusion and extrusion techniques are also envisioned.

Unloading and Torque

The knee brace vertical support of the present disclosure differs from the prior art, including in that it unloads a significant amount of force that is normally applied within the knee. The basis for patellofemoral pain is that a large amount of force is distributed over a small area. Injuries to this surface can result in severe pain and defects/injuries, and the cartilage surface can degrade, thus exposing bone and nerves in an accelerated time frame. The tension-generating, unloading mechanisms in the present disclosure's knee brace address distributing forces experienced in the knee to other body parts and dampening the impact that would be painful to a joint afflicted with osteoarthritis. The effect of action of the brace is equivalent to a significant reduction of weight by the user; the most fundamental treatment for sufferers of osteoarthritis is weight loss.

The amount of force unloaded in a knee brace of the present disclosure is characterized by its relative torque measured about the hinge (e.g., in units of inch-pounds [in-lbs]), and the amount of weight unloaded or offset (in units of pounds [lbs]). For example, the general strength or tension of the knee brace of the present disclosure is generally broken down into three categories:

Low: below 3 lbs. unloaded
  Medium: range of 3-15 lbs. unloaded
  High: above 15 lbs. unloaded The reduced force in an OA afflicted knee joint via use of the present brace and/or hinge assemblies allows for deeper flexion of the user's knee that would normally be prohibited due to pain. This deeper flexion engages the user's quadriceps to an extent that would normally be avoided by the user due to debilitating pain, thus facilitating a user gaining strength through exercise. Additionally, the resistance generated by the brace can strengthen supporting soft tissue during exercise, for example the hamstring can be strengthened via a brace vertical support and/or hinge assembly as disclosed herein that resists tension on the quadriceps.

Use of Condyle Spacers

The knee brace described herein may include condyle pads that may or may not be increased or decreased in width depending on the severity of the varus or valgus alignment of the knee. Condyle spacers are used to shift the Q angle of the knee, or the angle of the femur relative to the tibia. A method of correlating the Q angle to the degree of varus and valgus has been developed, and this may automatically generate inputs into a digital model of the brace to be fabricated in order to sufficiently compensate for the medical condition.

In embodiments of the present invention, the condyle portions of the brace can be adjusted in a telescoping manner to increase or decrease pressure on one side of the joint. For example, a certified prosthetist orthotist may be required to evaluate the Q angle of a user's knee, and then assign a specific number of condyle spacers that should be inserted within the adjustable condyle hinge region of the brace. The condyle spacers may be inserted by removing the screws and caps of the condyle hinge and inserting the desired number of condyle spacers into the condyle region of the brace, and replacing the cap and screws after adjustment. This embodiment poses the advantage of being able to readjust or add to the width of the condyle region if a progressive treatment path is desired for a patient. Another variation involves sliding spacers of different sizes in a tongue-and-groove that may lock or snap into position, and allow for rapid adjustment of the condyle spacing.

In additional embodiments of the present invention, a predetermined width of the condyle spacing region may be desired. In this embodiment, the width of the condyle region would not be expected to change throughout the course of treatment for the patient, and the width of the hinge would be determined during fabrication of the brace, such that the condyle hinge cap of the brace may have a thickness that is determined based on the desired correction of the Q angle of the knee.

Use of Sensors and Motors

The knee brace described herein may have sensors in place that measure and monitor the position of the brace relative to either or both the leg and another part of the brace. This position data can provide velocity and acceleration data that are used as inputs to a processor or monitoring system for the brace. Velocity and acceleration may be measured by positioning sensors or other sensors. This data may provide the basis for adjustment by a motor system to either assist or support a joint by increasing or decreasing tension.

Sensors may also be used to measure and monitor the amount of tension present in the brace or joint assistive device, and the amount of unloading force applied at the joint, including a variable amount that changes as the joint is extended or flexed. The analog value of the tension present at the joint may be converted to a digital signal in a variety of ways, such that the user of the brace has knowledge of how much tension is present in the brace at any given time, or as a change in tension is recognized by the sensor.

The sensor(s) may be fabricated on or within the brace. The sensor(s) may output a digital or electronic signal, and they may connect to one or more LED lights that may indicate the information about the brace such as the amount of force or tension in the brace at any given moment in time. Additionally, the sensor(s) may be connected to one or more lights that light up different colors depending on the amount of force or tension in the brace; for example, the light may light up one color for maximum force and another color for a lighter amount of force.

The brace motor, sensor, and control processor system may also include a potentiometer, gear box of gearing system, and one or more servo arms or levers. The motor is operatively connected to the tensioning element through a system of gears or another method such as a screw, which can gather or release tension, based on inputs from sensors managed by a controller or processor.

The sensor(s) may also be connected to a screen on the brace that communicates information such as force generated within the brace, or weight unloaded by the brace, such as in a relevant unit value for the user. The sensor(s) may also be synced to an application on a smart device, such as a smartphone, tablet, or computer, that provides the user with feedback about the amount of force being applied by the brace, and/or the direction the joint is being overloaded in or the direction the joint is being flexed or extended. Data from these sensors may be logged and analyzed, used to identify patterns, and may be used as inputs to a controller that determines how motors should function in an assistive or supportive manner.

The sensors may also be connected to the tensioning mechanism; for example, using feedback from the sensors, the tensioning mechanism may loosen or tighten the tension in the tensioning elements based on the feedback it receives and a preset level of desired tension, as decided by the user. This would eliminate the need for the user to adjust the amount of tension present in the brace during use of the brace. In an embodiment, a user would set certain parameters and, based on feedback from the sensors as processed by a processor, the brace would be able to automatically adjust tension using motors, hydraulics, or microdrives, for example, or to alert the user to change resistance. In aspects, the sensors and related processor may be connected to a server or the internet, which may inform the processor of whether to adjust tension, or it may provide advice to the user about tension recommendations or other information related to treatment or use of the brace. Similarly, the sensors in adjunct with a processor may inform a doctor of the tension in the knee brace or other information from the brace and use of the brace so that a treating physician, for example, could diagnose the patient, monitor the patient, monitor the treatment, provide treatment options, warn the user of problems, adjust tension, determine when there is improper use of the brace, determine if an injury has occurred, monitor performance, etc. Thus, sensors used with a processor may be able to provide more automatic use and adjustment of the brace, including using software implemented predefined parameters to adjust tension or otherwise monitor and control use of the knee brace. The tension may also be adjusted electronically in the absence of sensors, where one button or input increases tension, and another button or input may decrease tension. This can be done with a toggle switch, rotatable knob, or touch button(s).

Electromyography (EMG) sensors may be used to activate a joint assistance mechanism to unload weight in the joint for which the device is applied. This may be done with or without other sensors and with or without motors. The degree of assistance may be modified and calibrated to the needs of the user.

BRIEF DESCRIPTION OF THE DRAWINGS

The above and other features, aspects, and advantages of the present invention will become better understood with regard to the following description, appended claims, and accompanying drawings where:

FIGS. 22A-22B illustrate a cam and slot eccentric distraction hinge, according to embodiments of the present invention.

FIGS. 23A-23B illustrate the loss of synchronicity of the cam and slot eccentric distraction hinge of FIGS. 22A-22B.

FIGS. 28A-28C illustrate a compound distraction hinge, according to embodiments of the present invention.

FIGS. 36A-36B illustrate a compact compound distraction hinge rotating about the second axis.

FIGS. 38A-38B illustrate side views of the compact compound distraction hinge of FIG. 37.

FIGS. 59A-59C show another embodiment of a hinged distraction mechanism suitable for a JDO.

DETAILED DESCRIPTION

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Embodiments comprising various features may also consist of or consist essentially of those various features. Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention.

All references cited in this specification are hereby incorporated by reference in their entireties.

Figure 20:
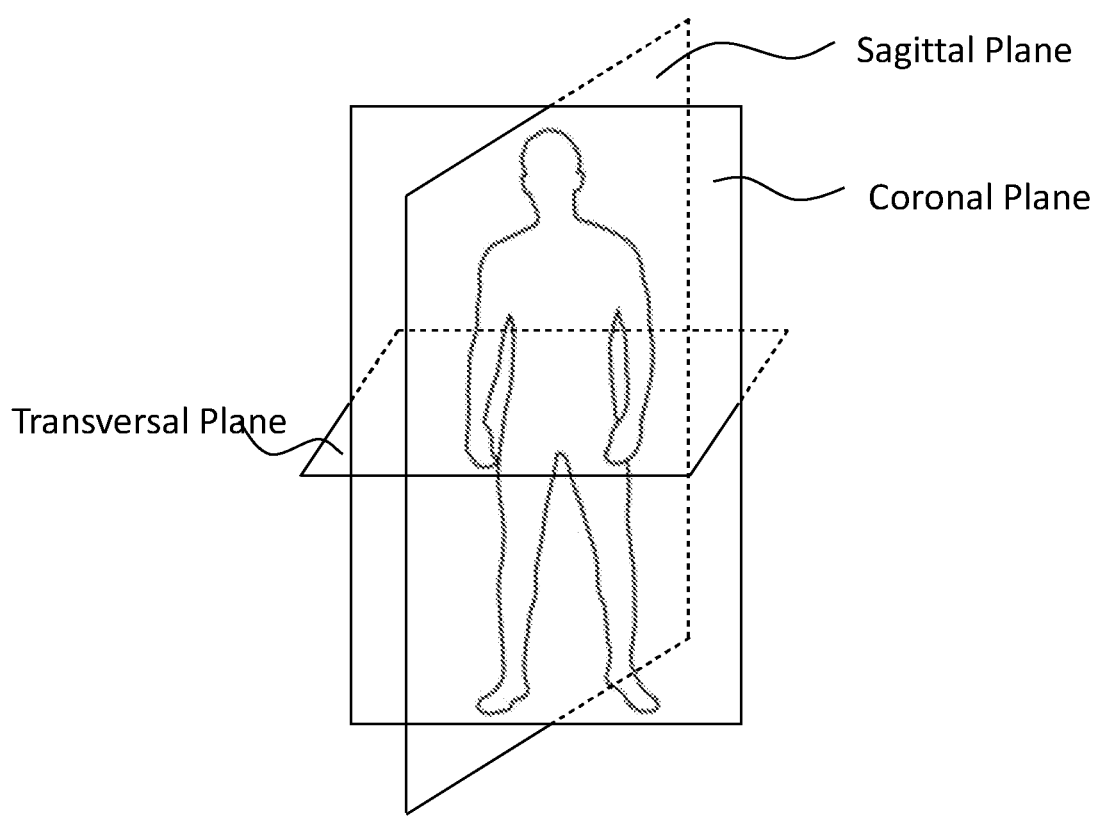
FIG. 20 is an illustration of the three planes of the human body.
Figure 21B:
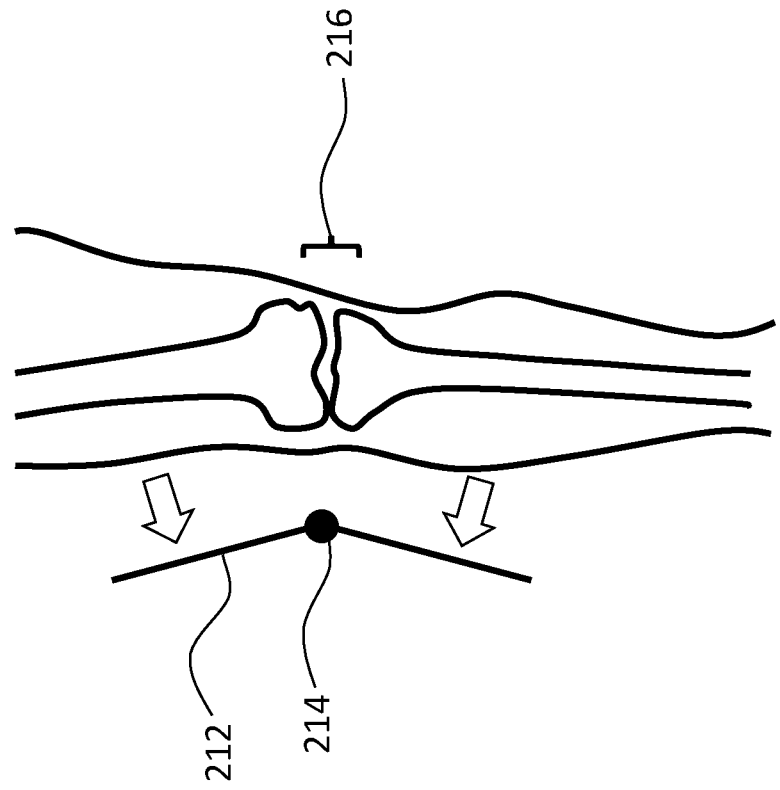
FIGS. 21A-21B illustrate the medial unloading of a traditional three point bending knee brace.
Figure 21A:
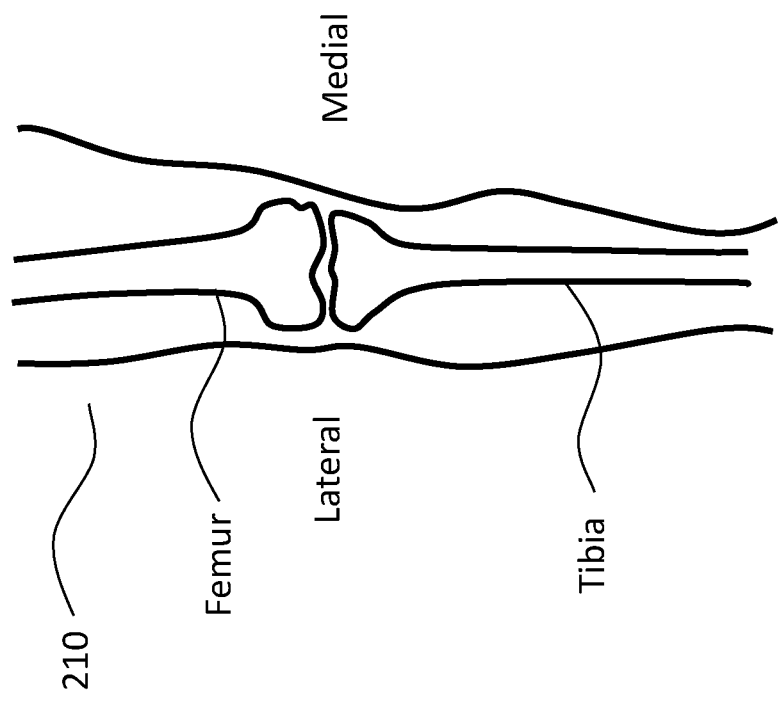

FIG. 20 is a schematic of a human body showing the orientation of the coronal (or frontal) plane, the transversal, and sagittal planes. Distraction of a joint can be defined as a physical separation of the bones that comprise the joint. In the case of distraction of the knee joint, for example, the physical separation of the tibia and the femur occurs predominantly in the sagittal plane. Distraction of a ball and socket joint, such as the shoulder joint, is more complicated and may occur in several planes at the same time. Flexion is the movement of the body limb away from the straightened position. Extension is the movement of the body limb towards the straightened position. The flexion angle is the included angle between the limbs (or body parts) connected by the joint. For the knee joint, 0 degrees (or substantially 0 degrees) of flexion is the same as a fully extended (a straight) leg.

It is desirable to create a brace for distracting a joint that is able to be varied in correlation to the degree of flexion of the joint. For example, the forces that compress the knee vary as a person walks. A gait analysis study by Kutzner, et al. [https://www.ncbi.nlm.nih.gov/pmc/articles/PMC3847086/] show that the maximum force on the leg is 2.66 times their body weight and occurs when the gait stance is between toe off and mid-swing which corresponds to 30-60 degrees of knee flexion. In preferable embodiments, an unloading mechanism would be able to vary its unloading value based on the amount of flexion of the joint. For a knee joint, in cases, the maximum unloading is needed at roughly 45 degrees of flexion.

The current invention describes a mechanism that is able to distract a joint without, in aspects, the need for applying a moment of rotation across the joint and that is, in aspects, able to vary the amount of distraction that is synchronized with the amount of flexion of the joint. The present invention can be applied to orthotics designed for the distraction needs of various joints of the body.

Several means for generating a joint distraction force are described herein.

Figure 4:
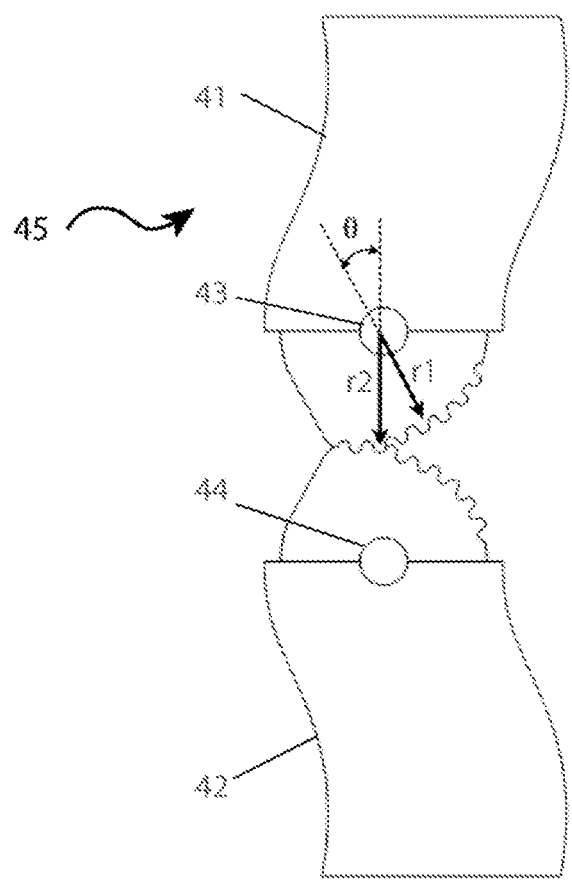
FIG. 4 is an illustration of a variable radius distracting hinge, according to embodiments of the present invention.

One example is shown in FIG. 4, which shows a variable radius mechanism (45). As the upper arm (41) rotates about the pivot point (43), the gear teeth engage and the lower arm (42) rotates a corresponding amount about pivot point (44). Herein, an "upper arm," "first member," and "top frame element" can be used interchangeably. Likewise, a "lower arm," "second member," "lower frame element," and "bottom frame element" can be used interchangeably herein. In this embodiment, the distance between the points of rotation (43) and (44) changes from 2 times $r_2$ to 2 times $r_1$ as the upper arm rotates through the angle $\Theta$ shown. In order to accommodate the difference in distance between the points of rotation at least one corresponding slot is required. The slot can be located in the hinge cap (not shown) that connects the two arms. Alternatively, at least one of the holes (43) and (44) can be replaced with a slot. If the gear teeth of the arms (41) and (42) are always intermeshed, the amount of distraction can be synchronized with the degree of rotation of the arms (that is, with the flexion of the body parts of the corresponding body joint).

In another example of a means for generating joint distraction, FIG. 22A shows a similar mechanism. An upper arm (221) and a lower arm (223) contact each other via variable radiused surfaces (222) and (224), respectively. A hinge cap (225) connects the upper and lower arms. Pins (226) and (229) ride in slots (227) and (228). As the arms rotate as shown in FIG. 22B, the slots allow the pins to move closer together as the distance between the pins decreases. The mechanism shown in FIG. 22A and FIG. 22B are similar in function to the variable radiused gears shown in FIG. 4. Unlike the mechanism in FIG. 4, there are no gear teeth shown on the surfaces (222) and (224). As shown, friction between the surfaces is needed to keep the distraction distance synchronized with the flexion of the body joint.

Pins as used herein can mean any one or more of the following: a bossed feature, a bolt, a screw, or any other structure that would fit or ride in the grooved features described herein for purposes of constraining, guiding, or otherwise defining a movement of elements of the current invention.

In an orthotic brace positioned across a joint, as the limb moves from flexion to extension (that is, as the limb is straightened) the center points of rotation of the two arms distract—move farther apart. This distraction unloads the joint.

As mentioned above, the forces loaded on the knee are at a maximum when the knee is in flexion from 30 to 60 degrees when walking. In aspects, it is advantageous that the distraction of the hinge mechanism is maximized when the orthosis is flexed in this range. A variable radiused mechanism according to the current invention, such as that shown in FIG. 4 and FIG. 22A, has the benefit that the increase in radius can be synchronized with the degree of flexion of the limb.

Using slots in the hinge cap (or the arms) to accommodate the distraction distance created by the variable radii can allow the distraction mechanism to get out of sync. FIG. 23A shows the two arms of a distraction mechanism in a partially flexed position similar to that shown in FIG. 22B. However, due to the slots, it is possible to pull the arms (221) and (223) apart which causes the surfaces (222) and (224) to lose contact. In a geared mechanism such as shown in FIG. 4, the teeth of the two opposing surfaces may not be engaged which would allow the upper arm (221) to move independently of the lower arm (223)—thereby allowing the mechanism to get out of sync with the joint flexion as shown in FIG. 23B. Mechanisms which use a friction between the surfaces to drive simultaneous motions such as the cams shown in FIG. 22A are even more prone to this problem.

Figure 25:
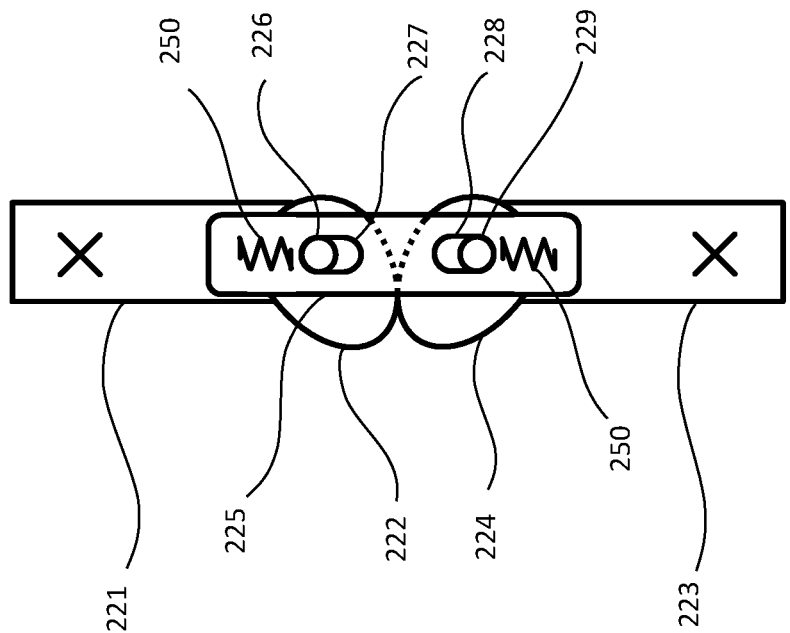
FIG. 25 illustrates an embodiment of compression elements to hold a cam and slot eccentric distraction hinge in synchronous movement, according to embodiments of the present invention.
Figure 24:
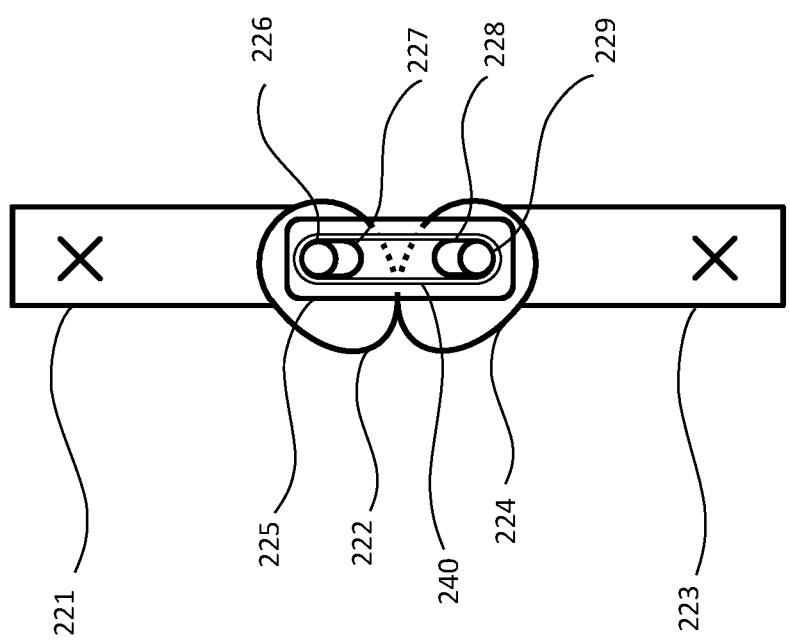
FIG. 24 illustrates an embodiment of a tensioning element to hold a cam and slot eccentric distraction hinge in synchronous movement, according to embodiments of the present invention.

According to the current invention, it is possible to use a tension element to connect the two pins (or their functional equivalent). The tension element exerts a force which pulls the two variable radiused surfaces together. In embodiments, the strength of the tension force needs to be less than the distraction force needed for the unloading of the joint yet greater than the force that could pull the surfaces out of synchronization. FIG. 24 shows another means for generating a joint distraction force, which is essentially the same mechanism of FIG. 22 with the addition of an elastic element (240) that applies a tension on the pins (226) and (229) to keep the surfaces (222) and (224) together. FIG. 25 shows another embodiment having a means for generating a distracting force, wherein springs (250) apply a compression force to the pins to keep the surfaces (222) and (224) together.

Figure 1:
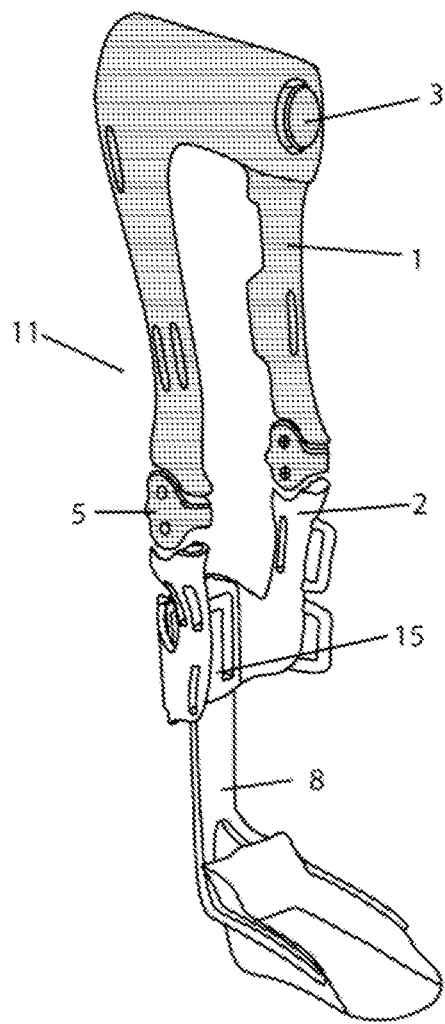
FIG. 1 is an illustration of a perspective view of a knee ankle foot orthosis (KAFO) in extended position, according to embodiments of the present invention.
Figure 2:
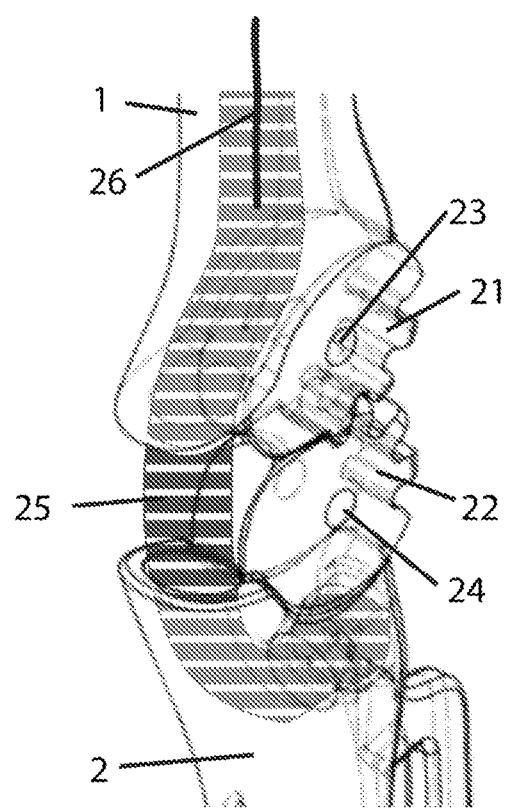
FIG. 2 is an illustration of a hinge assembly of a knee portion of a KAFO or HKAFO, according to embodiments of the present invention.
Figure 3:
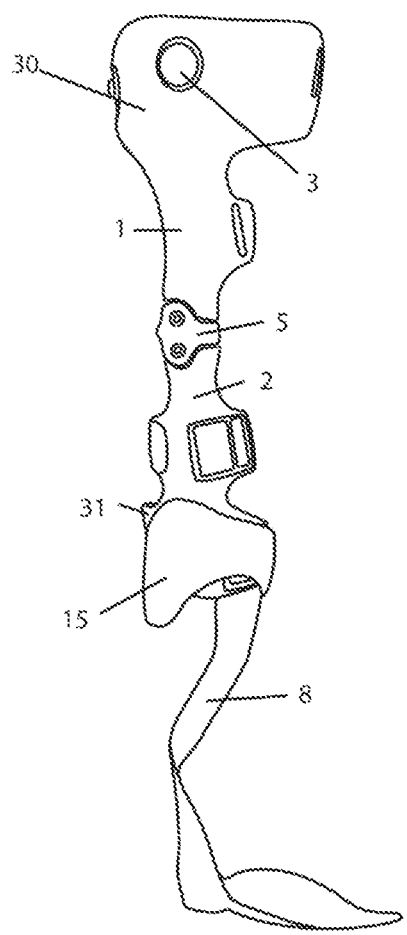
FIG. 3 is an illustration of a KAFO with a single upright knee orthotic, according to embodiments of the present invention.

Additional tension or compression elements such as shown in FIG. 24 and FIG. 25 may not be needed in the case of a hinge assembly such as that shown in FIG. 2, where the hinge assembly itself applies an unloading force using a tensioning element (25) that directs a force across, around, or between the elements connected by the hinge assembly. FIG. 2 is yet another means for generating a joint distracting force according to the present invention.

Figure 26A:
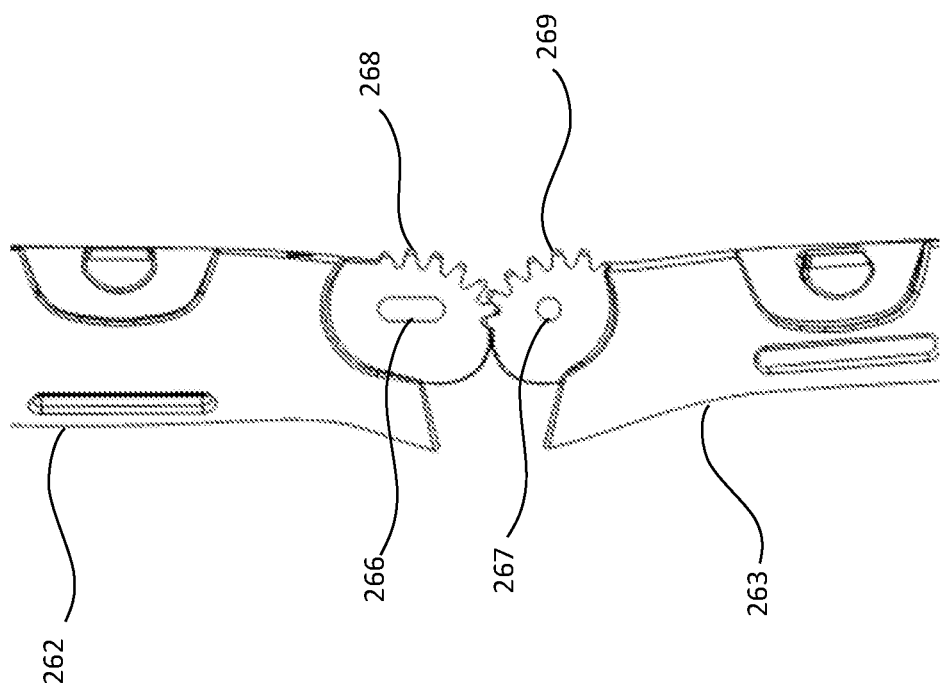
FIGS. 26A-26B illustrate a bicentric toothed eccentric distraction hinge, according to embodiments of the present invention.

In another embodiment of the present invention, a flexible yet substantially inelastic element (such as a cord, rope, chain, lace, braid, etc.) may encircle or partially encircle the surface elements to keep them engaged. FIG. 26 is yet another means for generating a joint distracting force according to the present invention. FIG. 26A shows a schematic of a distraction hinge disposed on one side of a knee brace. An upper arm (262) and lower arm (263) are connected by a hinge cap (265). Pins (264) allow the arms to pivot.

Figure 26B:
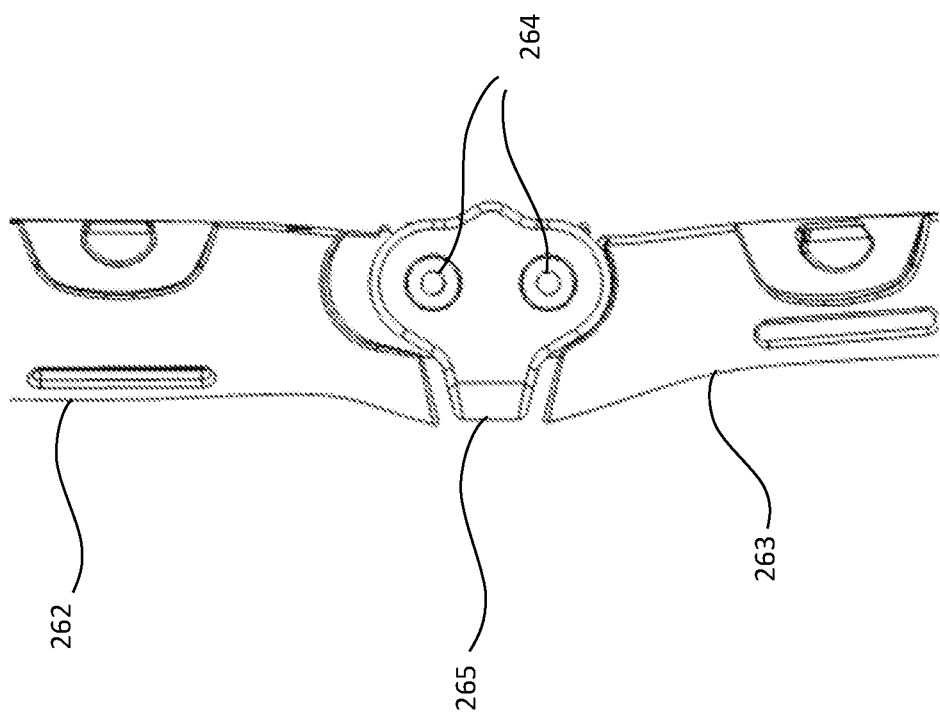

FIG. 26B shows the same mechanism with the hinge cap removed. Gear teeth are disposed along a variable radiused surface (268) and (269). The lower arm pivots about a circular hole (267) whereas the upper arm may pivot and slide along a slot (266). The slot allows the pivot points as defined by the pins (264) to move farther apart as the leg wearing the brace is extended thereby creating the intended distraction force.

Figure 27:
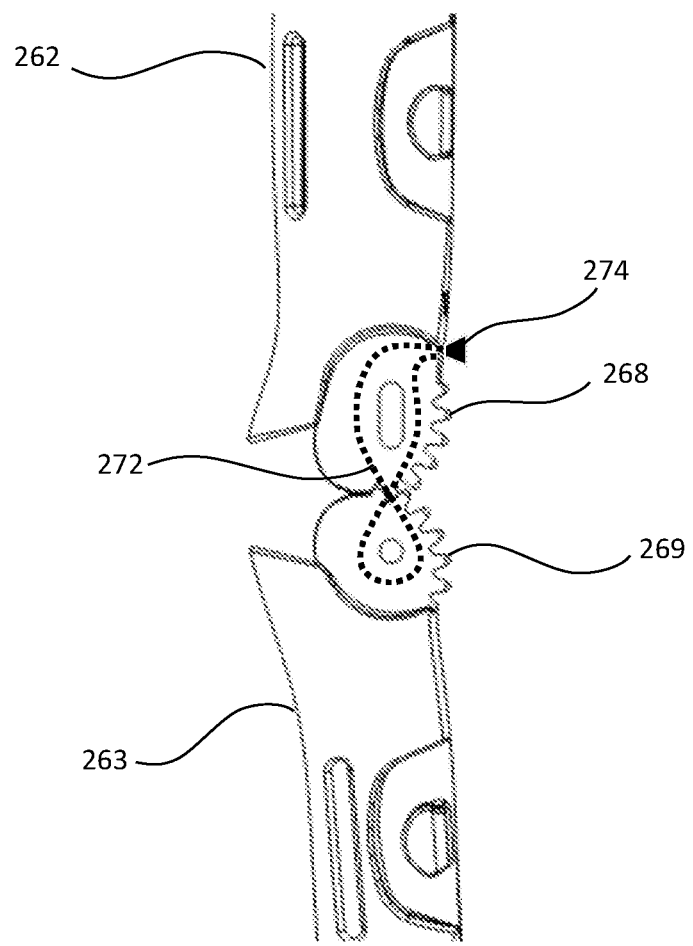
FIG. 27 illustrates the path of a flexible, substantially inelastic element needed to hold the hinge of FIGS. 26A-26B in synchronous movement, according to embodiments of the present invention.

FIG. 27 shows another means for generating a joint distracting force according to the present invention, wherein a path (272) of a cord that can hold the upper and lower arms in synchronous motion. The path criss-crosses at the junction of the two surfaces (268) and (269). A channel (not shown) prevents the cord from getting pinched between the surfaces. The path (272) shown only criss-crosses once, but it is possible to loop the cord multiple times around the path to create more criss-crossings. The ends of the cord are terminated at an element (274) such as, by way of example, a peg or anchor point. In aspects, turning the peg tightens the cord, drawing the two surfaces into engagement. This embodiment has the advantage that the force drawing the surfaces together is independent of the degree of flexure of the hinge (unlike the tension element shown in FIG. 24). Another advantage of this embodiment is that the maximum amount of distraction (the largest radius of the variable radiused surface) can be positioned at any degree of flexion. The criss-crossed cord holds the surfaces together and keeps the upper and lower arms synchronized no matter what the angle of maximum distraction is fabricated into the contacting surfaces.

Figure 5A:
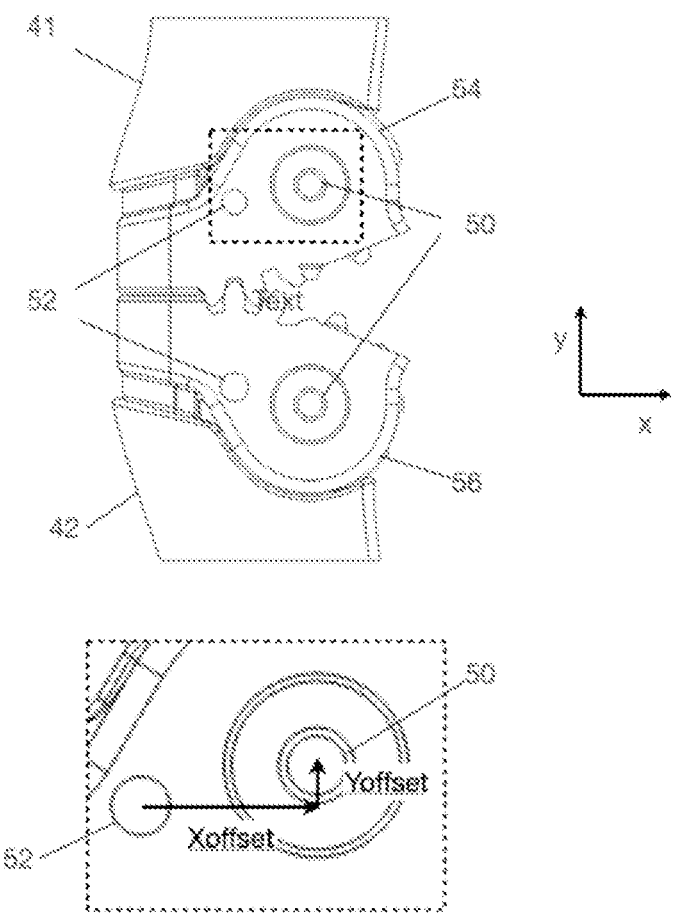
FIGS. 5A-5C are illustrations of a multi-axis distracting hinge, according to embodiments of the present invention.
Figure 5B:
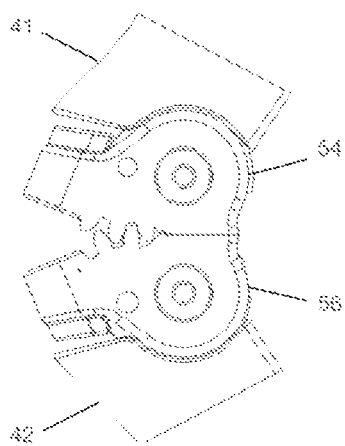
Figure 5C:
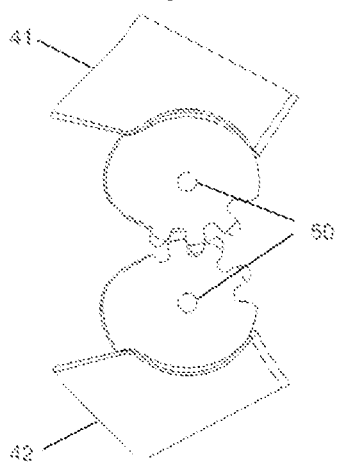
Figure 6A:
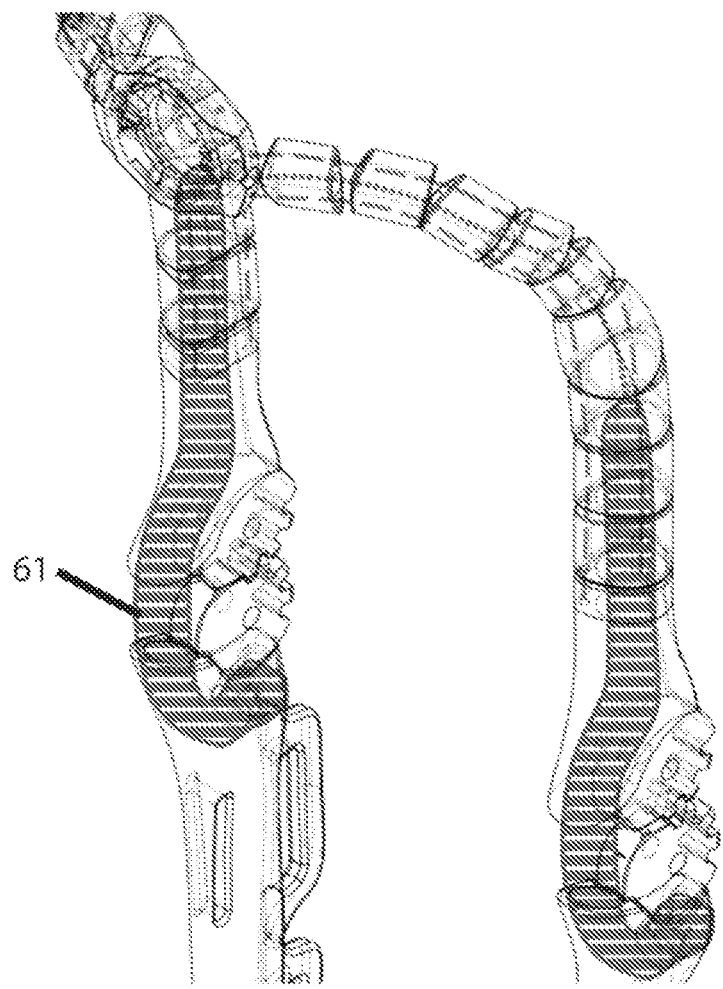
FIGS. 6A-6B are illustrations of a modular hinge and an adjustable tensioning system and exemplary components, according to embodiments of the present invention.
Figure 6B:
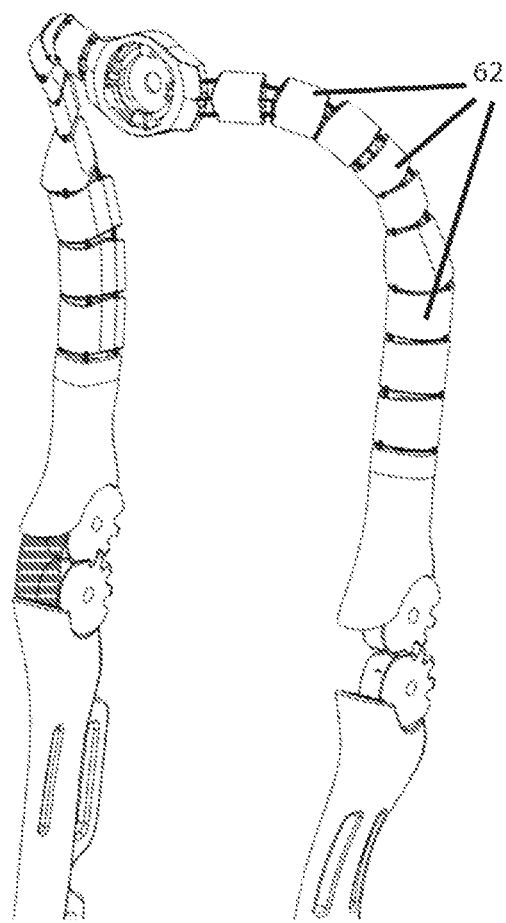
Figure 7:
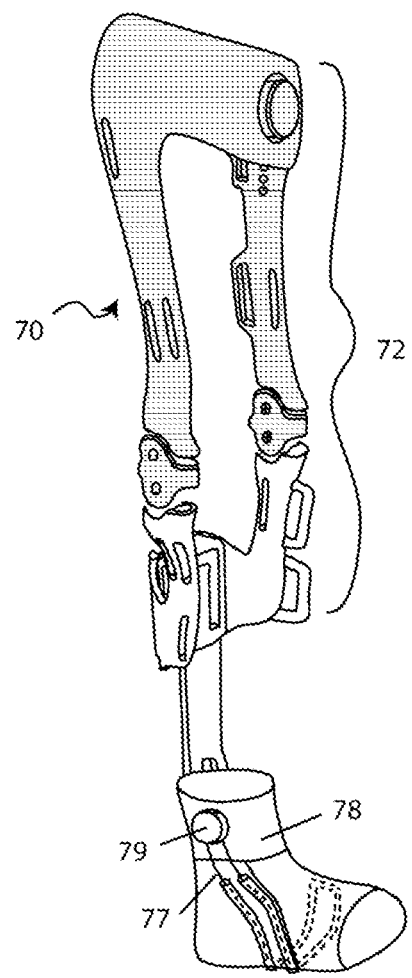
FIG. 7 is an illustration of a KAFO containing a multi-axis rotational control ankle foot orthosis (AFO), according to embodiments of the present invention.
Figure 8:
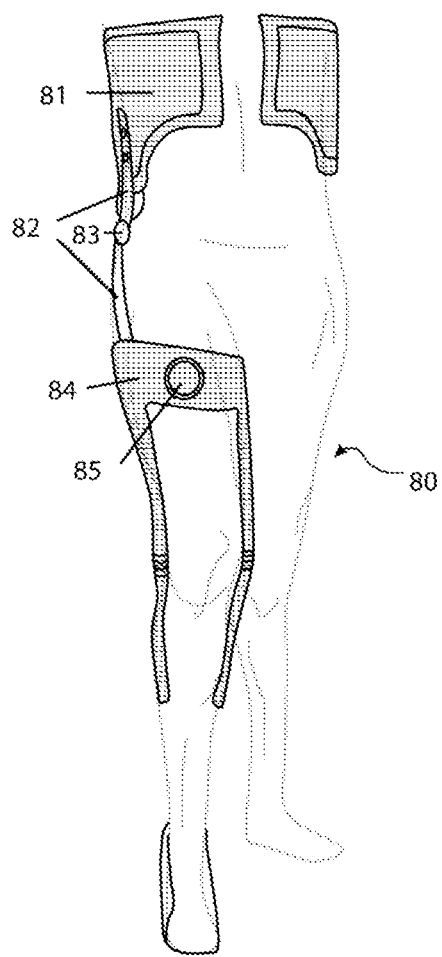
FIG. 8 is an illustration of a hip knee ankle foot orthosis (HKAFO) containing an adjustable tensioning system, according to embodiments of the present invention.
Figure 9:
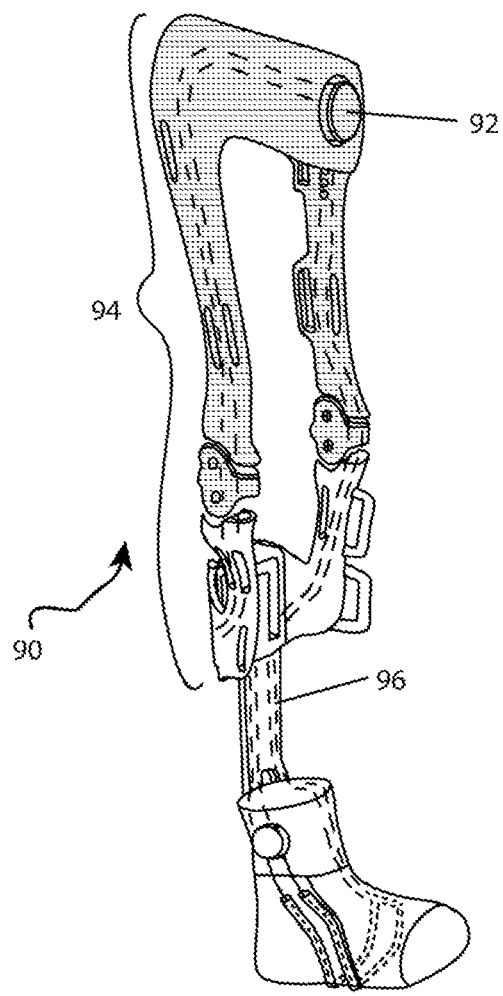
FIG. 9 is an illustration of a KAFO containing an integrated adjustable tensioning system that runs between the knee orthosis and AFO components, according to embodiments of the present invention.
Figure 10:
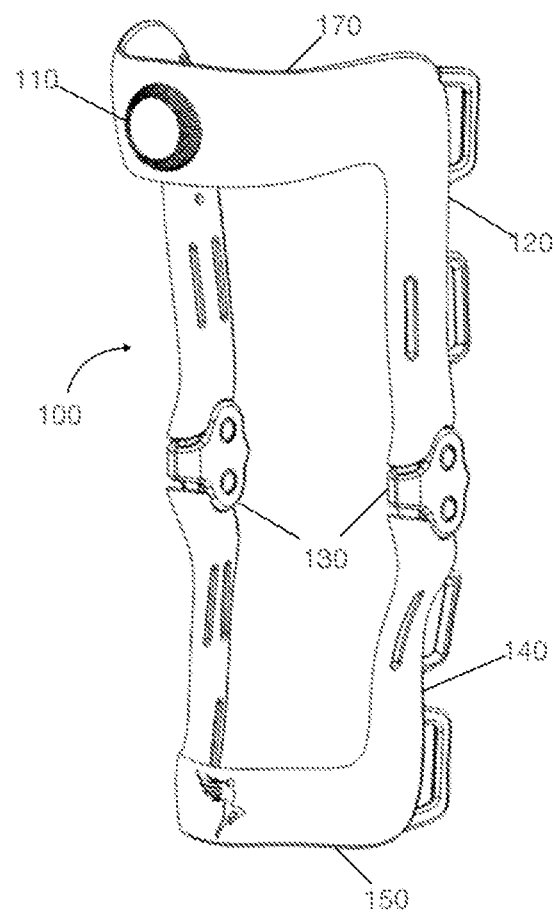
FIG. 10 is a depiction of an anterior view of an example of an adjustable tensioning unloading knee orthosis, according to embodiments of the present invention.
Figure 11:
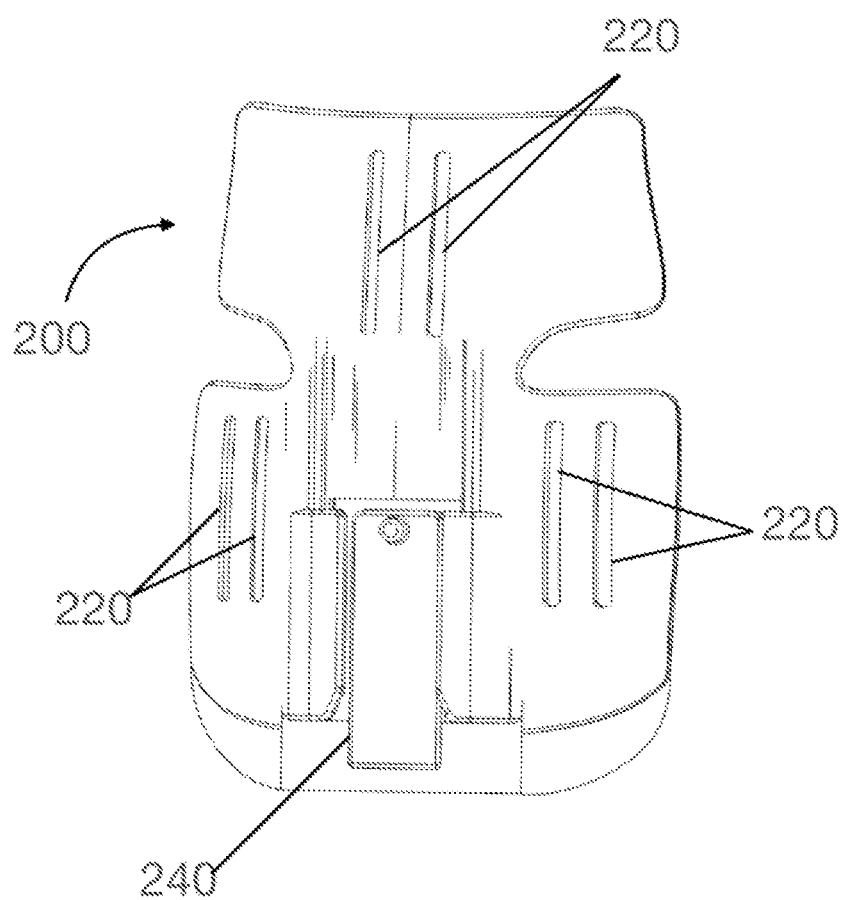
FIG. 11 illustrates an attachment mechanism(s) to combine the knee orthosis component with the ankle foot orthosis component, or a hip component with a knee orthosis component, according to embodiments of the present invention.
Figure 12:
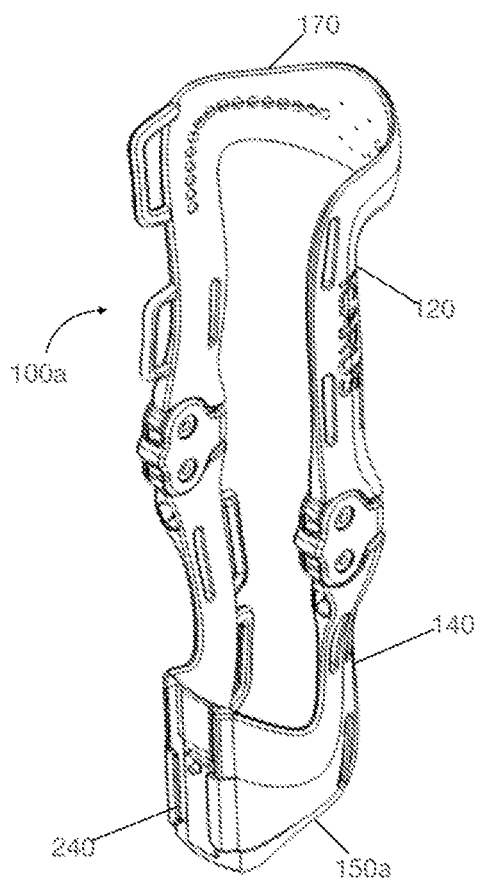
FIG. 12 illustrates an exemplary attachment mechanism(s) to combine a knee orthosis component with an ankle foot orthosis component, or a hip component with a knee orthosis component, according to embodiments of the present invention.
Figure 13A:
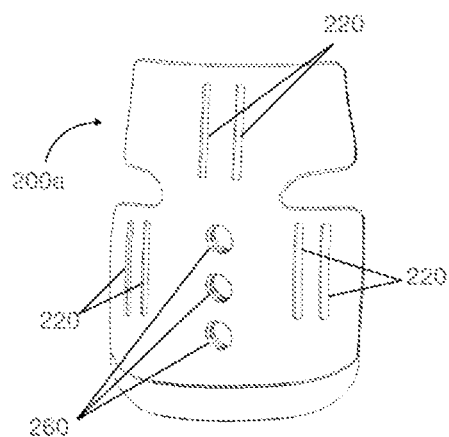
FIGS. 13A-13B illustrate exemplary attachment mechanism(s) to combine a knee orthosis component with an ankle foot orthosis component, or a hip component with a knee orthosis component, according to embodiments of the present invention.
Figure 13B:
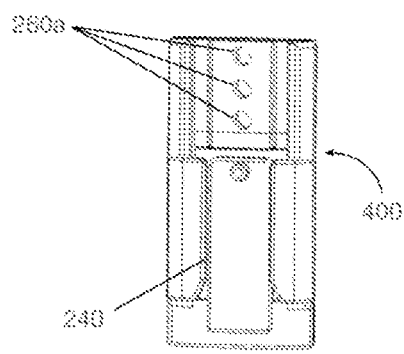
Figure 14:
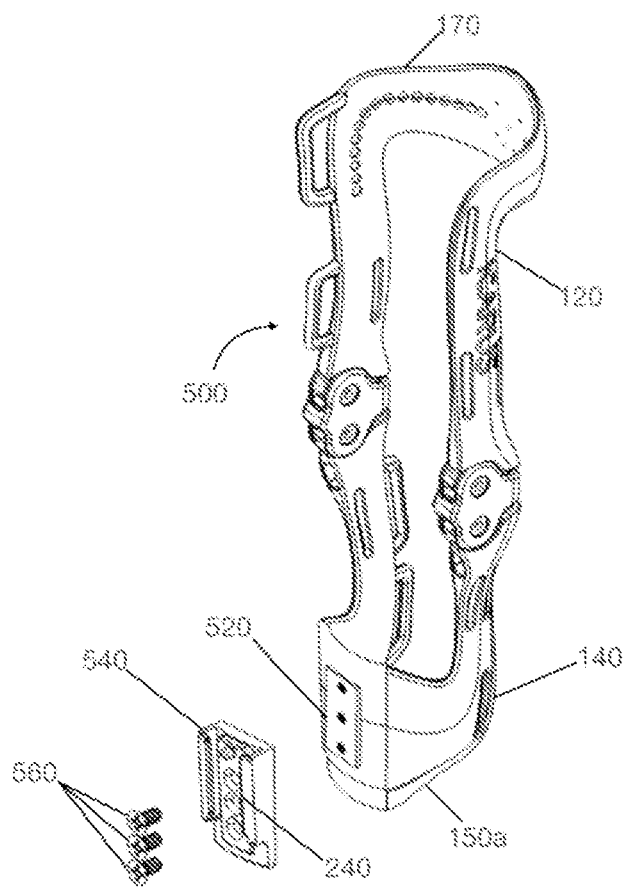
FIG. 14 illustrates exemplary attachment mechanism(s) to combine a knee orthosis component with an ankle foot orthosis component, or a hip component with a knee orthosis component, according to embodiments of the present invention.
Figure 15:
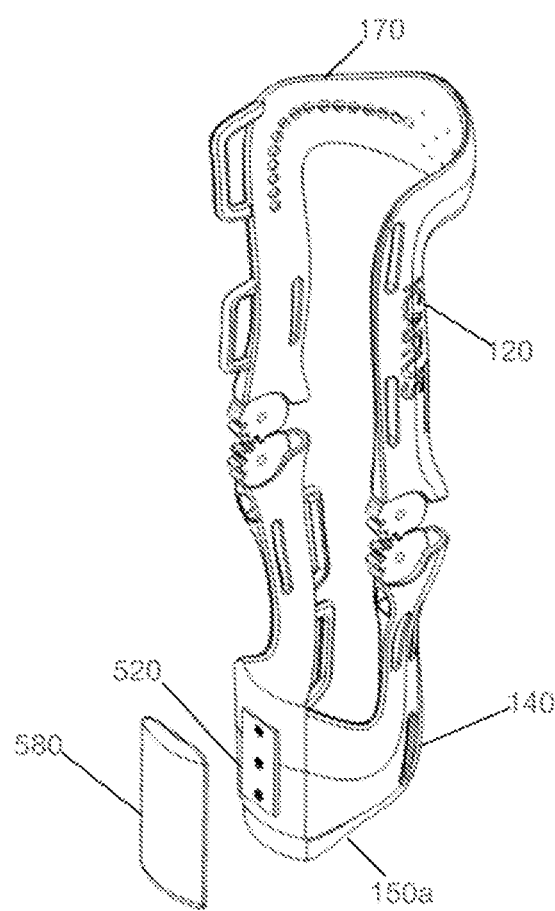
FIG. 15 illustrates exemplary attachment mechanism(s) to combine a knee orthosis component with an ankle foot orthosis component, or a hip component with a knee orthosis component, according to embodiments of the present invention.
Figure 16A:
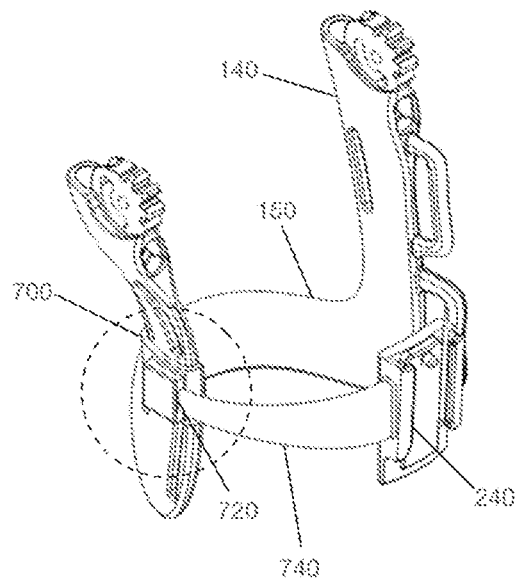
FIGS. 16A-16B illustrate exemplary attachment mechanism(s) to combine a knee orthosis component with an ankle foot orthosis component, or a hip component with a knee orthosis component, according to embodiments of the present invention.
Figure 16B:
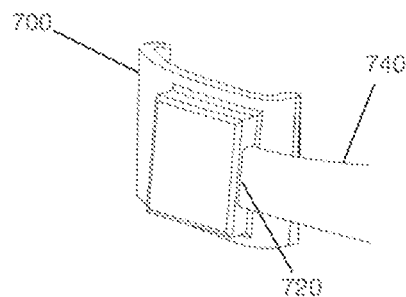
Figure 17A:
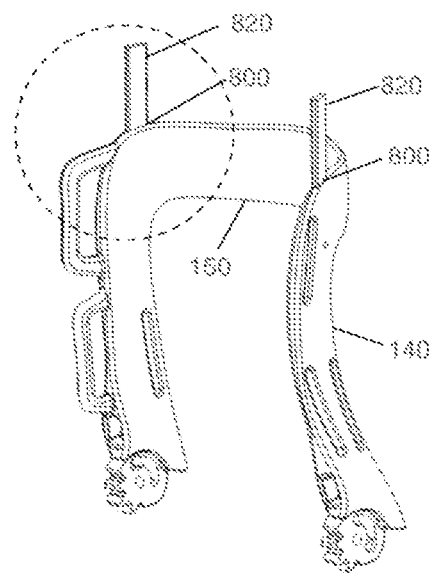
FIGS. 17A-17B illustrate exemplary attachment mechanism(s) to combine a knee orthosis component with an ankle foot orthosis component, or a hip component with a knee orthosis component, according to embodiments of the present invention.
Figure 17B:
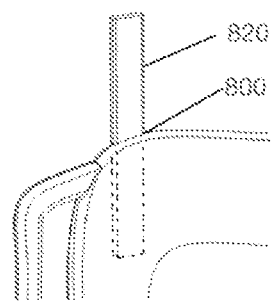
Figure 18:
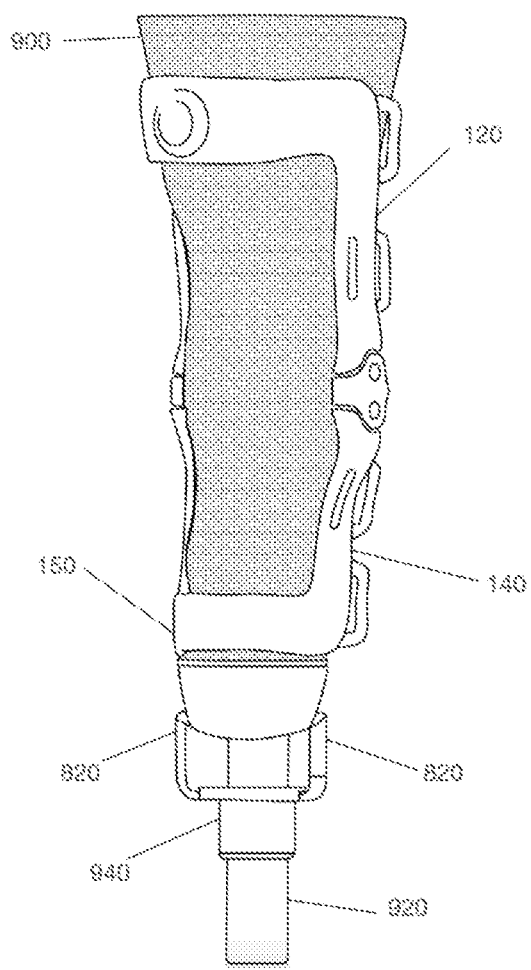
FIG. 18 illustrates exemplary attachment mechanism(s) to combine a knee orthosis component with a prosthesis, according to embodiments of the present invention.
Figure 19:
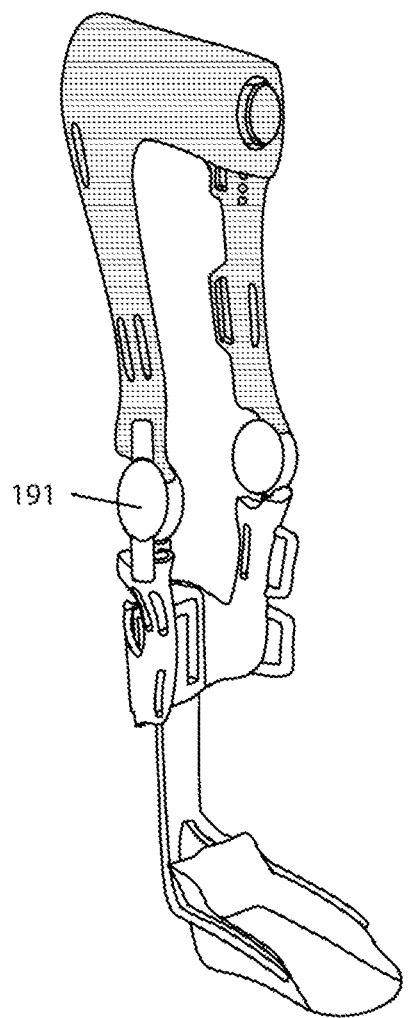
FIG. 19 is an illustration of an adjustable tensioning KAFO containing a drop lock mechanism, according to embodiments of the present invention.

FIGS. 5A-5C show another means for generating a joint distracting force according to the present invention, wherein the means of producing a distracting force is synchronized to the degree of flexion of the hinge. Instead of a single, variable radiused surface on each of the upper and lower arms, two different single radiused surfaces are provided for the upper and lower of the arms. The distraction occurs because of the offset of the centers of rotation of the two different surfaces.

In another embodiment showing a means for generating a joint distracting force according to the present invention, a distraction hinge can be accomplished with a compound hinge, wherein there is more than one axis of rotation of the hinge, and wherein the axes of rotation are not co-axial. FIG. 5A shows an example of a two-axis hinge. The hinge rotates about pivot point 50 from 120 to 30 degrees, by way of example. From 30 to 0 degrees the hinge rotates about pivot point 52. Because the two pivot points are not co-axial, there is a net vertical, y, and horizontal, x, distraction. In the example shown in FIG. 5B, the polycentric hinge elements 54, 56 and the upper and lower arms 41, 42, use geared teeth to keep the upper and lower arms in synchronous motion. The geared teeth pitch or module can be the same, as shown in FIG. 5A and FIG. 5C for the two pivot points, or they could be different.

Further, FIG. 5A shows the orientation of a multi-axis hinge at 0 degrees of flexion. The hinge elements 54 and 56 (as shown in FIG. 5A) are engaged and the upper and lower arms are rotating about the axes of rotation 52 (as shown in FIG. 5A). FIG. 5B shows the orientation of a multi-axis hinge at 45 degrees flexion. Both sets of gears, the hinge elements 54 and 56 (in FIG. 5B) and the upper and lower arms 41, 42 (in FIG. 5B) are engaged. FIG. 5C shows the same orientation as FIG. 5B with the hinge elements 54 and 56 removed for clarity. In FIG. 5C, the engaged gears of the upper and lower arms 41, 42 are shown. Increasing the angle of flexion now occurs around the pivot points 50.

In aspects, the total amount of distraction is determined by the formulii:

$$Dx = Xoffset*\cos(theta) - Yoffset*\sin(theta) - Xoffset$$

$$Dy = 2*[Yoffset*\sin(theta) + Yoffset*\cos(theta) - Yoffset]$$

Where Xoffset is the distance along the x-axis from the pivot point 50 to pivot point 52 (see FIG. 5A), Yoffset is the distance along the y-axis from pivot point 50 to pivot point 52 and theta is the angle at which the distraction begins. In FIGS. 5A-5C the distraction starts at 45 degrees of leg flexion, by way of example only.

Regarding the embodiment shown in FIGS. 5A-5C, in some orientations of flexion it is possible to draw the surfaces of the arms apart so that the gear teeth are not engaged. The upper arm can be rotated out of synchronization with the lower arm and then the gear teeth can be brought together again. In this manner, the inherent amount of distraction provided by the double gears will no longer be in sync with the flexion of the joint.

Tensioning or compression elements such as shown in FIG. 24 and FIG. 25 can be employed to keep the double gear surfaces engaged throughout the range of motion. Alternatively, a pin and slot mechanism can be used to prevent unwanted range of motions.

FIG. 28A shows another means for generating a joint distracting force according to the present invention, wherein a double geared distraction hinge similar to the mechanism shown in FIGS. 5A-5C provides a distraction force. A top frame element (280) and a bottom frame element (282) are connected together by an outer cap (285). Pins and slots are used to limit unwanted motion of the arms to prevent them from getting out of sync. In this particular embodiment, the pins and slots in FIGS. 28-30 are mirrored in the top and bottom frame elements. For clarity and to keep the labels clear in the figures, only the features of the bottom frame element are labeled and discussed, but the same explanation applies to the pin and slots in the upper frame elements. The bottom frame element (282) rotates with respect to the bottom inner frame cap (287) about pivot point (299). The bottom inner frame cap (287) rotates with respect to the outer cap (285) about pivot point (298).

A pin (283) which, in aspects, is secured to the bottom frame element (282) rides in a slot (284) in the outer cap. In embodiments, the flexion angle (180 degrees minus the included angle between the top and bottom frame element) is roughly 90 degrees. FIG. 28B shows the same mechanism with the outer cap removed to view the positions of the inner caps (286) and (287). There is a partial slot (288) in the inner caps. Finally, FIG. 28C shows the same mechanism with the inner caps removed to view the top and bottom frames. In this embodiment, there is a hole (289) in the bottom frame where the pin (283) is secured. In this embodiment, it is shown in FIG. 28C that the geared surfaces at the distal ends of the top and bottom frame element are (fully) engaged; the top and bottom frame elements cannot get out of sync.

Figure 29C:
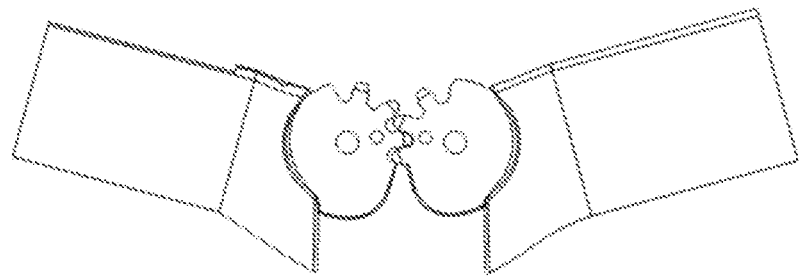
FIGS. 29A-29C illustrate the compound distraction hinge of FIGS. 28A-28C at the limit of rotation about one axis, according to embodiments of the present invention.
Figure 29B:
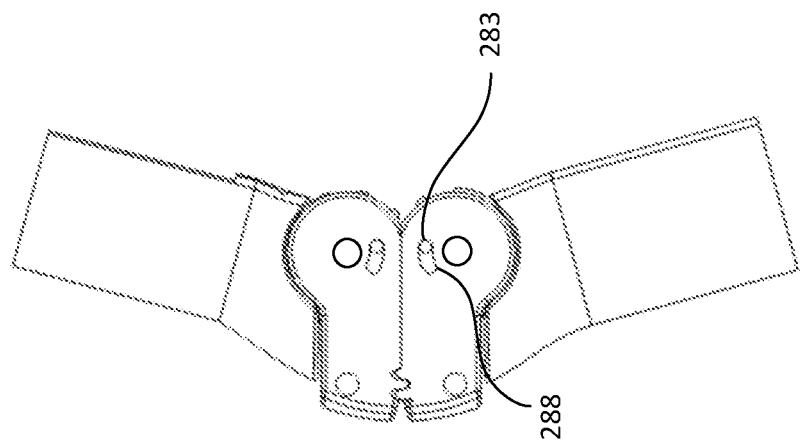
Figure 29A:
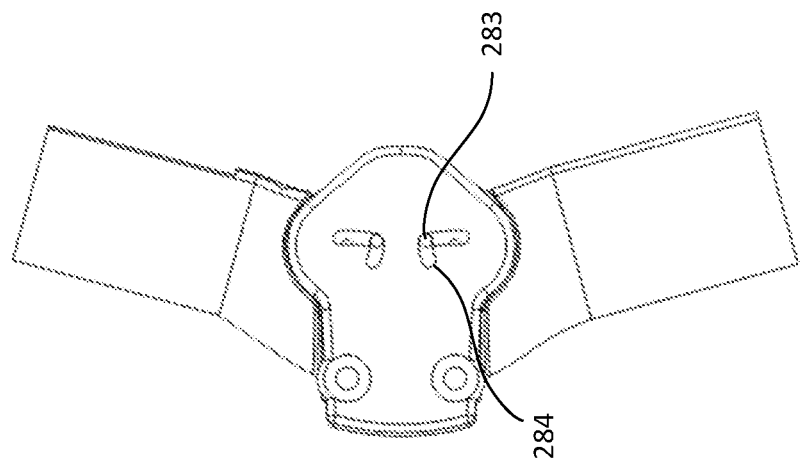

FIG. 29A shows the mechanism of FIG. 28A-28C when the top and bottom frame elements correspond to roughly 30 degrees of flexion. The pin (283) has reached the end of one arc of the slot (284). FIG. 29B is the same view with the outer cap removed. The pin (283) is also at the end of the arc (288) in the slot in the inner cap. The bottom frame element cannot rotate any further clockwise with respect to the inner caps because the pin has reached the end of the arc slot (288). FIG. 29C shows the position of the top and bottom frame elements with the inner caps removed. The gear teeth of the top and bottom frame elements are still (fully) engaged.

Figure 30C:
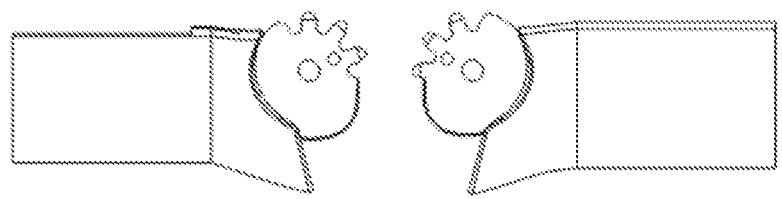
FIGS. 30A-30C illustrate the compound distraction hinge of FIGS. 28A-28C at the limit of rotation about a second axis, according to embodiments of the present invention.
Figure 30B:
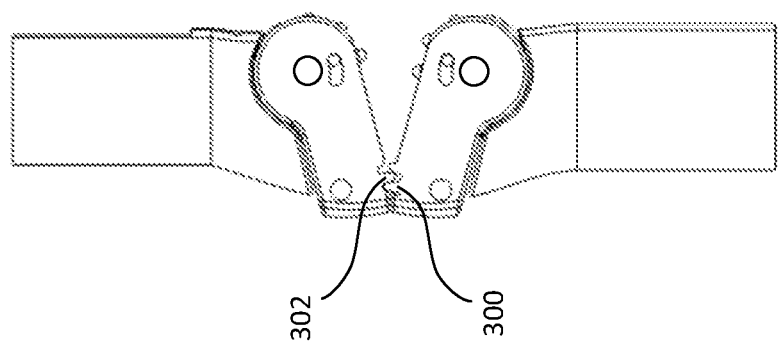
Figure 30A:
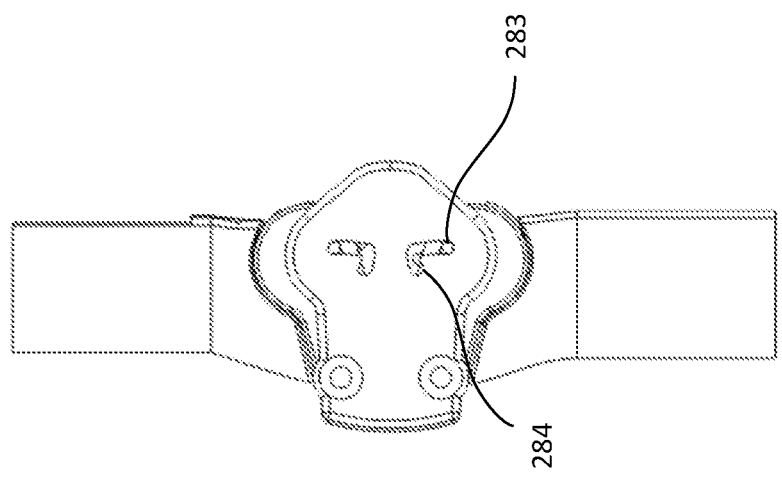

FIG. 30A shows the mechanism of FIG. 28 and FIG. 29 when the top and bottom frame elements are substantially in the fully extended position (0 degrees flexion). In the fully extended position, the pin (283) has reached the end of the other arc element of the slot (284). FIG. 30B shows the same mechanism with the outer cap removed to see the position of the inner caps. The inner caps comprise geared teeth, whereby the inner upper cap and the inner lower cap act as intermeshing gears. The gear teeth of the lower inner cap (300) and the upper inner cap (302) are (fully) engaged; that is, the rotation of the lower inner cap is synchronized with the rotation of the upper inner cap. FIG. 30C shows the upper and bottom frame elements without the inner caps. The gear teeth of the upper and lower frame elements are no longer engaged. The pin (283) is preventing the lower frame element from rotating about the pivot (299) because the arc slot (284) only permits rotation about the pivot (299) when the lower frame element is in flexion of about 30 degrees or more, in aspects. As shown in FIG. 28 and FIG. 29, the lower and upper frame element gear teeth are engaged when the flexion angle is about 30 degrees or more. At flexion angles of less than roughly 30 degrees the gear teeth of the upper and lower inner frame elements are engaged. Thus, the pins and slots work with the gear teeth of the inner caps and the frame elements to prevent the upper and lower frame elements from being pulled out of sync during the entire range of motion of the frame elements.

The various embodiments of the present invention provide distraction to the joint by applying forces—predominantly along the axes of the bones that comprise the joint—tending to pull them apart. The various embodiments may be disposed on the lateral side of the joint, the medial side of the joint, or both sides simultaneously—unlike traditional three point bending braces. Traditional three point bending braces create a moment of rotation about the joint which opens one side (while putting pressure on the opposite side).

In situations where a moment of rotation is desirable (to correct for varus or valgus, for example) it is possible to generate such a moment of rotation with the present invention without putting (in aspects, any) compressive pressure on the joint. By providing distraction elements on the lateral and medial sides of the brace with different amounts of distraction, a moment of rotation will be induced. In some aspects, a combination of traditional three point bending (non-synchronized distraction mechanism) and the synchronized distraction of the present invention may be an acceptable solution depending on the patient's needs. Such a combination could provide a minor distraction force over the entire range of flexion with a major distraction over a specific range of flexion.

The amount of distraction applied by the present invention and the amount of distraction that actually occurs at the joint (the effective distraction) may differ. The presence (or absence) of adipose tissue, muscle tone, amount of muscle, etc., as well as the type of orthosis strapping, will have an effect on the conversion of the applied distraction versus the effective distraction. Thus, the amount of distraction that an orthosis should provide across a joint may vary from individual to individual even if the same physiological force ($F_u$) to alleviate joint dysfunction is prescribed.

In addition to physiological factors such as adipose tissue, muscle tone, muscle mass, etc., geometrical factors such as the width of the joint, the size of the wearer, etc., all contribute to the effective distraction transmitted to the joint by the brace or components of the brace. In addition, the activity intended will have an impact on the amount of distraction to be provided. For example, the forces on the knee are much greater when running than when walking, or when walking up stairs than when walking on level ground.

An algorithm that fine tunes the amount of distraction for a knee brace taking into effect the patient's biophysical data, their current (or anticipated) pain level, the types of activities intended is needed. In aspects, clinical trials would be run to fine tune the algorithm and/or the determined amount(s) of distraction. The amount of distraction provided by an orthosis could be directly proportional to body mass index (BMI). That is, the greater the body mass index, the greater the distraction the orthosis would need to provide to the limb to achieve the same effective distraction at the joint. Likewise, the amount of distraction could be directly proportional to the amount of adipose tissue, the severity of the patient's pain (e.g., value on the Koos pain score), the degree of varus, or the width of the joint (e.g., the condyle width for a knee joint). The amount of distraction could be inversely proportional to the height of the patient; in those cases, the orthosis can be custom made for the patient and thereby the length of the moment arm from the top and bottom of the orthosis to the joint can vary or be adjusted. The amount of distraction could also be directly proportional to the activity level of the intended use. For example, more distraction would be required for an elbow brace when playing sports versus office work. There can also be a balance between the distraction provided by a variable distraction mechanism of the present invention and the constant amount of distraction provided by, for example, a three point bending mechanism.

In a non-limiting embodiment, a proposed balance of how much three point bending displacement versus how much variable distraction is shown in the following table:

| Koos Pain Score | Ratio of Disp to Dist |
| --- | --- |
| 1-5 | 75% Disp/25% Dist |
| 5-7 | 50% Disp/50% Dist |
| 7-10 | 25% Disp/75% Dist |

Figures 31A, 31B:
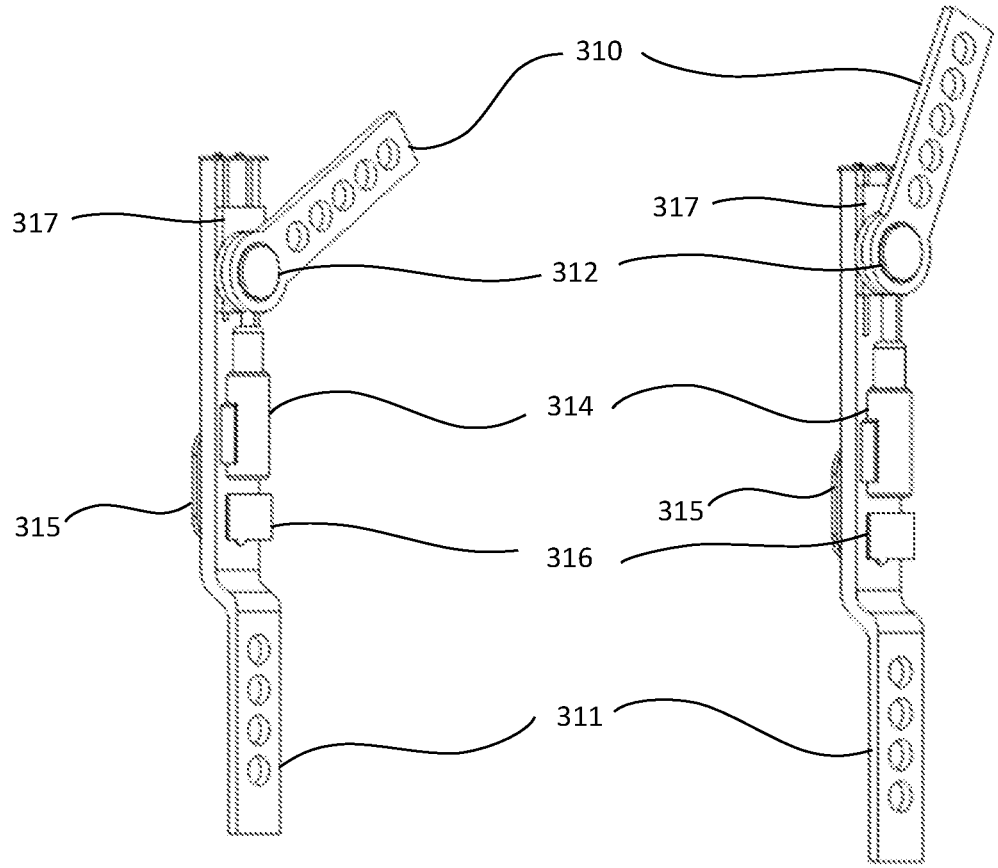
FIGS. 31A-31B illustrate a motorized distraction hinge capable of synchronizing the distraction with the flexion of the body part, according to embodiments of the present invention.

Another embodiment and means of generating a joint distraction force according to the present invention is shown in FIG. 31A and FIG. 31B. A motor can be used to automatically position a hinge element based on a sensor reading. In an embodiment, a linear actuator (314) can be connected to a battery (315) and a microprocessor (316). The microprocessor can determine the amount of flexion of the upper frame element (310) versus the lower frame element (311) via, for example, a goniometer or other sensor located in the pivot point (312). The microprocessor can then calculate the desired amount of distraction from an algorithm or a lookup table. The microprocessor can energize or otherwise initiate the linear actuator which pushes a slide (317) until the desired hinge distraction is obtained. FIG. 31B shows an increased distracted position of the slide when the upper frame element (31) has rotated towards extension. In the example shown in FIG. 31A and FIG. 31B, a uni-centric hinge is shown. However the same sensor/microprocessor/motor combination could be used in a bi-centric hinge mechanism. Likewise, the mechanism in FIG. 31A and FIG. 31B only applies a distraction force across one limb or body part connected to the joint. Alternative embodiments employing two linear actuators (for example) could apply distraction forces to both limbs connected to the joint or a single motorized element could drive, for example, a central cam that pushes on two followers such that a distraction force is applied to both limbs.

Other mechanisms of generating distraction forces such as a screw and nut, rack and pinion, and/or cam and follower, are alternatives for the linear actuator.

Figure 32A:
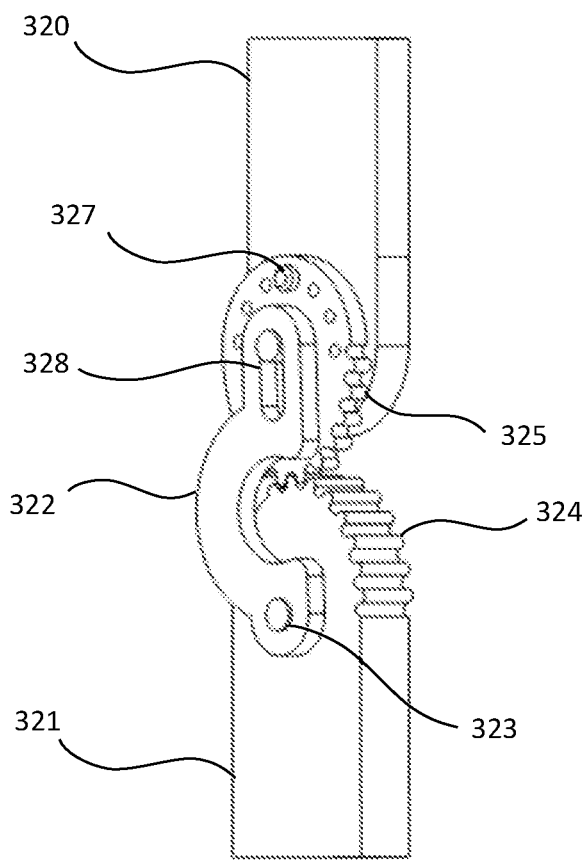
FIGS. 32A-32B illustrate a bicentric toothed distraction hinge with an adjustment mechanism to change the desired amount of distraction, according to embodiments of the present invention.

Another embodiment and means of generating a joint distraction force according to the present invention is shown in FIG. 32. In this Figure, a manual adjustment of a distraction hinge is shown in FIG. 32A. This embodiment is similar in aspects to the invention shown in FIG. 26. In this embodiment, the manual adjustment allows the wearer to change the amount of distraction provided day-by-day or wearing-by-wearing. Such an adjustment would be advantageous for using the orthosis over a long period of time when the wearer may have a change in their BMI due to a weight loss. The corresponding loss of adipose tissue may contribute to the previous amount of applied distraction applied by the orthosis resulting in greater than the desired joint distraction force ($F_u$). Thus, the ability to change (in this case, reduce) the total amount of applied distraction is desired. Likewise, there may be times when it is advantageous to change at which range of flexion the maximum amount of distraction is applied.

Figure 32B:
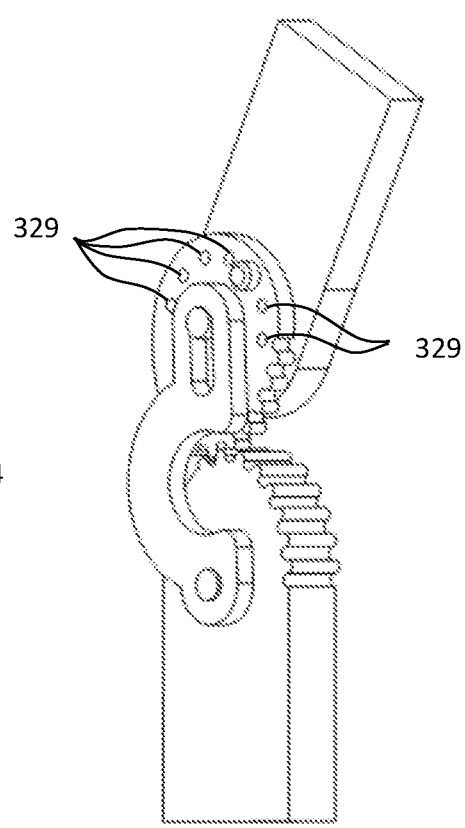

In FIG. 32A, an upper arm (320) is connected to a lower arm (321) by a hinge cap (322). There is a variable radiused toothed surface (325) and (324) at the distal ends of the upper and lower arms, respectively. The lower arm pivots using a pivot point (323). The upper arm pivots and slides to accommodate the distraction using a slot (328). The variable radiused toothed surface (325) can be adjusted to different levels of distraction by a pin (327) which can couple the variable radiused toothed surface (325) to the upper arm (320). FIG. 32B shows how the variable radiused toothed surface (325) can be connected to the upper arm (320) in another position of the adjustment holes (329), which changes the distraction versus flexion angle.

Other methods can be used to adjust the amount of distraction provided by the hinge such as using wedges or screws to flex the surface of the variable radiused tooth surface, using a screw and nut, rack and pinion, or cam and follower to reposition the variable radiused toothed surface with relation to its corresponding arm.

The separation of the two axes of rotation of a compound distraction hinge can be determined by the flexion angle over which the distraction should occur and by the amount of distraction desired. Smaller angles and larger distractions can increase the separation distance between the axes of rotation. For some joints, such as a knee joint, the needed distraction distance and desired flexion range create a hinge geometry which may be larger than optimum, for example, if the device is to be worn under a pair of pants. A compact version of a compound distraction hinge is desired.

Figure 39:
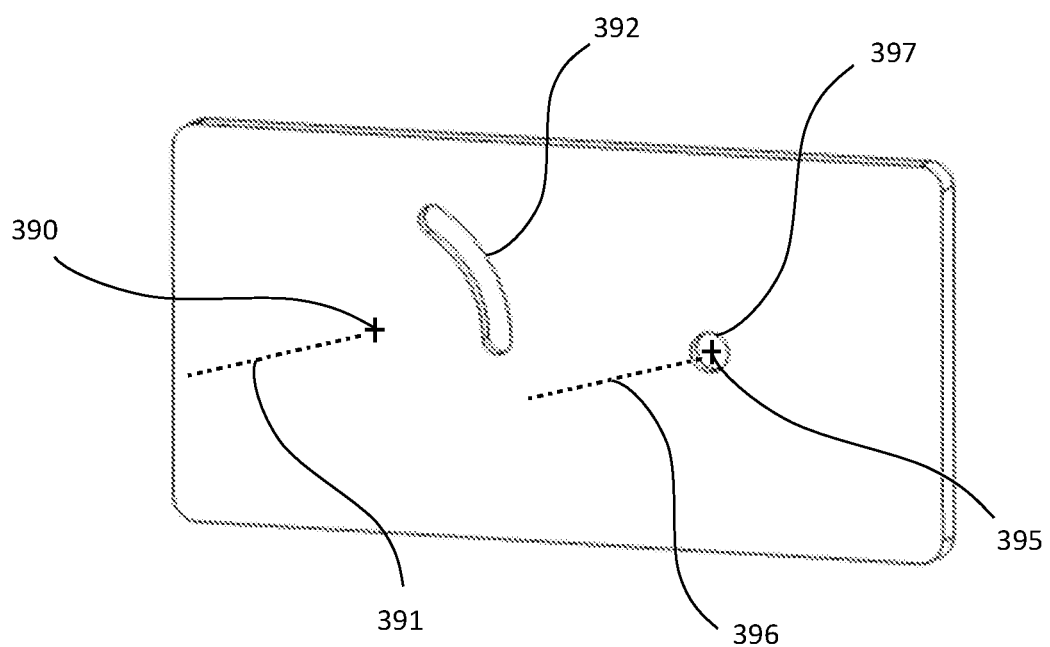
FIG. 39 is an illustration of rotation defined by a pivot point and rotation defined by an arc.

FIG. 39 illustrates two examples of mechanical rotation of a part, which can be used along with means of generating a joint distraction force according to embodiments of the present invention. On the right side of FIG. 39 there is drawn a center of rotation (395) and an axis of rotation (396). The center of rotation and axis of rotation are geometrical concepts. The pivot point (397) is a physical manifestation of the center of rotation. An object that rotates about the pivot point would also rotate about the axis of rotation (396). On the left side of FIG. 39 there is a second center of rotation (390) and an axis of rotation (391). The arc slot (392) is a physical manifestation of a circular path which is centered about the axis of rotation (391). An object which slides along the arc slot (392) would also rotate about the axis of rotation (391).

Figure 33B:
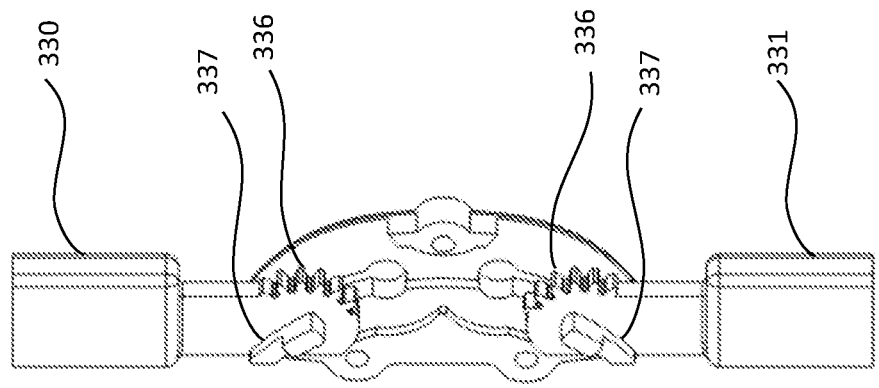
FIGS. 33A-33B illustrate a compact compound distraction hinge in full extension.
Figure 33A:
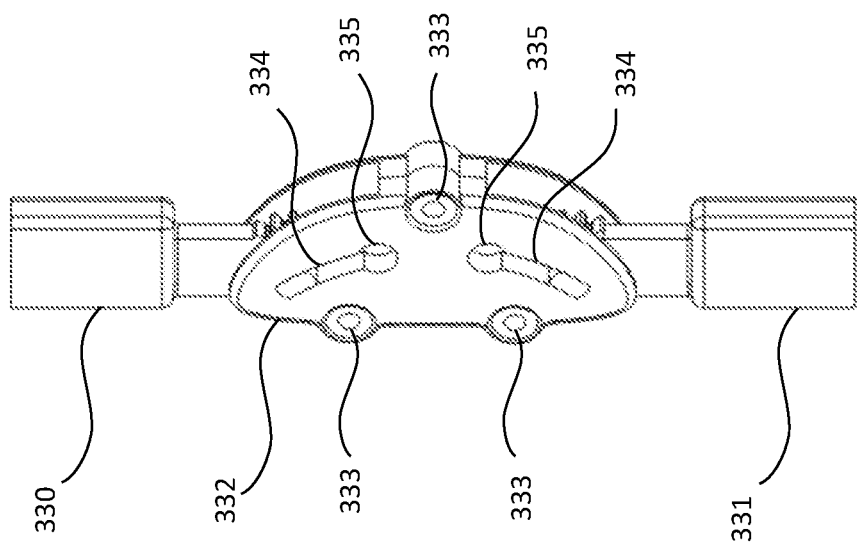

FIG. 33 shows another embodiment and means of generating a joint distraction force according to the present invention. FIG. 33A shows an embodiment of a compact compound distraction hinge at full extension (that is, zero degrees flexion). The upper arm (330) and the lower arm (331) are fully distracted and are at their maximum separation. The upper arm (330) and lower arm (331) are held together with a hinge cap (332). The hinge cap (332) has two halves which are mirror images of each other which are joined with bolts (not shown) via the three bolt holes (333).

The hinge cap (332) has a slot that defines the rotation of the upper and lower arms. These slots have an arc portion (334) and a pivot portion (335). The arc slot and pivot define the two axes of rotations of the compound hinge. Unlike the embodiment of FIG. 28, the arms of the compound hinge of FIG. 33 do not each rotate by means of pivot points. Instead, the embodiment of FIG. 33 shows that the arms sometimes rotate by means of a pivot point (335) and sometimes rotate by means of an arc slot (334). The advantage of using an arc slot instead of a pivot point is that the center of rotation of an arc slot does not need to be physically within the boundaries of the hinge cap (332). In this manner, the hinge cap can be made more compact.

FIG. 33B shows the mechanism of FIG. 33A with one half of the hinge cap (332) removed for clarity. The arms have a slider (337) and a toothed surface (336). The slider (337) can slide along the arc slot (334) but can only rotate about the pivot point (335) when the slider is at the limit of travel along the slot (334) that corresponds with the pivot point (335). At full extension, as shown in FIG. 33A and FIG. 33B, the toothed surfaces (336) are not engaged.

Figure 34:
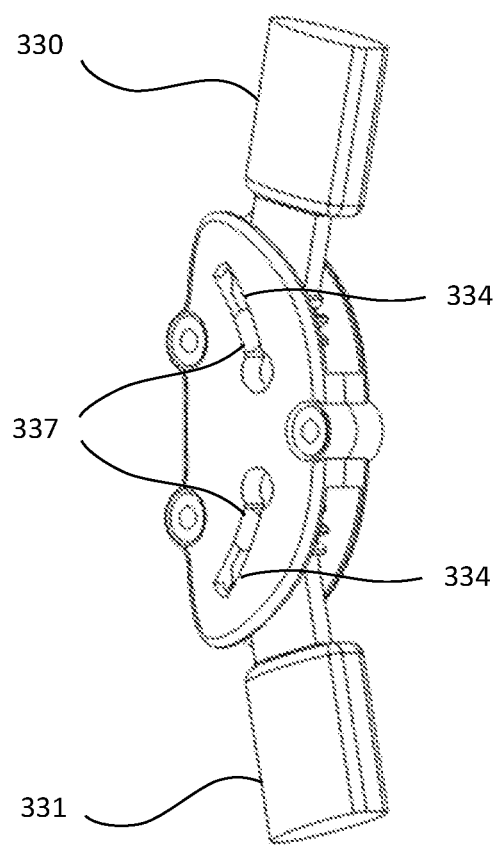
FIG. 34 illustrates a compact compound distraction hinge in partial flexion.

FIG. 34 shows the mechanism of FIG. 33A and FIG. 33B at an intermediate point of flexion. The sliders (337) are constrained along the arc slot portion (334) of the slots and thus the arms (330) and (331) are rotating about an axis of rotation that is physically outside the dimensions of the hinge cap.

Figure 35B:
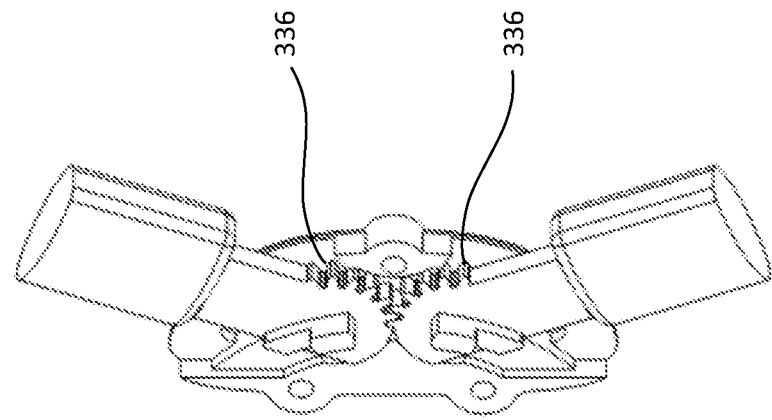
FIGS. 35A-35B illustrate a compact compound distraction hinge at the limit of rotation about one axis.
Figure 35A:
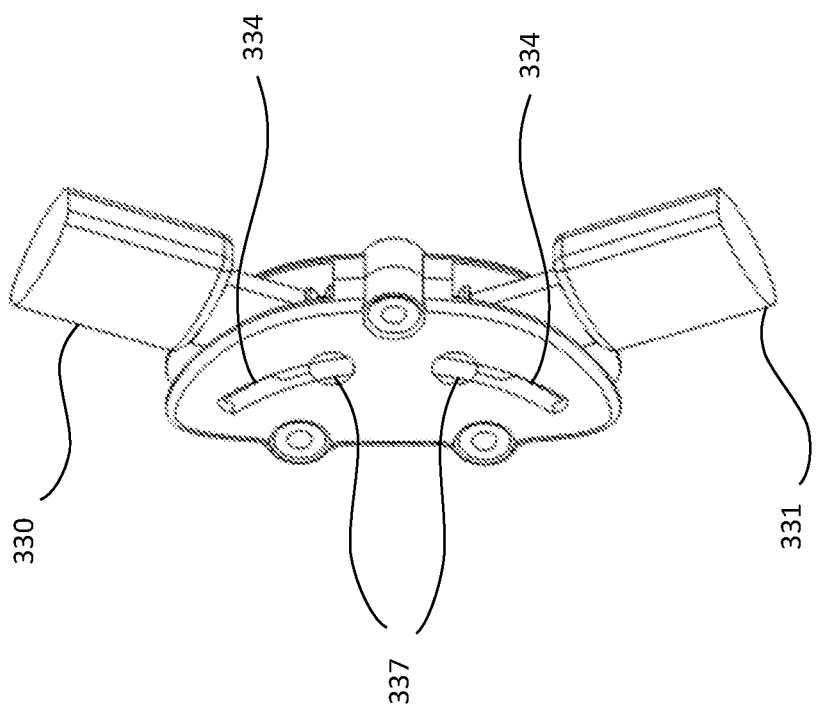

FIG. 35A and FIG. 35B show the mechanism of FIG. 33A and FIG. 33B when the arms (330) and (331) are at one limit of travel along the arc slots (334). FIG. 35B shows the mechanism of FIG. 35A with one hinge cap removed for clarity. It can be seen in FIG. 35B that the toothed surfaces (336) of the arms are engaged. At this angle of flexion the compact compound hinge is not providing any distraction to the joint.

FIG. 36A and FIG. 36B show the mechanism of FIG. 33A and FIG. 33B at another point of flexion. The sliders (337) are now able to rotate about the pivot points (335) of the slots in the hinge caps. FIG. 36B shows the mechanism of FIG. 36A with one hinge cap removed for clarity. On the interior of the hinge caps, there are shoulders (360) upon which the sliders (337) may slide.

As shown in FIGS. 34-36, a slider (or pin) traveling in a groove or slot can be used to define the motion of a frame element with respect to the hinge cap. If the slider (or pin) is round in cross section, the slider (or pin) may rotate as well as traverse the groove or slot. In some aspects, the dual rotation and translation of the frame element is advantageous however it may be desirable to limit the rotation about the axis of the slider (or pin). By using multiple sliders (or pins) and multiple grooves or slots, the combined translation and rotation of the frame element with respect to the hinge cap can be confined to a preconfigured path thereby synchronizing the distraction with the flexion angle of the frame element. It is noted that the pin and slot configuration can be inverted with a similar effect, and that the pin and slot system can also be configured to allow for rotation or other desirable movements of the knee as it articulates throughout a range of motion. Some examples include pulling the tibia posteriorly, or pushing the femur anteriorly.

Figure 37:
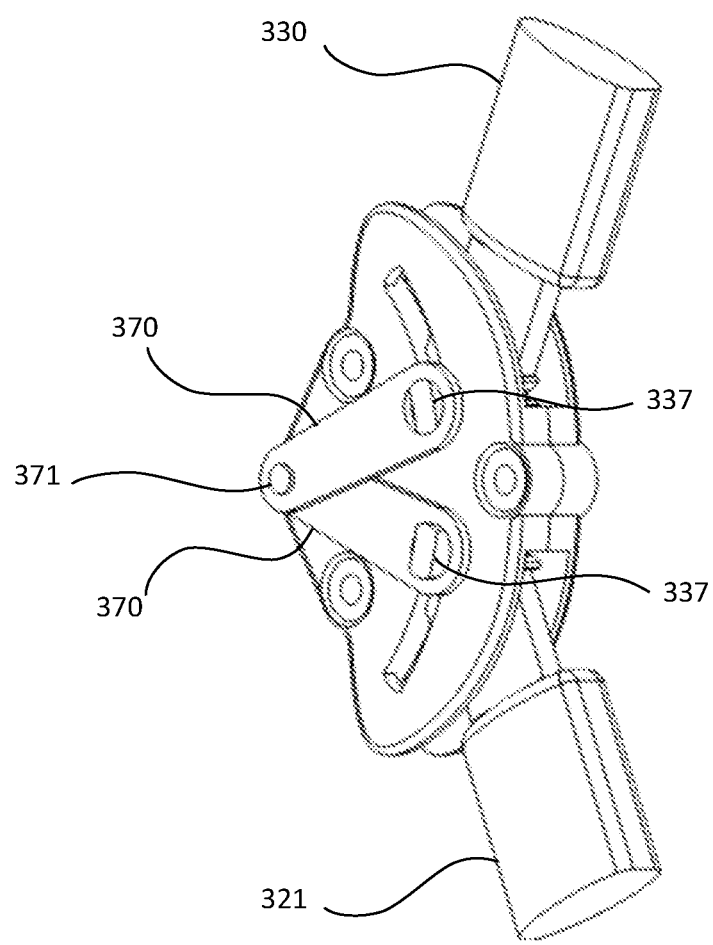
FIG. 37 illustrates another embodiment of a compact compound distraction hinge with a bar linkage system.

FIG. 37 is another embodiment and means of generating a joint distraction force according to the present invention. FIG. 37 shows another embodiment of the compact, compound distraction hinge. Portions of the sliders (337) have been extended to rest in holes of four arms (370). Two arms are shown in FIG. 37; two other identical arms are hidden behind the hinge caps. A pin (371) connects the four arms (370).

FIG. 38A shows a side view of the mechanism shown in FIG. 37. FIG. 38B shows the same side view with the arms (370) removed for clarity. In FIG. 37B, it can be seen that the pin (371) rides along a slot (380) in the hinge caps. As before, the toothed surfaces maintain synchronous movement between the upper and lower arms when the arms are rotating about the pivot points. Now, when the arms are rotating about the axis of rotation defined by the arcs, the arms/pin/slot subcomponents work together to maintain synchronous movement of the upper and lower arms.

Figure 40B:
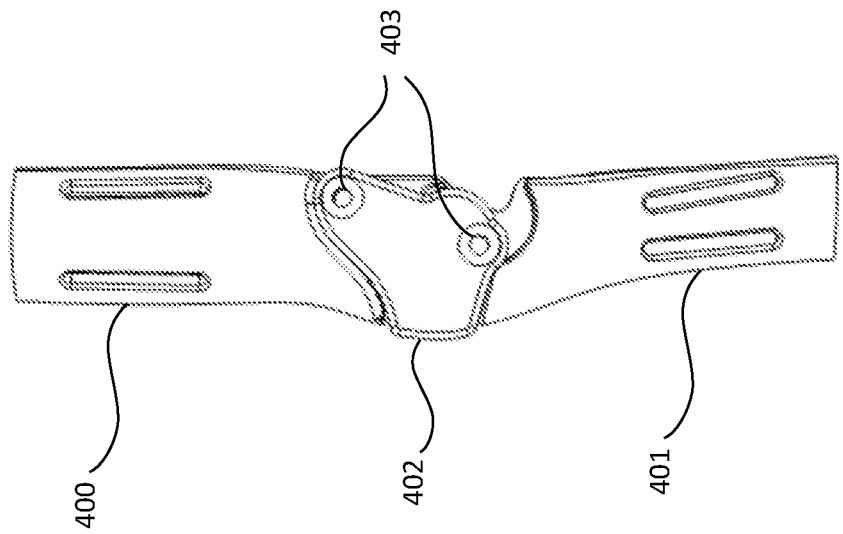
FIGS. 40A-40B illustrate a 4 bar linkage distraction mechanism at full extension.
Figure 40A:
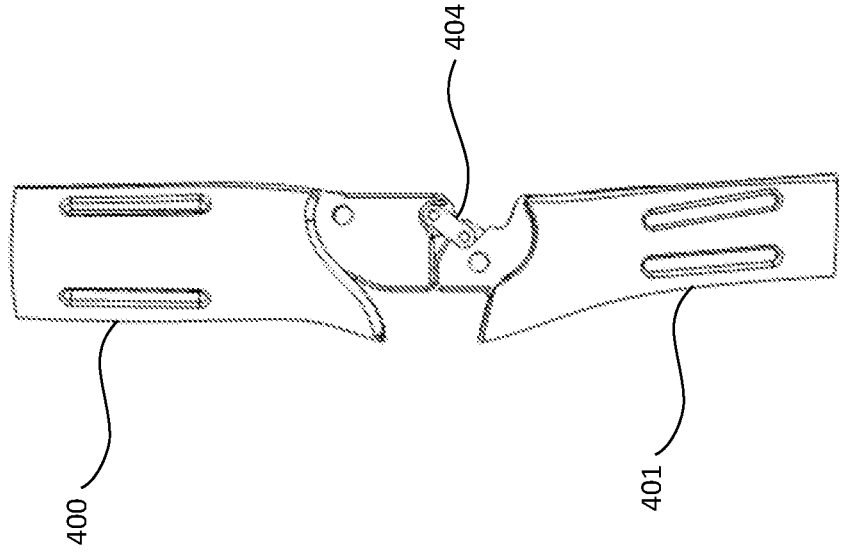

FIG. 40 shows another embodiment and means of generating a joint distraction force according to the present invention. Another embodiment of a distraction hinge is shown in FIG. 40A and FIG. 40B. This mechanism uses a 4 bar linkage to synchronize the distraction distance to the degree of flexion of the limb. An upper frame element (400) and a lower frame element (401) are connected with a hinge cap (402) and a linkage (404). In FIG. 40B the hinge cap (402) has been removed to show the position of the linkage (404). Barrel bolts (not shown) act as the pivot points (403) in the hinge cap and facilitate the assembly of the mechanism. The positions of the upper frame element and the lower frame element correspond with full extension of the joint (e.g. 0 degrees flexion) and the maximum distraction.

Figure 41B:
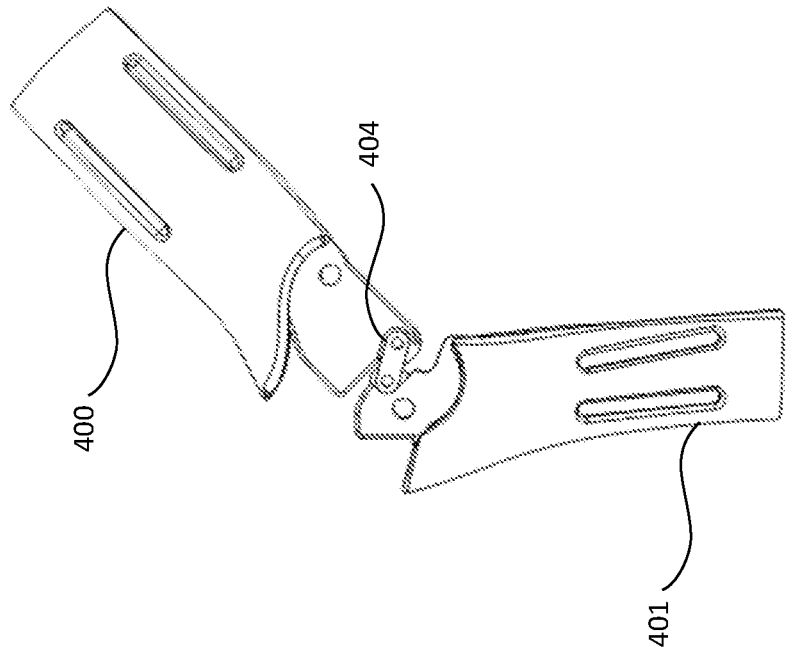
FIGS. 41a-41b illustrate a 4 bar linkage distraction mechanism at 45 degrees of flexion.
Figure 41A:
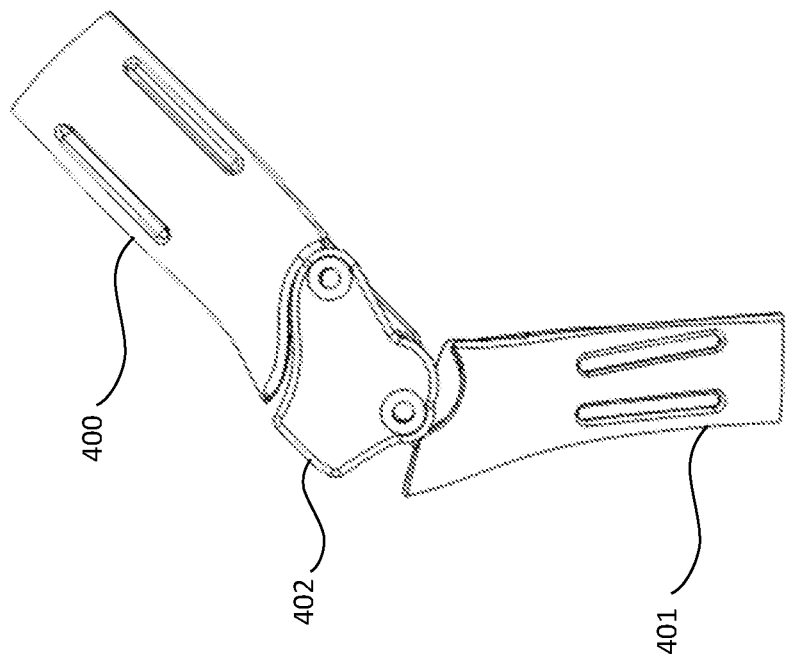
Figure 42A:
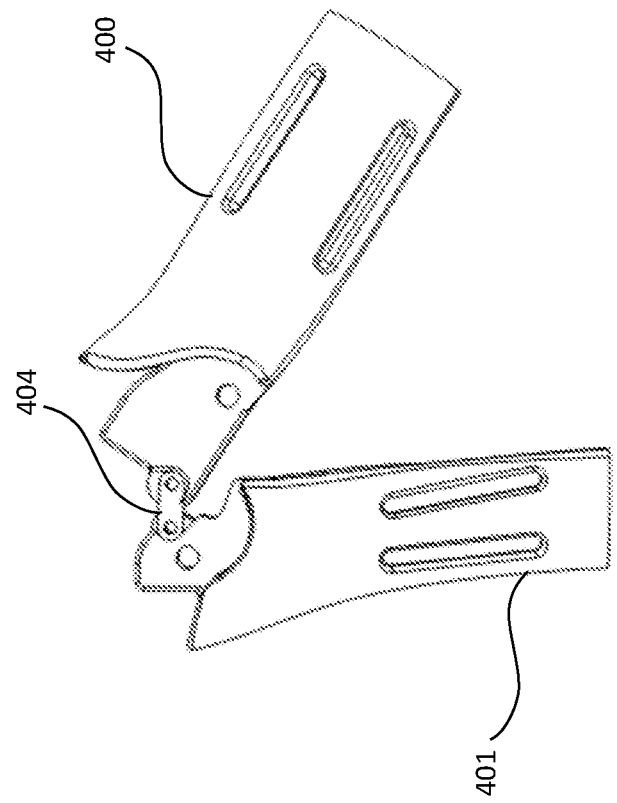
FIGS. 42A-42B illustrate a 4 bar linkage distraction mechanism at 120 degrees of flexion.
Figure 42B:
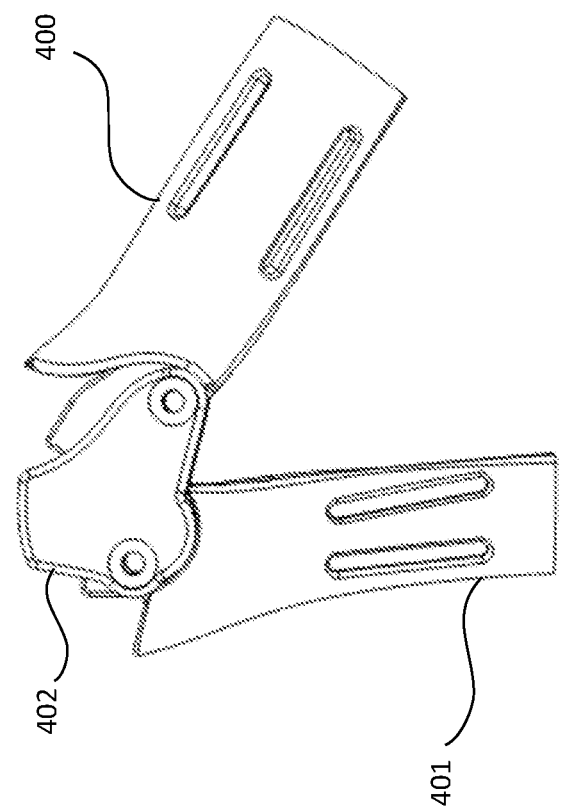

FIG. 41A and FIG. 41B show the same mechanism of FIG. 40A and FIG. 40B when the upper frame element (400) is at 45 degrees of flexion with respect to the lower frame element (401). FIG. 42A and FIG. 42B show the same mechanism of FIG. 40A and FIG. 40B when the upper frame element (400) is at 120 degrees of flexion with respect to the lower frame element (401).

Figure 43B:
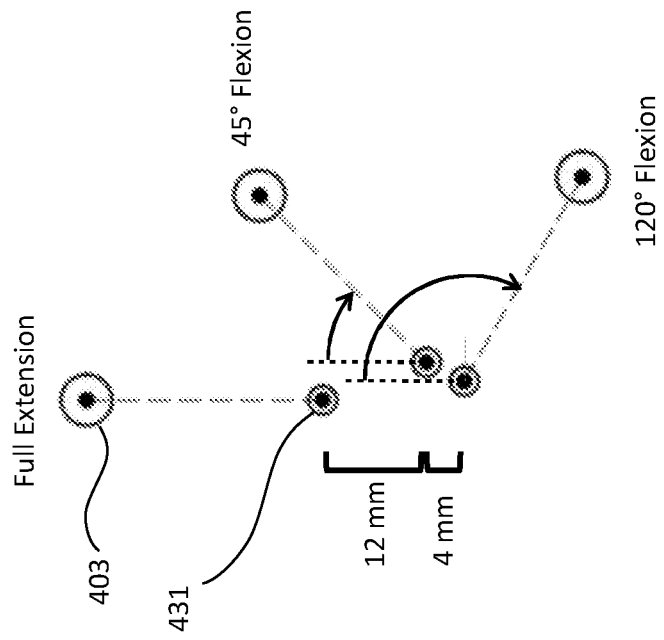
FIGS. 43A-43B show the amount of distraction provided by the 4 bar linkage distraction mechanism at the degrees of flexion shown in FIGS. 40-42.
Figure 43A:
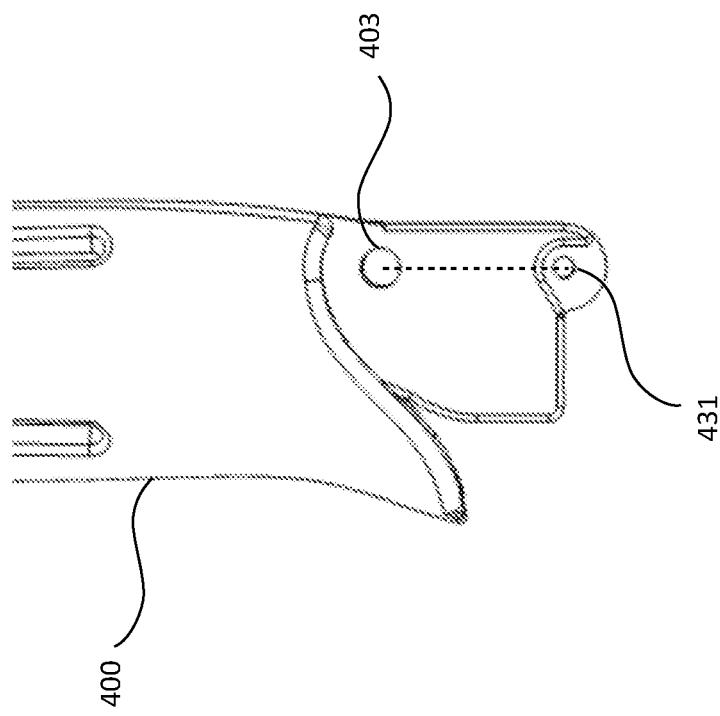

FIG. 43A shows a portion of the upper frame element (400) when it is at full extension (or 0 degrees flexion). There is a pivot point (403) that connects the hinge cap (402) (not shown) to the upper frame element and a pivot point (431) that connects the linkage (404) (not shown) to the upper frame element. A dashed line connects the two pivot points and represents the orientation of the upper frame element. FIG. 43B shows the relative locations of the pivot points (403, 431) as the upper frame element moves from extension to flexion. FIG. 43B is not at the same scale as FIG. 43A. FIG. 43B shows that, in aspects, there is a 12 mm distraction as the upper frame element swings from 45 degrees flexion to full extension. That is, the location of the pivot point (431) rises in the vertical direction by 12 mm. There is a secondary distraction of, in aspects, 4 mm when the upper frame element swings from full flexion, that is 120 degrees of flexion, to 45 degrees of flexion. In use cases, joint distraction at large values of flexion is not desirable. The 4 bar linkage mechanism shown in FIGS. 40-43 has been optimized to minimize the amount of distraction from 120 to 45 degrees of flexion and to maximize the amount of distraction from 45 degrees of flexion to full extension.

In aspects, the device/orthosis described herein will distract by at least 5 mm (e.g., the first member pivot point and the second member pivot point will be separated by at least 5 mm during the distracting range). However, it is envisioned that the device could distract by 1 mm, 2 mm, 3 mm, 4 mm, and up to 5 mm, in addition to at least 5 mm separation.

A distraction hinge is useful when there is a need to relieve pressure on a body joint. For example, it can be physiologically advantageous to provide distraction forces across the ankle joint, knee joint, wrist joint, hip joint, shoulder joint, elbow joint and in various locations along the spine. In embodiments, the distraction hinge of the present invention is able to change the amount of distraction as the joint or body part flexes thereby synchronizing the degree of distraction with the flexion angle of the limbs or body parts.

According to another embodiment of the current invention, a Joint Distraction Orthosis (JDO) can comprise two components: a securing element and a distraction element. A hinge element may optionally be provided. The purpose of the securing element is to hold the JDO in place on the limb. The securing element can or, in aspects, must, transmit the distraction forces to the joint yet not be uncomfortable to wear. Unlike a joint distraction surgery where the distraction forces are applied directly to the bones of the joint (e.g., using pins), the distraction forces of a JDO can be applied to the skin, muscle, and adipose tissue that surround the bone.

By way of example only, clamping a JDO to the limb would transmit the distraction forces to the bone, but would be unacceptably painful to wear and would cause tissue damage due to constriction of blood supply. Clamping is not a preferable solution but could be used in some aspects of the current invention. Alternatively, an ordinary elastic sleeve would be comfortable to wear on the limb, but may, in cases, not transmit sufficient distraction forces to be effective for a JDO. The present invention, in aspects, provides a balance between comfort, tissue health, and the transmission of joint distraction force efficacy.

The distraction element (e.g., means for generating joint distraction force) provides the forces necessary to separate the joint, thereby enabling the repair and growth of cartilage. The distraction element, in aspects, will not apply the forces abruptly, nor should it be able to provide too much force lest the connective tissue of the joint be damaged. Preferably, both the maximum force and the maximum distraction distance should be limited or otherwise controlled (or defined) by the distraction element. In aspects, the forces and distraction distance provided by the distraction element need to be able to be variable; as the JDO is worn, the desired amount of joint distraction can increase. (In surgical knee joint distraction, an initial amount of distraction—typically around 2 mm—is set when the pins are inserted into the tibia and femur. Over the next several days, the distraction distance is increased before the patient is discharged. In a similar manner according to the current invention, in aspects, the amount of distraction needs to be adjusted for a JDO over time.)

An optional hinge element can allow the JDO to be temporarily disabled by the wearer so that the limb can be used without a distraction force. For example, if a JDO is being worn on a leg to distract the wearer's knee joint, the leg, in aspects, will be locked in a fully or nearly-fully extended position. If the wearer wishes to temporarily remove the distraction force (to facilitate a trip to the bathroom, for example) a hinge element would allow the wearer to bend their limb (their leg in this example) without the need to completely remove the JDO. This convenience can have a marked improvement in patient compliance and device efficacy.

In another embodiment, a three point bending method is used for unloading the medial or lateral compartment of the knee. In embodiments, forces are applied to the thigh and the lower leg above and below the knee, respectively. A counter force is applied by the condyle portion of the orthotic. The femur and tibia rock at the knee joint due to the forces and unload the compartment opposite of the condyle force.

Three point bending forces are generated by strapping a knee brace to the upper and lower leg wherein the knee brace is configured such that the end of the upper frame element farthest from the knee joint is not adjacent to the thigh. Likewise, the end of the lower frame element farthest from the knee joint is not adjacent to the calf. Strapping such a knee brace to the leg pushes the condyle element into the knee while the frame elements pull on the upper and lower leg. This combination of forces produce a moment of rotation about the knee joint (in the coronal plane).

A common method to create the desired shape of the knee orthotic frame is incorporating a hinge or pivoting mechanism into the upper frame element which causes the frame to bend in the coronal plane. The degree of bending may be adjustable (e.g., via a worm screw) to change the amount of unloading the knee brace provides. In some cases, two adjustment mechanisms are used: one above and one below the knee joint. It is also possible to fabricate the knee brace frame elements so that they purposely bend away from the upper and lower leg.

The worm screw adjustment mechanism cab be adjusted by the orthotist using a tool (e.g., an Allen wrench) during the fitting of the knee brace to tune the degree of unloading in the medial or lateral knee compartment to the patient.

According to aspects of the invention disclosed herein, the method provides for adjusting or fine tuning the amount of three point unloading by the patient while the orthosis is being worn. That way, when the patient is experiencing higher than normal OA pain, they can increase the amount of three point bending—an amount that may be uncomfortable on most other days but is preferable than the OA pain at the moment. One method according to the present invention to fine tune the degree of three point bending is to adjust the condyle pressure by moving the condyle pad towards or away from the knee. In one embodiment, the condyle pad is connected to the hinge by a thread rod. A knob can be connected to the threaded rod opposite of the end connected to the pad. The threaded rod can pass through a threaded hole in the orthosis hinge. Turning the knob moves the condyle pad axially along the threaded rod. A friction fit, detents, ratchet and pawl mechanism, or other locking mechanism can be employed to prevent the unintentional rotation of the knob.

In another embodiment, the face of the condyle pad opposite of the knee has a ramped surface. A corresponding ramped surface is connected to the hinge cap. A slide in the case of a linear ramp, or an axle in the case of a cylindrical ramp, is manipulated by the wearer to increase the engagement (or decrease the engagement) of the two ramped surfaces, thereby moving the condyle pad towards or away from the knee.

Securing Element

Novel securing elements, distraction elements, and hinge elements are described herein for the use in a joint distraction orthosis.

Figure 44B:
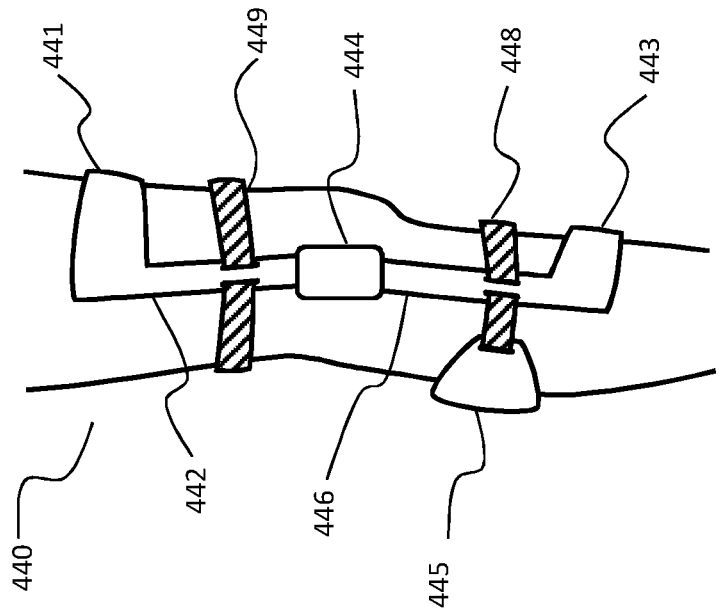
FIGS. 44A-44B show a JDO secured to a leg.
Figure 44A:
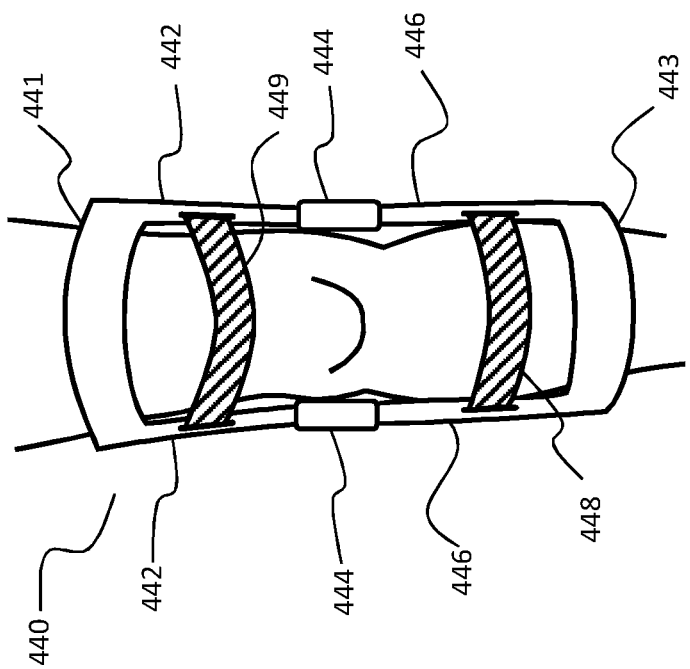

FIG. 44A shows the front view of a schematic of a JDO suitable for a knee (440), according to embodiments of the current invention. There is an upper cuff (441) and a lower cuff (443) which are connected by an upper frame upright (442) and a lower frame upright (446). In addition, straps (449) and (448) are used to secure the JDO to the upper and lower leg, respectively. The frame uprights are connected by a distraction element (e.g., means for providing joining distraction force) (444).

FIG. 44B shows a side view of a schematic of a JDO suitable for a knee (440). In this view, a lower load distribution element (445) is shown on the wearer's calf.

Figure 45:
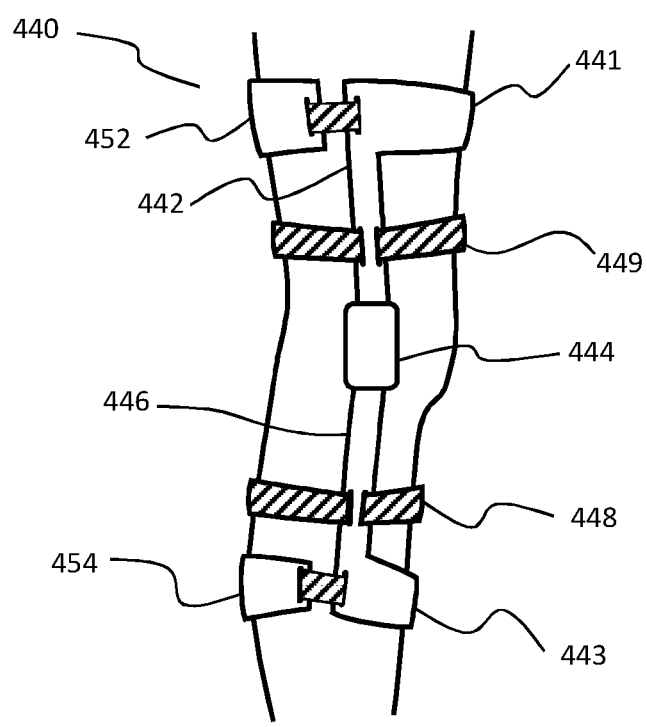
FIG. 45 shows another embodiment of a JDO secured to a leg.

FIG. 45 shows a side view of another embodiment of a schematic of a JDO suitable for a knee (440). An upper cuff (441) and lower cuff (443) are connected to the distraction element (e.g., means for providing distraction force) (445) by upper frame uprights (442) and lower frame uprights (444). Straps (449) and (448) secure the JDO to the upper and lower leg, respectively. In addition, a rear upper cuff (452) and rear lower cuff (454) provide additional contact with the leg to help transmit the distraction forces effectively. The lower load distribution element is not shown in FIG. 45 but could optionally be included.

The cuffs, straps, and load distribution elements in FIG. 44A, FIG. 44B, and FIG. 45 are examples of securing elements of the present invention. The cuff elements and load distribution elements can be preferably rigid or semi-rigid. In some embodiments, the cuffs and load distribution elements can be customized to the wearer's limb's dimensions. Such customization may be accomplished by, for example, taking a three-dimensional ("3D") scan of the wearer's limb, transforming the scan into a computer readable file, manipulating the file, for example, with CAD software, saving the altered file in a machine readable format, and manufacturing a customized part from the machine readable file (e.g., 3D printing the part). Alternatively, measurements may be taken of the wearer's limb directly or from a photograph or other rendering with fiducial reference marks included to enable dimensions to be determined from the photograph or rendering.

The straps in FIG. 44A, FIG. 44B, and FIG. 45 are, in aspects, preferably conformable. Examples of materials suitable for strapping include but are not limited to cord, fabric, woven straps, lace, webbing, and velcro straps. In embodiments, the strapping may have elastic qualities in addition to being conformable.

Various combinations of cuffs, load distribution elements, and straps may be combined to create a securing element that is able to transfer the distraction forces generated by the distraction element to the limb.

The upper securing element shown in FIG. 44A has an anterior rigid or semi-rigid shell and a posterior rigid or semi-rigid shell. The anterior shell and the posterior shell can be connected by a flexible element, cord, fabric, strap, or the like. In the embodiment shown in FIG. 44A, applying tension on the laces tightens the anterior and posterior shell to the wearer's thigh. Tension is applied by pulling on the tabs through which the laces have been threaded. The tabs are held in tension by securing them via velcro on the back of the tab to a corresponding velcro strip on the anterior shell.

In other embodiments, a corresponding velcro strip can be positioned on the anterior shell, posterior shell, and/or the flexible element joining the anterior and posterior shells, or combinations thereof.

In another embodiment, the tabs can be secured to the upper securing element via variously disposed hooks, tabs, slots, rings, catches, and similar securing mechanisms.

In another embodiment, the lace is attached to a spool, such as, by way of example, the disclosed invention in U.S. patent application Ser. No. 18/075,203, such that winding a dial applies tension to the lace.

The lower securing element in FIG. 44A can have a rigid or semi rigid posterior shell. Straps, webbing, fabric, pads or the like, can wrap around the front of the wearer's shin to hold the lower securing element to the wearer's calf. A buckle and cinch are shown in FIG. 44A as the mechanism for tightening the lower securing element to the wearer's calf. This is exemplary only and other tightening mechanisms such as those described herein can be employed.

The rigid or semi-rigid shells of the lower securing element and the upper securing element can be form fitting by generating a 3D scan of the wearer's body part or limb, manipulating the scan using (for example) CAD software, generating a computer file, and printing the file using a 3D printer.

Figure 46:
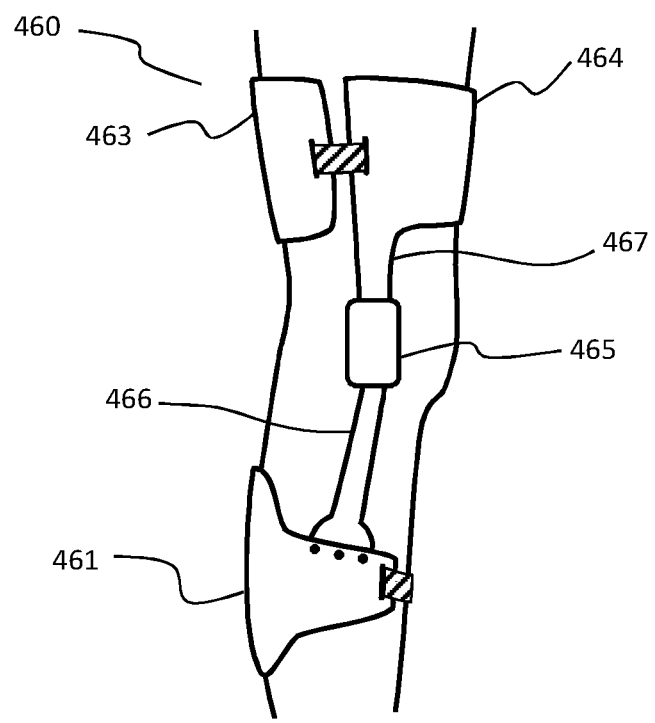
FIG. 46 shows another embodiment of a JDO secured to a leg.

In preferred embodiments, the JDO can be configured such that the securing elements take advantage of natural contours of the limb or body that help transmit the distraction forces of the JDO to the underlying bone. For example, the bulge that defines the calf or bicep muscle, or the transition from the ankle to the top of the foot. In the case of a JDO for a knee joint, in embodiments, there is a securing element on the thigh and a securing element on the calf. In preferred embodiments, the securing element can be contoured to the underlying muscle that is attached to the bones. FIG. 46 shows a JDO (460) that cups the calf and thigh. The lower securing element intended for the calf (461) is cupped-shaped to partially surround the upper bulge of the calf muscle. The calf muscle is attached to the tibia via the soleus tendon. Thus, a distracting force on the securing element can be able to transmit the force to the tibia. The upper securing elements for the thigh (463) and (464) are cone-shaped to mimic the shape of the thigh and prevent the upwards slide of the upper securing elements. In this manner, the distraction forces generated by the distraction element (465) are transmitted via the upper frame upright (467) and the lower frame upright (466).

Migration is the unwanted movement of a brace along the limb after it has been secured in response to forces applied to the brace (e.g., and only by way of example, gravity).

It is not always possible to cup the muscle as shown in FIG. 46. An injury or wound may prevent the placement of the securing element at the preferable location without discomfort. The wearer's muscle may be atrophied or not well defined. Adipose tissue may overlie the muscle inhibiting effective interaction between the securing device and the underlying bone. In such cases, it is possible or even likely that a large distraction force will cause the securing element to migrate, which will reduce the effectiveness of the distraction forces.

One way of dealing with migration according to the current invention is to make the securing element larger. A larger contact area spreads the forces over a larger area which can help to keep the securing element in place. Additional straps, stronger elastics, and/or using high friction surfaces, are other means of lessening migration, according to the current invention.

In another embodiment, a mechanism can be used to preload the securing element. By analogy, the purpose of the preloading mechanism is to "take up the slack" between the securing element and the underlying bone so that the distraction force can be applied effectively to the bone.

Figure 47:
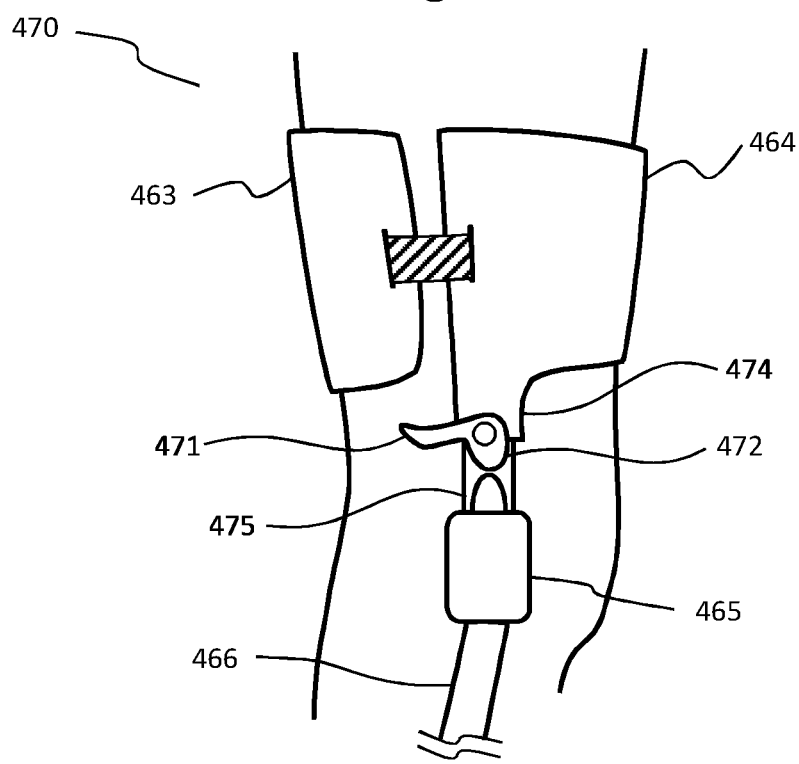
FIG. 47 shows a distraction element on a JDO suitable for a knee.

FIG. 47 shows one such embodiment on a JDO (470) with a lever (471) attached to a cam (472). The lever and cam are attached to a male (475) and female (474) sliding assembly that together make up the one of the medial or lateral upper uprights. FIG. 47 only shows the lateral side of the JDO (470). A similar mechanism can be employed on the medial upper upright (not shown). In aspects, the JDO is donned with the medial and lateral levers (471) in the relaxed position (cam not engaged). The straps, laces, elastics, etc., can be adjusted to hold the securing element in place. Before the distraction force is applied, the levers can be flipped to the engaged position which extends the upper frame elements and "take up the slack" between the skin/muscle/adipose tissue and the underlying bone. This is an example of a fixed distance preload mechanism according to the present invention.

Figure 48:
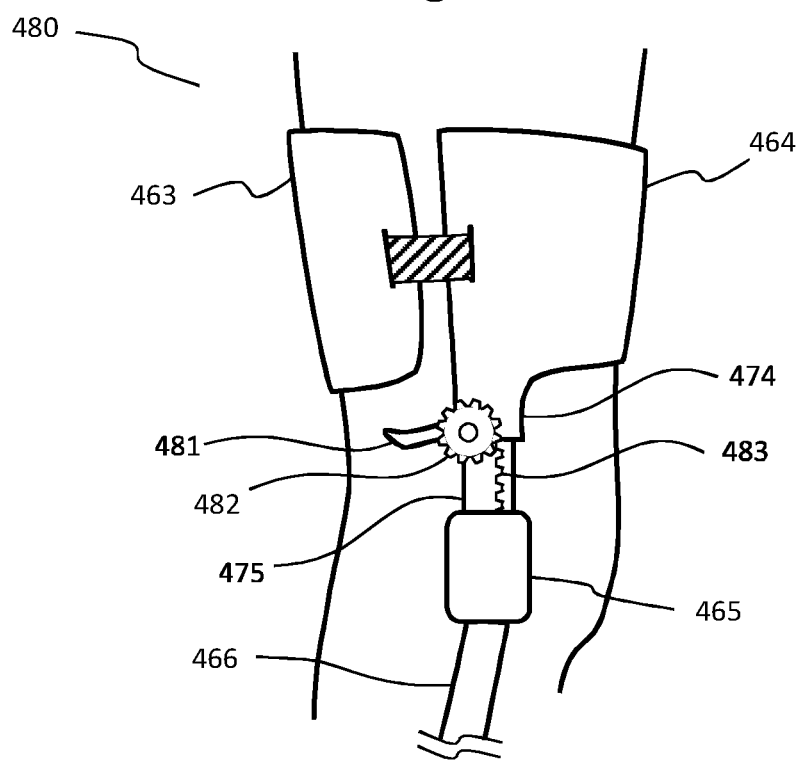
FIG. 48 shows another embodiment of a distraction element on a JDO suitable for a knee.

In another embodiment, shown in FIG. 48, a rack (483) and pinion (482) mechanism on the JDO (480) can be used as a preloading mechanism. In the relaxed position, the rack is not extended. Flipping the lever (481) rotates the pinion which extends the rack to the engaged position. The rack and pinion are attached to a male (474) and female (475) sliding assembly to together make up one of the medial or lateral upper uprights.

Figure 49:
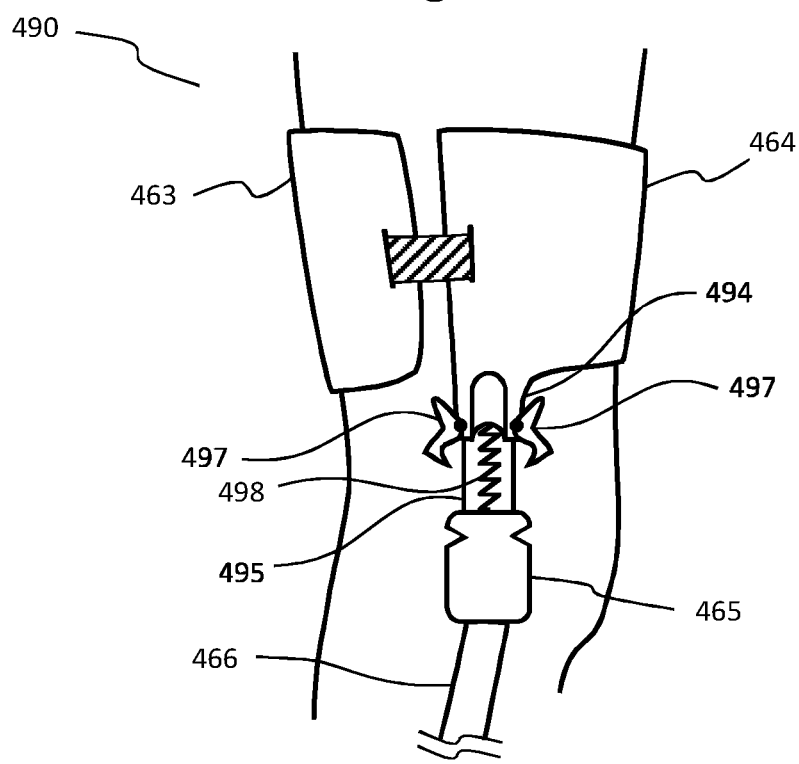
FIG. 49 shows another embodiment of a distraction element on a JDO suitable for a knee.

FIG. 49 shows a fixed force preload mechanism (490). A spring (498) is placed inline with the male (495) and female (494) slide assemblies of the medial and lateral frame elements. Before the JDO is attached, the frame is compressed and catches (497) are engaged holding the frame elements together. At this point, the straps, laces, elastics, etc., can be adjusted to hold the securing element in place. Before the distraction force is applied, the catch is released allowing the spring to expand the frame element and "take up the slack" as described above and herein.

Accounting for the amount of migration of the JDO along the limb before forces are effectively transmitted to the underlying bone—can be important for efficacy and safety. For knee joint distraction surgeries, the tibia and femur are only distracted by 2-5 mm. The migration of ordinary knee braces often is much larger than this amount. Thus, a way of knowing how much "slack" needs to be preloaded can be important for accurately distracting a joint.

Figure 50:
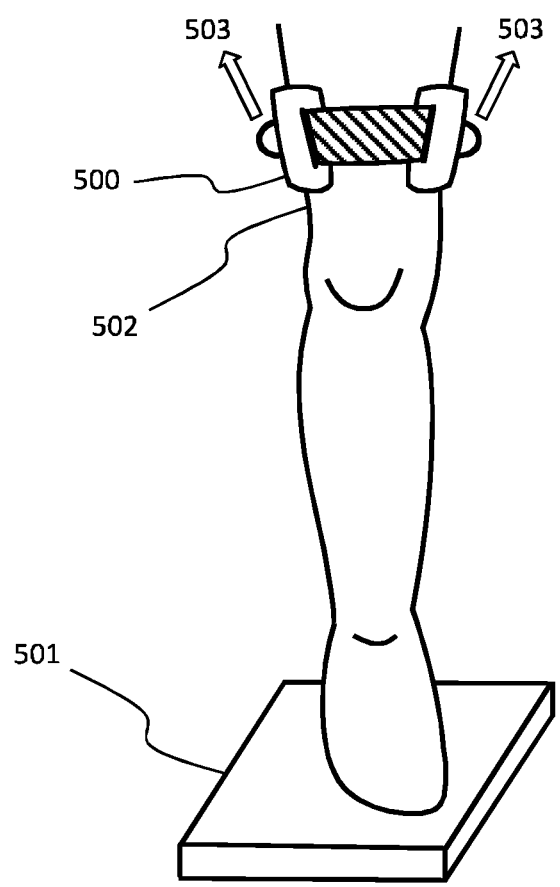
FIG. 50 illustrates a method for determining the pre-load for a JDO.

One method of measuring the "slack" according to the present invention is shown in FIG. 50. An upper securing element of a JDO, or an artifact (500) that mimics the upper securing element, is secured to the upper leg (502) while in a standing position. The wearer may optionally be standing on a scale (501) or other mechanism to measure the force on the bottom surface of the foot. The upper securing element (or artifact) is raised by applying a force (503) until the weight on the bottom surface of the foot lessens. At this point, the upper securing element is effectively transmitting force to the femur. The distance required to move the upper securing element from its initial position to the position of effectively transmitting the force to the femur is the amount of "slack" that needs to be preloaded on the upper securing element. This method measures the distance needed to remove the "slack."

Alternatively, the force required to move the upper securing element upwards far enough until the force on the bottom surface of the foot lessens could be measured. That preloaded force could be used in a fixed force preload mechanism such as described in FIG. 49.

In general, according to the current invention, one can measure the rest position or rest force against a stop applied by a limb being fitted by a JDO. A securing element or a device that mimics a securing element can be applied to the limb. The element or device can be moved in the direction of the distraction force. The position or force applied by the limb can be monitored until it is determined that the force applied to the securing element is effectively transmitted to the underlying bone structure. The distance moved or the force applied to the securing element is the amount of preload that needs to be accounted for in order for an accurate distraction amount.

Distraction Element (Aka, in Aspects, Means for Generating Joint Distraction Force)

Figure 51A:
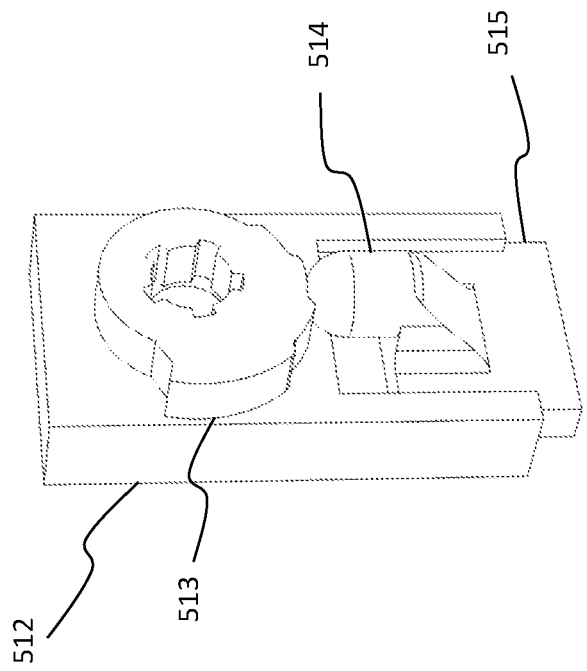
FIGS. 51a-51b illustrate a distraction mechanism suitable for a JDO.
Figure 51B:
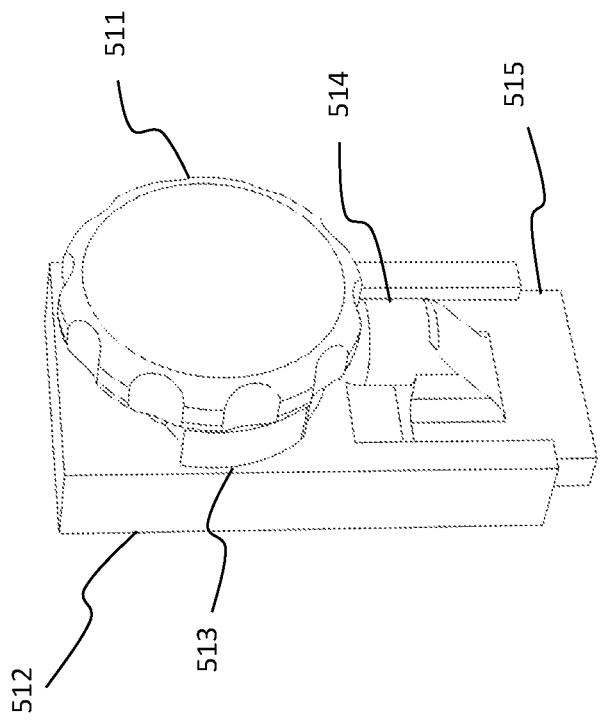

The purpose of the distraction element is to apply a strong yet controlled force across the joint to separate the bones by a predetermined amount. FIG. 51A and FIG. 51B show one embodiment of a distraction element (e.g., means for generating a joint distraction force). FIG. 51B shows the mechanism of FIG. 51a with the dial (511) removed for clarity. A dial (511) is mounted on a carrier (512). The dial is connected to a plate (513) with steps or detents. Various distances between the detents and the axis of the dial are provided such that by turning the dial, the amount of distraction distance can be selected. A pin or the like (514) is provided which engages with the steps or detent. The pin is connected to a slide (515) that slides along the carrier (512). Optionally a spring (not shown) is provided that pulls the pin assembly into a neutral position. The distraction element described is useful for gradually increasing the distraction amount across the joint to follow a particular therapy guide. In another embodiment, the plate (513) can optionally be removed and replaced with another plate with a different range of step or detent distances.

Figure 52:
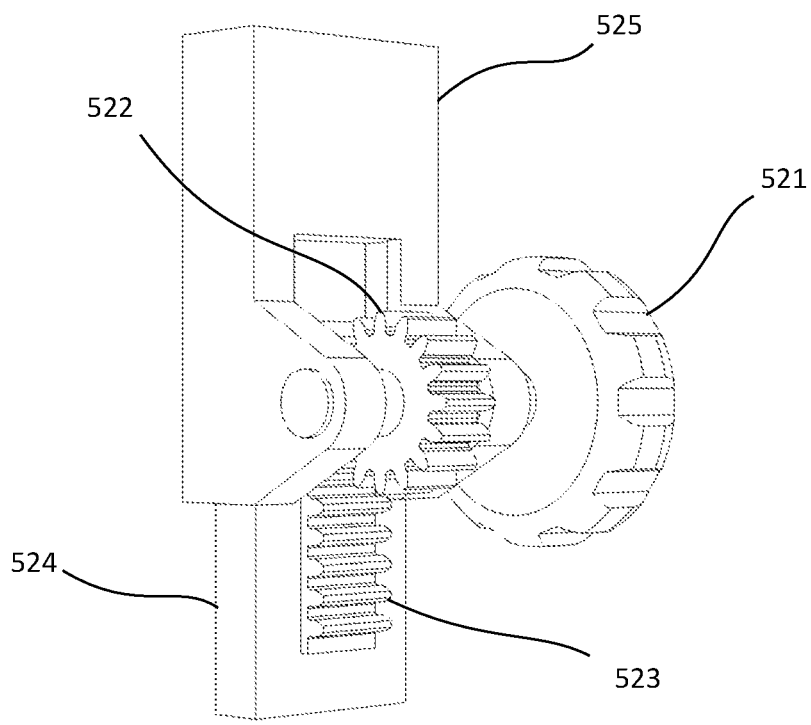
FIG. 52 illustrates a rack and pinion mechanism suitable for a JDO.

FIG. 52 shows another embodiment of a distraction element (e.g., means for generating a joint distraction force). A rack and pinion assembly is shown. A knob or dial (521) is connected to a pinion (522). Turning the knob causes the pinion to translate along the rack (523). The knob and pinion are attached to a carrier (525). A slide (524) moves with relation to the carrier. A locking mechanism is used to prevent rotation of the pinion after the desired distraction distance is obtained (not shown). As described, the distraction element is continuously variable.

In an alternative embodiment, detents in the knob (521) can be employed. The detents can serve as haptic feedback to alert the user when a predetermined distance along the rack (523) has been achieved. In yet another embodiment, the detent mechanism can serve as the locking mechanism which would ensure that the distraction element could only be set to predetermined distraction distances.

In another embodiment, a visual guide can be employed. For example a window can reveal a setting (such as a number or a color) when an appropriate distraction distance is achieved.

Figure 53:
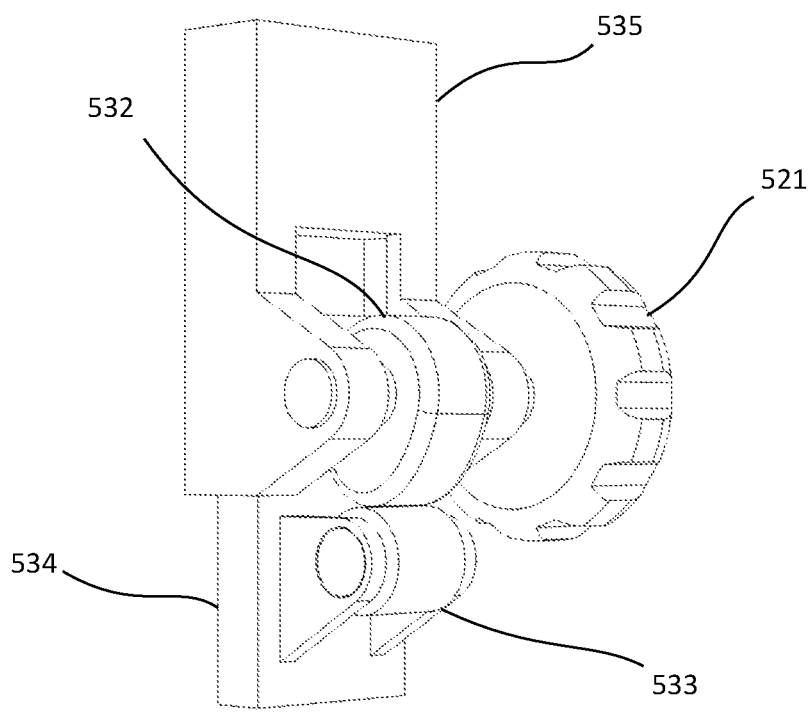
FIG. 53 illustrates a cam and follower mechanism suitable for a JDO.

FIG. 53 shows another embodiment of a distraction element (e.g., a means for generating a joint distraction force). A cam (532) and follower (533) assembly is shown. A knob (531) or lever is connected to the cam. Turning the knob causes the cam to rotate and increase the distance between the follower and the rotation axis of the cam. The cam and follower are attached to a guide (535) and a slide (534). Turning the knob or lever pushes the cam and follower apart which sets a distraction distance. A locking mechanism (not shown) is used to prevent the rotation of the cam after the desired distraction distance is obtained. As described, the distraction element is continuously variable.

In an alternative embodiment, detents in the knob or cam can be employed. The detents can serve as haptic feedback to alert the user when a predetermined distance has been achieved. In yet another embodiment, the detent mechanism can serve as the locking mechanism which would ensure that the distraction element could only be set to predetermined distraction distances. Distraction distances can be different on each side of the knee joint to better tune the orthosis to the function of an individual's knee, and/or to create joint rotation.

Figure 54:
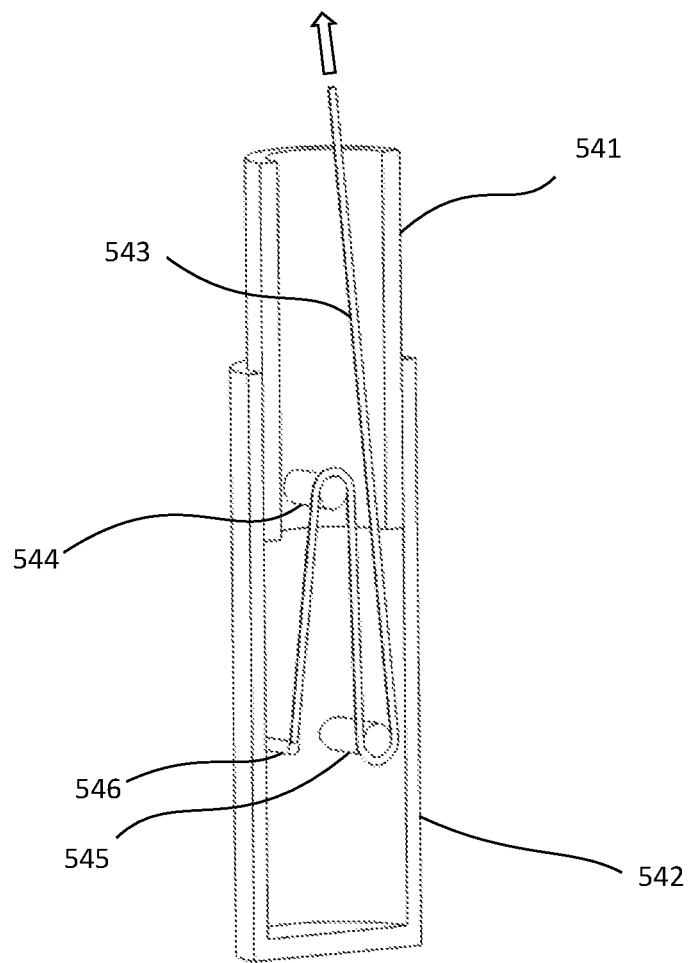
FIG. 54 illustrates a cable and tension mechanism suitable for a JDO.

FIG. 54 shows another embodiment of a distraction element (e.g., means of generating joint distraction force). An upper portion (541) and a lower portion (542) of the distraction element are connected by a sliding mechanism. Pins, guides, holes, path guides, pulleys, or the like (544), (545) are positioned to create a serpentine path as shown. A cable, string, chain, braid, cord, or the like (543) is disposed along the path and terminates at an anchor point (546). Applying a tension force to the element (543) in the direction of the arrow causes the upper portion (541) to move away from the lower portion (542) of the distraction element. The tension force can be applied by winding the cable, string, chain, braid, cord, or the like around a dial or spool such as described in U.S. patent application Ser. No. 18/075, 203. Locking mechanisms could be employed to prevent the dial or knob from unwinding. The distraction element in FIG. 54 could be configured to be continuously variable or to turn to predetermined positions by using a detent system similar to those described above.

Figure 55:
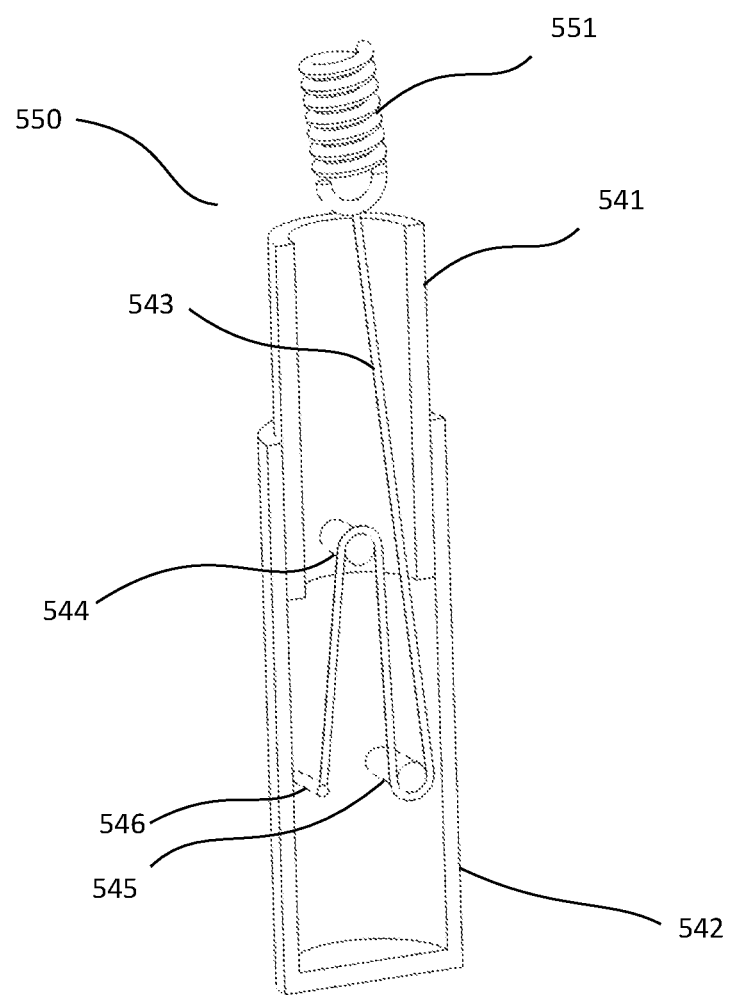
FIG. 55 illustrates a cable and tension mechanism with an in-line elastic element suitable for a JDO.

Alternatively, the tension force for the distraction mechanism of FIG. 54 could be provided by an elastic or spring mechanism (551) as shown in FIG. 55. In this configuration, the distraction element (e.g., means for generating joint distraction force) (550) would be configured to apply a constant distraction force rather than a constant distraction distance. A constant distraction force (rather than distance) is difficult to achieve using traditional joint distraction surgery and this could be another advantage of employing JDO for joint distraction over surgery such as KID.

Figure 56B:
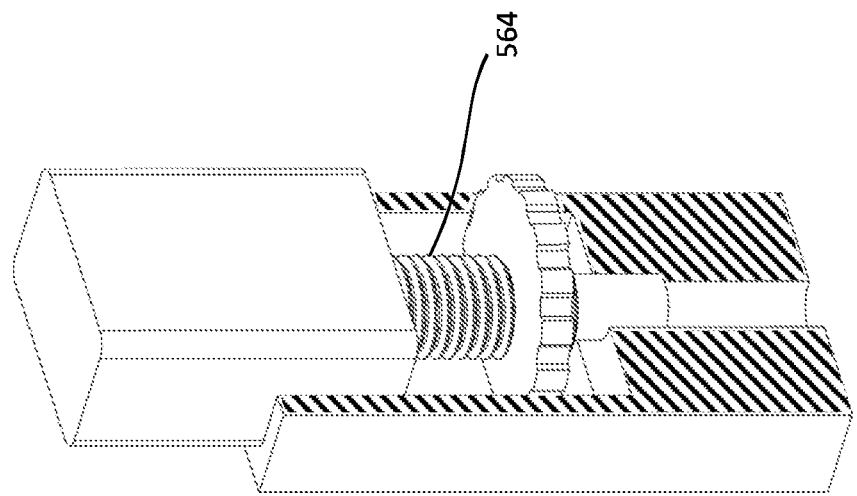
FIG. 56A-56B illustrate a threaded mechanism suitable for a JDO.
Figure 56A:
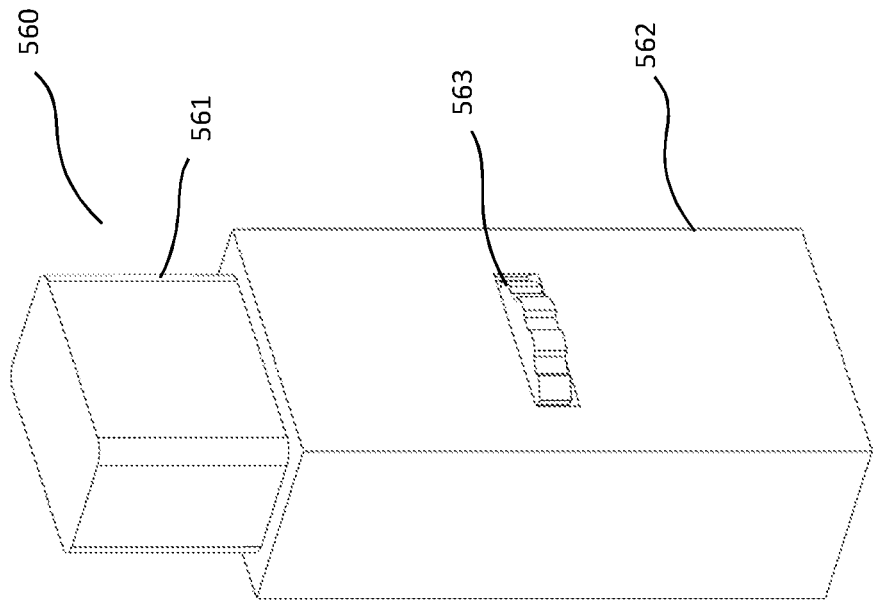

Alternatively, a distraction mechanism (e.g., means for generating joint distraction force) (560) could employ a threaded rod, ball screw, acme thread, or the like and mating nut. As shown in FIG. 56A and FIG. 56B, one end of the distraction element (561) is connected to a threaded rod (564); the other end (562) is connected to a threaded wheel (563). Half of the distraction element (562) is cut away to show the interior of the distraction mechanism (560). As shown in FIG. 56A and FIG. 56B, the wheel is captured in a slot cut into the distraction element (562). Rotating the wheel causes the two ends to move away from each other thus providing a distraction distance. (Rotating the rod/nut in the opposite direction would move the two ends towards each other thereby reducing the distraction distance.) Locking mechanisms (not shown) could be employed to prevent the rod (or nut) from unwinding. The distraction element in FIG. 56A and FIG. 56B could be configured to be continuously variable or to turn to predetermined positions by using a detent system similar to those described above.

Figure 57:
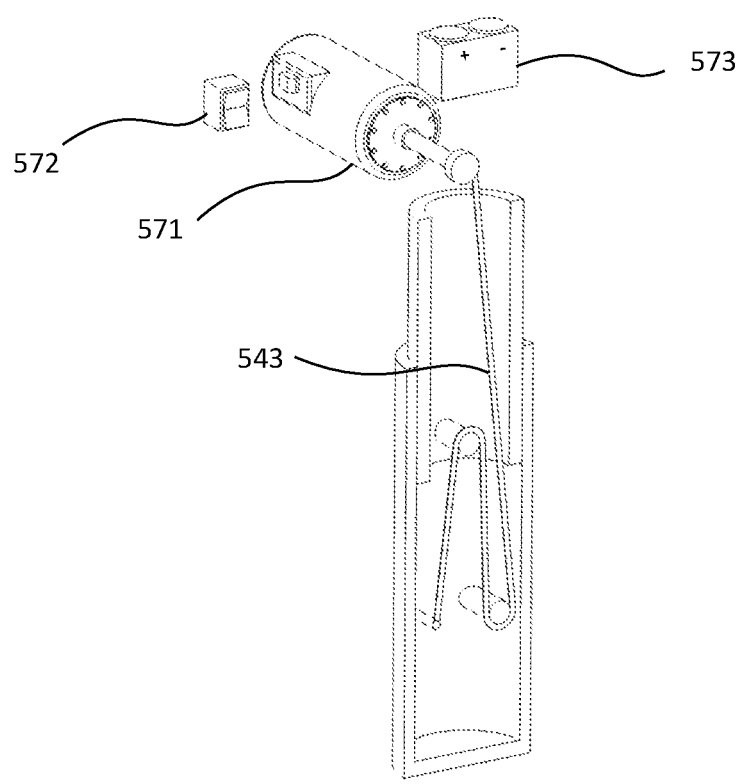
FIG. 57 illustrates an embodiment of a motorized JDO.

Powered versions of all of the previous versions of distraction elements are possible by connecting a motor to the pinion, cam, rod or nut, or cable, string, chain, braid, cord or the like. FIG. 57 shows a motor (571) and power source (573) configured to pull on the cable (543). A rocker switch (572) is shown in FIG. 57. Pressing the increase side of the rocker sends a signal to the motor to tighten the cable which causes the distraction element to move apart. Pressing on the decrease side of the rocker sends a signal to the motor to loosen the cable which causes the distraction element to move together.

Alternatively, a microprocessor or the like could be programmed to send a signal to the motor to tighten the cable a predetermined amount. The program could instruct "turn ¼ rotations"—to generate a set amount of distraction—or as complicated as an entire distraction regime wherein the distraction distance is automatically adjusted hour by hour to follow a predetermined distraction schedule.

In another embodiment, a linear actuator(s) that is connected to a power source could be used to provide the distraction distance/force.

Alternatively, a force sensor (such as a tensiometer) may be employed with a motorized distraction element. This would enable a motorized distraction element to be run in a constant force mode. That is, the motor would be energized until the desired level of force was detected by the force sensor. In aspects, a switch could be employed to increase or decrease the force or a microprocessor or the like could be programmed to set the amount of force applied by the distraction element.

Alternatively, a distance sensor (such as an optical grating) may be employed with a distraction element. The distance sensor could be configured to measure the amount of distraction provided by the distraction element. The distance sensor could be configured to provide visual, audible, and/or tactical feedback, to the user to help them set the proper distraction amount. For example, instead of using a detent system, a chime could play when the proper amount of distraction was applied with, for example, the distraction element shown in FIG. 52.

Similarly, the distance sensor could be used to control a motor that was connected to a distraction element.

In another embodiment, fiducial markers could be located on the wearer's joint. The fiducial markers could be applied to the joint (e.g., a temporary tattoo of a linear scale) or the naturally occurring markings on the wearer's skin (e.g., freckles, birthmarks, creases, wrinkles, bulges from underlying bones, and the like). An optical sensor or camera could be used to monitor the distance between the markers or the distortion of the marker as the distraction element is engaged. Feedback from the fiducial markers would be employed to alert the user or control a motor such that the proper amount of distraction was applied.

In some aspects, the pre-tensioning mechanism of the securing element and the distraction element may be substantially similar mechanically. By way of example, both could employ an eccentric cam to provide the pre-tensioning or the distraction force. In some embodiments, the pre-tensioning element could be incorporated into the distraction element. However, in most aspects, they have different functions. The pre-tensioning aspect positions the muscles, skin, and adipose tissue in an extended position so that a force applied to the skin and muscles of the limb are transmitted to the bone. The distance traveled by the distal end of the JDO due to the function of the pre-tension element may vary from individual to individual based on variations in BMI, muscle tone, etc. The distance may be as high as several centimeters in some instances.

On the other hand, the actual distraction distance of the bones in the joint is typically less than 5 mm. Because the distraction distance is prescribed by the particular medical procedure being followed it is expected that the distraction distance will not vary from individual to individual as much as the pre-tensioning distance. However, variances are envisioned.

Various embodiments of the pre-tensioning element and the distraction element could be combined into the same mechanism if the respective functions were maintained. By way of example, a rack and pinion expanding slide(s) could be incorporated into the JDO. A force sensor could track the amount of force (tension) between the distal end of the JDO and the limb. The rack and pinion could be manually adjusted or driven with a motor until a predetermined force, Fi, was achieved. Fi, in aspects, can be defined as the initial force needed to pre-tension the skin, muscle, and adipose tissue. Once Fi was reached, the rack and pinion would be adjusted (either manually or automatically) to provide the medically prescribed distraction distance.

The preceding example used a rack and pinion as the means of expanding the JDO along the limb, but any of the previously described methods could work equally well.

In an embodiment, there is a gross adjustment for pre-tensioning the JDO and a fine adjustment for the distraction element. The gross adjustment takes up most of the pre-tensioning of the skin, muscle, and adipose tissue. The fine adjustment of the distraction element takes up the final pre-tension and the distraction distance. By employing two adjustment mechanisms, the distraction element can use fine adjustment methods to precisely deliver the prescribed distraction whereas such a fine adjustment might not be appropriate for the large distances the pre-tensioning element may require. But by employing the fine adjustment to finish off the pre-tensioning, better control and accuracy could be achieved. As a non-limiting example, a fine and gross adjustment method in a single JDO could be achieved by using a fine threaded rod and a coarse threaded rod with corresponding nuts in a JDO mechanism similar to the one shown in FIG. 56A and FIG. 56B.

Locking Hinge Embodiment(s)

It is well known that the efficacy of medical orthotics, medical regimes, and medications are inversely related to the comfort and ease of use for the patient. In cases, the various versions of the JDO described above and herein can be meant to be used in a single or narrow range of joint flexion. For example, the human knee joint combines both rotational and sliding movements during leg flexion. In this manner, the preferred distraction distance between the tibia and femur changes depending on the amount of leg flexion. The JDO can be configured to change the distraction distance based on the degree of flexion. In another embodiment, the JDO is fixed at a particular (or narrow range) of flexion. For knee distraction surgery, the leg is typically fixed in a fully extended position. In at least one trial of non-surgical distraction, the leg was placed at 30 degree flexion when a weight was hung from the angle.

Walking can be difficult for many people when one leg is fully or nearly fully extended. A cane, crutch, walker or the like would likely be advised for safety reasons. Alternatively, the JDO could be removed to allow the patient to walk. Some patients would find donning and doffing a JDO inconvenient and may not be comfortable using a cane, crutches, etc. In order to make the wearing of a JDO more comfortable and less imposing, a lockable hinge can be recommended.

Figure 58B:
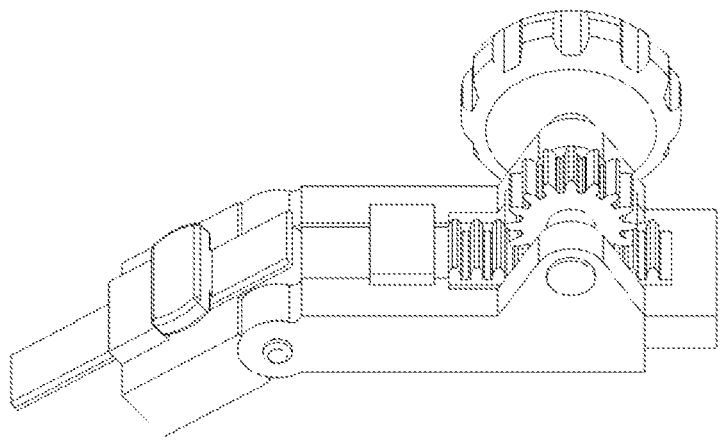
FIGS. 58A-58B show a hinged distraction mechanism suitable for a JDO.
Figure 58A:
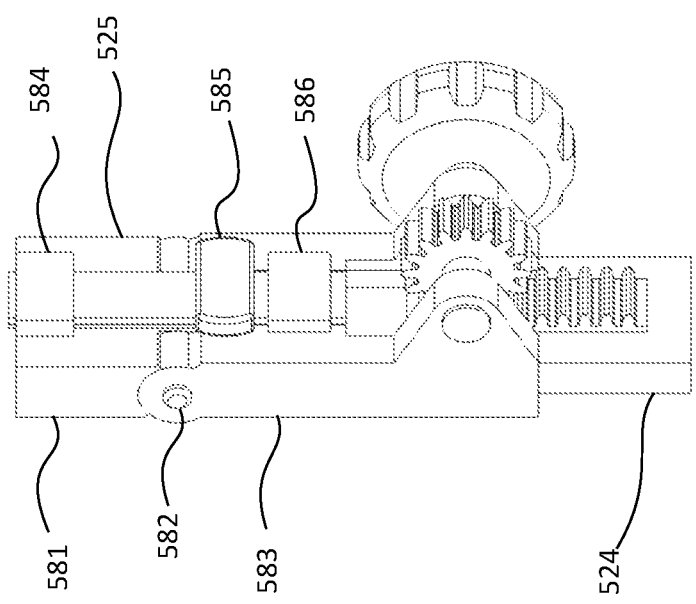

FIG. 58A and FIG. 58B show a JDO element with a hinge similar to the one shown in FIG. 52. The hinge is lockable in the fully extended position. As in FIG. 52, there is a carrier (525) and a slide (524). The carrier is divided into an upper piece (581) and a lower (583) piece that are connected by a pin (582) thereby creating a hinge. A guide (584) on the upper piece and a guide (586) on the lower piece create a channel for a slide (585). When the slide is in the locked position as shown in FIG. 58A the joint is in the fully extended position. This allows the distraction forces applied by the rack and pinion to be transmitted to the joint. To allow the leg to flex, the distraction force would be released and the slide moved to the unlock position as shown in FIG. 58B. Other means for locking and unlocking the hinge such as a dial, pins, screws, wedges, catches, and the like are also possible.

In another embodiment, applying the distraction force also has the function of locking the hinge. FIGS. 59A-59C show a hinged distraction element with a pin and cam. An upper arm (591) is connected to a lower arm (592) by a keyhole slot/tab mechanism (595, 594). Twisting a knob (593) turns a cam (597) which pushes a pin (596) attached to the upper arm thereby applying a distraction force. FIG. 59B and FIG. 59C are partial cross-section views of FIG. 59A. When the knob is turned such that the distraction element is fully disengaged (that is, not pushed apart) such as shown in FIG. 59A and FIG. 59B, the tab corresponds to a position in the keyhole slot where it is allowed to rotate. The upper arm may pivot about its tab creating the hinge motion between the upper and lower arms. When the knob is turned to engage the distraction function as is shown in FIG. 59C, the tab is moved along the keyhole slot to a position where it cannot rotate. Thus, while the distraction force is applied the JDO hinge is locked. When the distraction force is released, the tab returns to the bottom of the keyhole slot and allows the hinge to pivot. A spring or similar element (not shown) aids in the return of the upper arm to its disengaged position when the cam is not pushing on the pin.

Thus, a patient wearing a JDO with a distraction element as shown in FIG. 59A could wear the JDO at night while sleeping. Should the wearer need to get up in the middle of the night, they would not need to remove the JDO—they could simply release the distraction force.

Other methods of applying a distraction force between two elements (e.g., a means for generating a joint distraction force) include, but are not limited to, a four bar mechanism, a four bar mechanism in the format of a scissors jack, a six bar mechanism, and the like, as described herein.

Conversely, it is possible to create a distraction mechanism by using the mechanisms described above in reverse. That is, if a strong spring was pushing the two elements of a JDO element apart, a screw, wedge, cam, a slot and tab, a four bar mechanism, rack and pinion, etc., could pull the elements together. In this case, when the mechanism was disengaged, the neutral or 'at rest' position would be fully distracted. Turning a knob (as described in several embodiments above and herein) would engage the mechanisms to pull the JDO elements together and relieve the distraction forces.

The instantaneous center of rotation (sometimes called the instantaneous axis of rotation or IAOR) of a body is the reference point in the plane of motion where the relative velocity of any point in the body is zero. The IAOR is the point where the combined translation and rotation of a body can be reduced to pure rotation. By way of example, FIG. 60 shows the IAOR of a knee joint—which moves with a combination of rotation and glide—in various degrees of flexion.

The IAOR can be determined graphically by selecting two points on a body (e.g., point A and point B) and recording the position of the points at two different positions of the body (e.g. A and A', B and B'). A line is drawn connecting A to A' and the normal at the midpoint of the line is subsequently drawn. The process is repeated for points B and B'. The point where the normals intercept is the IAOR of the body as it moves from the first position to the second position. The process can be repeated for multiple positions of the body. In FIG. 60, the IAORs are shown as open circles. The path traced by the IAOR as the body moves through a plane is called the centrode.

Figure 60:
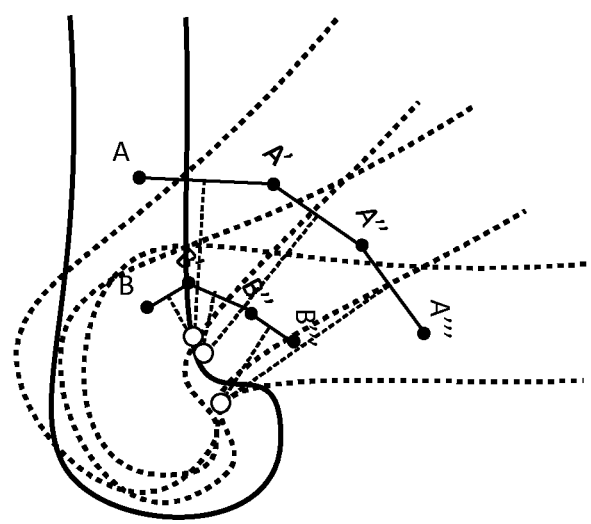
FIG. 60 shows a schematic of the centrode path of a human knee in flexion.
Figure 61C:
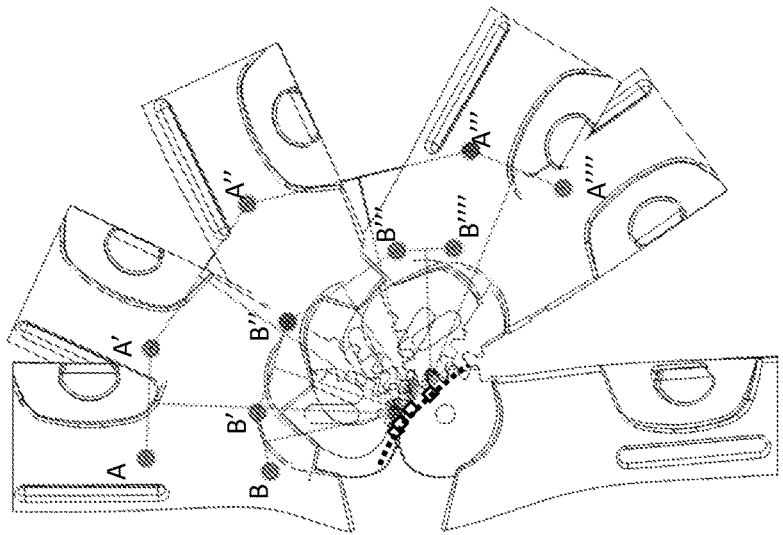
FIGS. 61A-61C show the centrode paths of three types of distraction mechanisms.
Figure 61B:
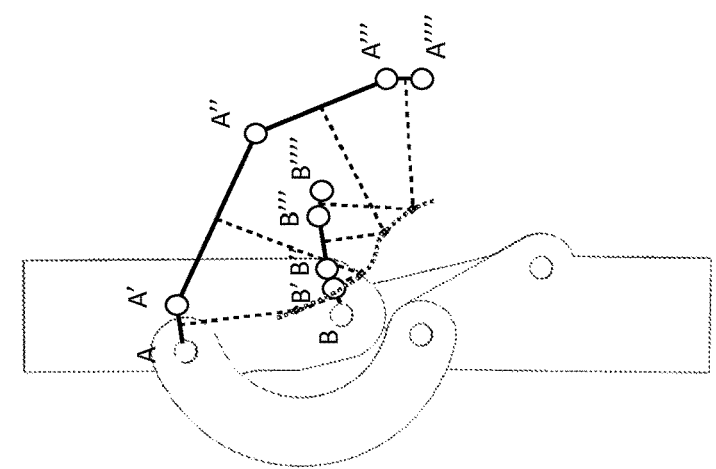
Figure 61A:
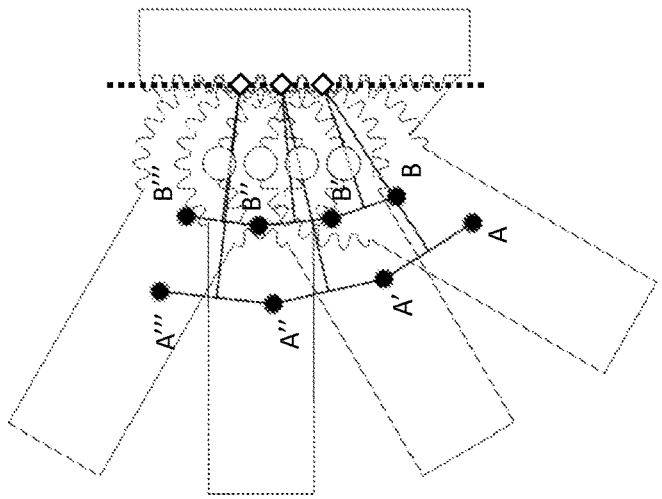

As shown in FIG. 60, the centrode of the human knee is not a straight line. The centrodes of some of the JDO aspects described herein are shown in FIG. 61. FIG. 61A shows the centrode of a rack and pinion JDO similar to the aspect as described in FIG. 48. Two points (A and B) are marked on the arm connected to the pinion gear. Four different positions of the arm-and-pinion are superimposed upon the rack. A line is drawn to connect A with A', A' with A'', and A'' with A'''. A normal is drawn at the midpoints of each of the line segments. Similarly, line segments connect B with B', B' with B'', and B'' with B'''. Additionally, normals are drawn from the midpoints of these line segments. The intersection of the pairs of normals (each an IAOR) are shown as diamonds. The centrode that connects the diamonds is drawn as a dotted line. This convention—diamonds for the IAORs and dotted lines for the centrode—is repeated in FIG. 61B and FIG. 61C.

As shown, the centrode of a rack and pinion distraction mechanism is a continuous straight line. FIG. 61B shows a four bar linkage distraction mechanism similar to the mechanism shown in FIGS. 40-43. For simplicity, the locations of all four bars are not shown for four different flexion angles of the upper bar, however the locations of the pivot points A and B are shown. As before, a line segment connects A to A', A'' to A''', etc. and normals to those line segments are drawn. Line segments and normals are drawn for B and B', B' and B'', etc. The intersection of the normal lines (the IAORs) are marked with diamonds and a dotted line connects the IAORs. The centrode for a four bar linkage is a continuous curvilinear (e.g., nonlinear) path. The shape and orientation of the centrode can be altered by changing the length of the bars and location of the pivot points.

FIG. 61C shows the variable radiused geared distraction mechanism similar to the one in FIG. 26A and FIG. 26B. Five different positions of the upper arm are superimposed in FIG. 61C. As before, a line segment connects A to A', A'' to A''', etc. and normals to those line segments are drawn. Line segments and normals are drawn for B and B', B' and B'', etc. The intersection of the normal lines (the IAORs) are marked with diamonds and a dotted line connects the IAORs. The centrode for a variable radiused geared distraction mechanism is a continuous curvilinear path.

The centrode of a compound hinge such as the mechanisms shown in FIGS. 28-30 and FIGS. 33-38 is not a continuous path but two discrete points. As the lower arm 282 rotates about the pivot point 299 engaging the corresponding teeth in the upper arm 280 as shown in FIG. 28C, the IAOR of the lower arm 282 is the pivot point 299. At the point where the pin 283 reaches the end of the travel of the groove 288 as shown in FIG. 29B, the lower arm 282 ceases to rotate about the pivot point 299. Further clockwise rotation of the lower arm 282 occurs as it pivots about the point 298 as shown in FIG. 30A and FIG. 30B. The IAOR of the lower arm 282 is the pivot point 298 over the range of rotation shown from FIG. 29B to that shown in FIG. 30B. In a similar manner, the IAORs for the upper arm 280 are also two discrete points.

Pairing a distraction mechanism whose centrode matches, substantially matches, mimics, or otherwise resembles, the centrode of the joint will lead to a superior JDO, such as the invention described herein. For example, the centrode of the human knee is a curvilinear (e.g., nonlinear) path that moves toward the posterior when the knee is in flexion.

Aspects of the current invention can include, but are not limited to, the following:

Aspect 1: A Joint Distraction Orthotic comprising securing elements and a distraction element where:

the distraction element (e.g., means for generating a joint distraction force) provides a force sufficient to open the joint thereby allowing to body to heal damage to the joint;

and the securing elements are configured to effectively transmit the distraction force to the underlying bones on either side of the joint.

Aspect 2: The JDO of Aspect 1 wherein:
At least one securing element has a mechanism that is able to account for the difference between the distraction distance applied to the securing elements and the actual distraction distance effectively applied to the joint due to the skin, muscle, and adipose tissue of the wearer's limb or body.

Aspect 3: The JDO of Aspect 2 wherein:
At least one securing element is contoured to the limb with a flexible cuff.

Aspect 4: The JDO of Aspect 2 wherein:
At least one securing element is contoured to the limb by using a 3D scan of the limb to customize at least part of the shape of the securing element to the limb.

Aspect 5: The JDO of Aspect 2 wherein:
At least one securing element has a rigid or semi-rigid cuff that cups the anterior of the limb and a rigid or semi-rigid cuff that cups the posterior of the limb.

Aspect 6: The JDO of Aspect 2 wherein:
The mechanism to account for the difference between the distraction distance applied to the securing elements and the actual distraction distance effectively applied to the joint due to the skin, muscle, and adipose tissue of the wearer's limb or body comprises at least one of an eccentric cam and follower, a rack and pinion, a threaded rod and nut, and a cable and guide path.

Aspect 7: The JDO of Aspect 2 wherein:
The securing elements on either side of the joint employ different mechanisms to account for the difference between the distraction distance applied to the securing elements and the actual distraction distance effectively applied to the joint due to the skin, muscle, and adipose tissue of the wearer's limb or body.

Aspect 8: The JDO of Aspect 2 wherein:
The difference between the distraction distance applied to the securing elements and the actual distraction distance effectively applied to the joint due to the skin, muscle, and adipose tissue of the wearer's limb or body is measured and at least one of the securing elements is configured to remove that amount.

Aspect 9: The JDO of Aspect 1 wherein:
The distraction element (e.g., means for generating a joint distraction force) applies a force to separate the bones of the joint using at least one of a rack and pinion, eccentric cam and follower, threaded rod and nut, cable and guides.

Aspect 10: The JDO of Aspect 1 wherein:
The distraction element (e.g., means for generating a joint distraction force) employs at least one of detents and audible or visual feedback, to let the user know of the amount of distraction applied to the joint.

Aspect 11: The JDO of Aspect 1 wherein:
A force gauge is used to measure the force applied while distracting the joint.

Aspect 12: The JDO of Aspect 1 wherein:
A distance gauge is used to measure the distraction distance of the joint either directly or indirectly.

Aspect 13: The JDO of Aspect 1 wherein:
A motor is used to provide the distraction force.

Aspect 14: The JDO of Aspect 1 wherein:
A microcontroller is connected to at least one sensor in the JDO which is used to adjust the motor to provide a desired distraction force.

Aspect 15: The JDO of Aspect 1 wherein:
A hinge allows the wearer to flex the limb or body part wearing the JDO.

The dimensions, materials, number and type of tensioning elements, and so forth, can be modified to achieve an equivalent level of pain relief as the embodiments disclosed herein.

Although various features of the invention may be described in the context of a single embodiment, the features may also be provided separately or in any suitable combination. Conversely, although the invention may be described herein in the context of separate embodiments for clarity, the invention may also be implemented in a single embodiment.

As used herein, the term "about" refers to plus or minus 5 units (e.g., percentage) of the stated value.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

"Attachable" as used herein can mean releasably attachable, such as a component that can be attached and then detached, or a component that is attached and remains attached.

As used herein, the term "substantial" and "substantially" refers to what is easily recognizable to one of ordinary skill in the art.

It is to be understood that the phraseology and terminology employed herein is not to be construed as limiting and are for descriptive purpose only.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including," "comprising," "consisting" and grammatical variants thereof do not preclude the addition of one or more components, features, steps, or integers or groups thereof and that the terms are to be construed as specifying components, features, steps or integers.

What is claimed:
1. A joint orthosis comprising:
a first member having a first instantaneous center of rotation and a first pivot point, a second member having a second instantaneous center of rotation and a second pivot point, and a means for generating a joint distracting force;
wherein the first member is worn upon a first body part;
wherein the second member is worn upon a second body part;
wherein the first body part and the second body part are connected by a body joint, wherein the body joint articulates over a range of articulation;
wherein the means for generating the joint distracting force pushes apart or pulls apart the first member and the second member by at least 5 mm to increase a distance between the first pivot point and the second pivot point, thereby providing a distraction force to the body joint; and
wherein a path of the first instantaneous center of rotation, a path of the second instantaneous center of rotation, or both the path of the first instantaneous center of rotation and the path of the second instantaneous center of rotation, is a nonlinear path, include a set of at least two discontinuous points, or combinations thereof.

2. The joint orthosis of claim 1, wherein the joint distracting force is applied on a medial side of the body joint, a lateral side of the body joint, or both the medial side of the body joint and the lateral side of the body joint.

3. The joint orthosis of claim 1, wherein an amount of distraction over a first subrange of the range of articulation differs from an amount of distraction over a second subrange of the range of articulation.

4. The joint orthosis of claim 1, wherein a majority of the distraction force is applied within about 60 degrees of rotation of substantially full extension of the body joint.

5. The joint orthosis of claim 1, wherein the means for generating the joint distracting force comprises:
   two sets of connected polycentric hinges, a first polycentric hinge and a second polycentric hinge;
   the first polycentric hinge comprising a first upper gear and first lower gear, a first upper pivot point and a first lower pivot point, and an upper pin and a lower pin;
   an upper inner cap and a bottom inner cap, the upper inner cap comprising a first upper arc slot, a second upper gear, a second upper pivot point, and an upper edge, wherein the upper pin is positioned within the first upper arc slot to define an arc of rotation about the first upper pivot point;
   the lower inner cap comprising a first lower arc slot, a second lower gear, a second lower pivot point, and a lower edge, wherein the lower pin is positioned with the first lower arc slot to define an arc of rotation about the first lower pivot point;
   a center cap comprising a second upper arc slot and a second lower arc slot, wherein the upper pin is positioned within the second upper arc slot and the lower pin is positioned within the second lower arc slot; and
   an upper arm connected to the first upper gear and a lower arm connected to the first lower gear;
   wherein when the upper edge of the upper inner cap contacts the upper arm, the arc of rotation of the upper arm is transferred to the second upper pivot point, and/or when the lower edge of the lower inner cap contacts the lower arm, the arc of rotation of the lower arm is transferred to the second lower pivot point; and
   wherein the upper pin positioned within the second upper arc slot of the center cap and/or the lower pin positioned within the second lower arc slot of the center cap prevent further rotation of the upper arm around the first upper pivot point and the lower arm around the first lower pivot point.

6. The joint orthosis of claim 1, wherein the means for generating the joint distracting force comprises:
   the first member having a first surface and the second member having a second surface, wherein a radius of the first surface varies about the first pivot point, wherein a radius of the second surface varies about the second pivot point, or wherein both the radius of the first surface varies about the first pivot point and the radius of the second surface varies about the second pivot point; and
   a substantially non-elastic, flexible tension element that follows a first path along the first member and follows a second path along the second member, wherein the tension element holds the first surface and the second surface so that the first surface and second surface remain in contact with one another; and
   wherein a combined length of the first path and the second path remains substantially unchanged throughout a range of rotation of the first member with respect to the second member.

7. The joint orthosis of claim 1, wherein the means for generating the joint distracting force comprises:
   a four bar linkage mechanism wherein the first member is one bar of the four bar linkage mechanism, the second member is a second bar of the four bar linkage mechanism, a linkage is a third bar of the four bar linkage mechanism, and a cap is a fourth bar of the four bar linkage mechanism;
   wherein the first instantaneous center of rotation of the first member moves closer to the second instantaneous center of rotation of the second member by at least 5 mm when the first member is rotated relative to the second member.

8. The joint orthosis of claim 1, wherein the means for generating the joint distracting force comprises:
   the first member having a first geared surface at a first end, the first pivot point, and a first sliding pin;
   the second member having a second geared surface at a second end, the second pivot point, and a second sliding pin, wherein the first geared surface meshes with the second geared surface as the first member rotates about the first pivot point and the second member rotates about the second pivot point;
   a first linkage that connects the first pivot point to a third sliding pin, and a second linkage that connects the second pivot point to the third sliding pin;
   a hinge cap with a first straight slot in which the third sliding pin slides, a first arced slot in which the first sliding pin slides, and a second arced slot in which the second sliding pin slides;
   wherein the third sliding pin sliding within the first straight slot causes the first linkage and the second linkage to move simultaneously in a mirrored fashion;
   wherein the first linkage acting upon the first member and the first sliding pin sliding in the first arced slot, and wherein the second linkage acting upon the second member and the second sliding pin sliding in the second arced slot pushes the first member apart from the second member.

9. The joint orthosis of claim 1, wherein the means for generating the joint distracting force comprises:
   a flexible, substantially inelastic element that holds together the first member and the second member, wherein the flexible, substantially inelastic element loops around the first pivot point of the first member, criss-crosses itself at least once substantially near a junction of the first member and the second member, and then loops around the second pivot point of the second member.

10. The joint orthosis of claim 9, wherein a tightness or tension of the flexible, substantially inelastic element is capable of being adjusted by a moveable, adjustable mechanism that is connected to at least one part of the flexible, substantially inelastic element.

11. The joint orthosis of claim 1, wherein the means for generating the joint distracting force comprises: a polycentric pivoting hinge comprising teethed gears, wherein the teethed gears comprise variable radii providing the joint distraction of the body joint as a degree of flexion of the body joint changes.

12. The joint orthosis of claim 1, further comprising a tensioning element, wherein the means for generating the joint distracting force is a pivoting hinge between the first member and the second member, wherein the tensioning element generates tension as the tensioning element is drawn over the pivoting hinge between the first member and the second member, or wherein the tensioning element is located within either or both the first member and the second member and attached to wires or lace that are drawn over the pivoting hinge, and wherein the tensioning element is capable of applying equal tension, about equal tension, or different tensions on one side of the joint orthosis compared to a second side of the joint orthosis.

13. The joint orthosis of claim 12, wherein an amount of force generated by the tensioning element is adjustable.

14. The joint orthosis of claim 12, wherein an amount of force generated by the tensioning element is adjustable while a user is wearing the joint orthosis.

15. The joint orthosis of claim 1, wherein an amount of distraction force generated by the means for generating the joint distracting force is adjustable.

16. The joint orthosis of claim 1, wherein an amount of distraction force generated by the means for generating the joint distracting force is adjustable while a user is wearing the joint orthosis.

17. The joint orthosis of claim 1, wherein the first member, the second member, the means for generating the joint distracting force, or combinations thereof, are shaped to a user's body joint or limb based on a body joint or limb measurement, three-dimensional scan of the user's body joint or limb, patient body size or composition, or radiographic scan of the user's body joint or limb.

18. The joint orthosis of claim 1, wherein an amount of the joint distraction force is capable of being tailored to a user based on a three-dimensional scan, patient body size or composition, body joint or limb measurements, user-reported information, radiographic information, or a combination thereof, and wherein the amount of the joint distraction force may vary with degree of flexion of the body joint and/or from one side of the body joint to a second side of the body joint.

19. The joint orthosis of claim 1, wherein the distraction force generated by the means for generating the joint distracting force is between one pound or more and 100 pounds or less.

20. The joint orthosis of claim 1, wherein the means for generating the joint distracting force comprises: a frame element with two or more sliding pins, a hinge element with two or more grooves, wherein when the sliding pins follow the paths defined by the grooves the frame element translates and optionally rotates thereby generating the distraction force.

21. A joint orthosis comprising:
a first member;
a second member;
a means for generating a distracting force including a polycentric hinge connecting the first member and the second member;
wherein the first member is connected to a first body part, the second member is connected to a second body part, and wherein the first body part and the second body part are connected by a body joint;
wherein the joint orthosis articulates in a range of articulation;
wherein the means for generating the distracting force applies a first distraction force at a first point or over a first subrange of the range of articulation, wherein the means for generating the distracting force applies a second distraction force at a second point or over a second subrange of the range of articulation, and wherein the first distraction force is different than the second distraction force.

22. A joint brace comprising the following components:
a. an upper portion and a lower portion, wherein the upper portion comprises upper rigid, semi-rigid, or soft portions that fit a wearer's first body part adjacent to or above a wearer's joint, and wherein the lower portion comprises lower rigid, semi-rigid, or soft portions that fit a wearer's second body part adjacent to or below the wearer's joint; and
b. at least one polycentric pivoting hinge assembly providing a means for generating a joint distraction force located between the upper portion and the lower portion; and wherein the means for generating the joint distraction force pushes apart the upper portion and the lower portion to distract the wearer's joint as the wearer's joint moves from a flexion position to an extension position.

23. The joint brace of claim 22, wherein an amount of distraction force versus flexion of the joint brace is adjustable.

24. The joint brace of claim 22, further comprising a tensioning element, wherein the tensioning element generates tension as the tensioning element is drawn over the at least one pivoting hinge assembly, or wherein the tensioning element is located within either or both the upper portion and the lower portion and attached to wires or lace that are drawn over the at least one pivoting hinge assembly, and wherein the tensioning element is capable of applying equal tension, about equal tension, or different tensions on one side of the joint brace compared to a second side of the joint brace.

25. The joint brace of claim 24, wherein an amount of force generated by the tensioning element is adjustable.

26. The joint brace of claim 24, wherein an amount of force generated by the tensioning element is adjustable while a user is wearing the joint brace.

27. The joint brace of claim 22, wherein an amount of force generated by the means for generating the joint distraction force is adjustable.

28. The joint brace of claim 22, wherein an amount of force generated by the means for generating the joint distraction force is adjustable while a user is wearing the joint brace.

29. A joint orthosis comprising a means for generating a joint distracting force comprising:
a first member attached to a first body part and a second member attached to a second body part;
a sensor to monitor a degree of flexion of a body joint, wherein the body joint connects the first body part to the second body part;
a power source; and
a motor or actuator, wherein the motor or actuator causes the pushing apart or pulling apart of the first member of the joint orthosis and the second member of the joint orthosis when the sensor signals that a predetermined degree of flexion has been met and the joint distracting force is to be applied to the body joint.

30. The joint orthosis of claim 29, wherein the means for generating the joint distracting force further comprises a toggle switch, a rotatable knob, or a touch button, capable of increasing and/or decreasing the distracting force applied to the body joint.

\* \* \* \* \*